United States Patent [19]

Kamber et al.

[11] Patent Number: 4,616,002
[45] Date of Patent: Oct. 7, 1986

[54] DIHYDRO PYRIDINE COMPOUNDS, COMPOSITIONS AND USE

[75] Inventors: Bruno Kamber, Arlesheim; Thomas Leutert, Dornach; Hans Kühnis, Basel; Kurt Eichenberger, Therwil, all of Switzerland

[73] Assignee: Ciba-Geigy Corporation, Ardsley, N.Y.

[21] Appl. No.: 816,461

[22] Filed: Jan. 6, 1986

Related U.S. Application Data

[63] Continuation-in-part of Ser. No. 669,705, Nov. 9, 1984, abandoned.

[51] Int. Cl.[4] .................. A61K 31/535; A61K 37/02; C07D 413/12; C07K 5/06
[52] U.S. Cl. .................................. 514/18; 544/120; 544/121; 514/19; 544/122; 544/128; 514/222; 544/129; 544/131; 514/230; 544/182; 544/216; 514/231; 544/238; 544/295; 514/232; 544/333; 544/357; 514/234; 544/358; 544/363; 514/241; 544/365; 544/405; 514/242; 546/144; 546/167; 514/252; 546/187; 546/193; 514/269; 546/194; 546/256; 514/307; 546/257; 546/262; 514/314; 546/263; 546/270; 514/316; 546/271; 546/273; 514/318; 546/269; 546/274; 514/332; 546/275; 546/276; 514/333; 546/277; 546/278; 514/337; 546/279; 546/280; 514/338; 546/281; 546/283; 514/339; 546/284; 546/286; 514/340; 546/308; 546/309; 514/341; 546/316; 260/112.5 R; 514/342; 514/343; 514/344; 514/355; 514/356; 544/58.6; 544/82; 544/96; 544/112; 544/113; 544/114
[58] Field of Search .............. 544/58.6, 82, 114, 122, 544/112, 113, 128, 129, 182, 120, 121, 131, 216, 238, 295, 333, 357, 358, 363, 365, 405, 96; 546/144, 167, 187, 193, 194, 256, 257, 262, 263, 270, 271, 273, 274, 269, 275, 276, 277, 278, 279, 280, 281, 283, 284, 286, 308, 309, 316, 258; 260/112.5 R; 514/18, 19, 222, 230, 231, 232, 234, 241, 242, 252, 269, 307, 314, 316, 318, 332, 333, 337, 338, 339, 340, 341, 342, 343, 344, 355, 356

[56] References Cited

FOREIGN PATENT DOCUMENTS 2105989 4/1983 United Kingdom .

OTHER PUBLICATIONS

Jouin et al, *J. American Chem. Soc.*, vol. 103, pp. 2091-2093 (1981).

*Primary Examiner*—Robert W. Ramsuer
*Attorney, Agent, or Firm*—Karl F. Jorda; Michael W. Glynn; Bruce M. Collins

[57] ABSTRACT

Compounds of the formula I

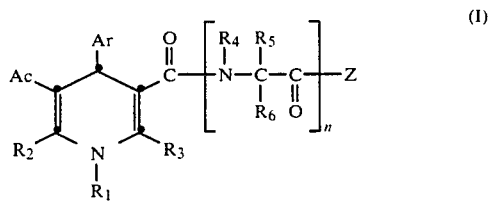

in which n represents 1, 2 or 3, Ar represents a carbocyclic or heterocyclic aryl radical, Ac represents the acyl radical of an acid, Z represents a radical $-OR_7$ or $-NR_8R_9$, $R_1$ represents hydrogen, unsubstituted or substituted lower alkyl, a carbocyclic or heterocyclic aryl radical or free, etherified or esterified hydroxy, $R_2$ and $R_3$, independently of one another, each represents hydrogen, unsubstituted or substituted lower alkyl, formyl or functionally modified formyl, carboxy or functionally modified carboxy, a carbocyclic or heterocyclic aryl radical or unsubstituted or mono- or di-substituted amino, $R_4$ represents hydrogen or lower alkyl, $R_5$ and $R_6$, independently of one another, each represents hydrogen, unsubstituted or substituted lower alkyl or a carbocyclic or heterocyclic aryl radical, $R_7$, $R_8$ and $R_9$, independently of one another, each represents hydrogen, unsubstituted or substituted alkyl or a carbocyclic or heterocyclic aryl radical; in which $R_1$ and $R_2$ together or $R_1$ and $R_3$ together may represent unsubstituted or substituted lower alkylene in which a carbon atom is optionally replaced by a hetero atom, in which $R_4$ and $R_5$ together, and likewise $R_5$ and $R_6$ together and/or $R_8$ and $R_9$ together, independently of one another, may represent unsubstituted or substituted lower alkylene in which a carbon atom may have been replaced by a hetero atom, optical isomers of compounds of the formula I, mixtures of these optical isomers and salts of such compounds that have a salt-forming grouping, are distinguished by cardiovascular, especially blood pressure-reducing, properties. They are manufactured in a manner known per se.

32 Claims, No Drawings

DIHYDRO PYRIDINE COMPOUNDS, COMPOSITIONS AND USE

This is a continuation-in-part-application of our co-pending application Ser. No. 669,705, filed Nov. 9, 1984 now abandoned.

The invention relates to novel amide compounds and salts thereof, processes for their manufacture, pharmaceutical preparations containing such compounds, and their use for the manufacture of pharmaceutical preparations or as pharmacologically active compounds.

The invention relates especially to substituted 3-carbamoyl-1,4-dihydropyridine compounds of the formula I

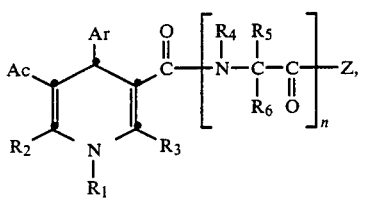

in which n represents 1, 2 or 3, Ar represents a carbocyclic or heterocyclic aryl radical, Ac represents the acyl radical of an acid, Z represents a radical —$OR_7$ or —$NR_8R_9$, $R_1$ represents hydrogen, unsubstituted or substituted lower alkyl, a carbocyclic or heterocyclic aryl radical or free, etherified or esterified hydroxy, $R_2$ and $R_3$, independently of one another, each represents hydrogen, unsubstituted or substituted lower alkyl, formyl or functionally modified formyl, carboxy or functionally modified carboxy, a carbocyclic or heterocyclic aryl radical or unsubstituted or mono- or di-substituted amino, $R_4$ represents hydrogen or lower alkyl, $R_5$ and $R_6$, independently of one another, each represents hydrogen, unsubstituted or substituted lower alkyl or a carbocyclic or heterocyclic aryl radical, $R_7$, $R_8$ and $R_9$, independently of one another, each represents hydrogen, unsubstituted or substituted alkyl or a carbocyclic or heterocyclic aryl radical; in which $R_1$ and $R_2$ together or $R_1$ and $R_3$ together may represent unsubstituted or substituted lower alkylene in which a carbon atom is optionally replaced by a hetero atom, in which $R_4$ and $R_5$ together, and likewise $R_5$ and $R_6$ together and/or $R_8$ and $R_9$ together, independently of one another, may represent unsubstituted or substituted lower alkylene in which a carbon atom may have been replaced by a hetero atom, to optical isomers of compounds of the formula I, mixtures of these optical isomers and salts of such compounds that have a salt-forming grouping, processes for the manufacture of these compounds, pharmaceutical agents containing such compounds, and their use for the manufacture of pharmaceutical preparations or as pharmacologically active compounds.

The definitions used hereinbefore and hereinafter, unless specifically defined otherwise, have the following meanings:

The term "lower" means that groups or compounds so defined have up to and including 7, preferably up to and including 4, carbon atoms.

Substituted radicals may contain one or more identical or different substituents; these may substitute at any suitable position.

In the above formula I, n represents especially 1 but may also represent 2 or 3. If n is 2 or 3, the radicals $R_4$, $R_5$ and $R_6$, of which there are then a plurality, are in each case independent of one another.

A carbocyclic or heterocyclic aryl radical is especially a corresponding monocyclic radical but may also be a bicyclic or polycyclic carbocyclic or heterocyclic radical having aromatic properties.

Carbocyclic radicals of this type are especially phenyl, also naphthyl, for example 1- or 2-naphthyl.

Heterocyclic aryl radicals are preferably corresponding monocyclic radicals but may also be corresponding bicyclic or polycyclic radicals; the latter may consist of several heterocyclic rings, or of one or more heterocyclic rings having one or more fused-on carbocyclic rings, especially one or more fused-on benzo rings. The heterocyclic radicals which are normally present and which preferably consist of five or six ring members, may contain as ring members up to four identical or different hetero atoms, especially nitrogen, oxygen and/or sulphur atoms, preferably one, two, three or four nitrogen atoms, one oxygen or sulphur atom, or one or two nitrogen atoms together with one oxygen or sulphur atom. They are generally bonded by a ring carbon atom to the 4-ring carbon atom of the 1,4-dihydropyridine ring.

Monocyclic five-membered heteroaryl radicals are, for example, corresponding monoaza-, diaza-, triaza-, tetraza-, monooxa-, monothia-, oxaza-, oxadiaza-, thiaza- or thiadiaza-cyclic radicals, such as pyrryl, pyrazolyl, imidazolyl, triazolyl, tetrazolyl, furyl, thienyl, isoxazolyl, oxazolyl, oxadiazolyl, isothiazolyl, thiazolyl or thiadiazolyl radicals, while monocyclic, six-membered heteroaryl radicals are, for example, corresponding monoaza-, diaza- or triaza-cyclic radicals, such as pyridyl, pyridazinyl, pyrimidinyl, pyrazinyl or triazinyl radicals. Bicyclic heteroaryl radicals are especially monocyclic heteroaryl radicals having a fused-on benzo ring; the hetero ring may be five- or six-membered, the five-membered heteroaryl radical being, for example, a monoaza-, diaza-, monooxa-, monothia-, oxaza-, thiaza-, oxadiaza- or thiadiaza-cyclic radical, and the six-membered heteroaryl radical being, for example, a monoaza- or a diaza-cyclic heteroaryl radical. Such bicyclic radicals are, for example, indolyl, isoindolyl, benzimidazolyl, benzofuranyl, benzothienyl, benzothiazolyl, benzoxadiazolyl, benzothiadiazolyl, quinolinyl or isoquinolinyl radicals.

The carbocyclic and heterocyclic aryl radicals Ar may be unsubstituted or substituted, it being possible especially for ring carbon atoms, but also for ring nitrogen atoms, to be substituted. Substituents of ring carbon atoms are, inter alia, optionally substituted hydrocarbon radicals, such as corresponding aliphatic, cycloaliphatic, aromatic or araliphatic hydrocarbon radicals, such as lower alkyl, lower alkenyl, lower alkynyl, lower alkylene, cycloalkyl, cycloalkyl-lower alkyl, phenyl, phenyl-lower alkyl, phenyl-lower alkylthio and/or phenyl-lower alkoxy; substituents of such hydrocarbon radicals, especially of lower alkyl, phenyl, phenyl-lower alkyl, phenyl-lower alkylthio and/or phenyl-lower alkoxy, may be, for example, optionally etherified or esterified hydroxy groups, such as hydroxy, lower alkoxy, lower alkenyloxy, lower alkynyloxy, lower alkylenedioxy, lower alkanoyloxy or halogen, and/or optionally functignally modified carboxy, such as carboxy, esterified carboxy, for example lower alkoxycarbonyl, amidated carboxy, such as carbamoyl, N-lower alkylcarbamoyl or N,N-di-lower alkylcarbamoyl, or cyano. In addition, cyclic substituents, especially phenyl, may contain as substituent also lower alkyl which may be optionally substituted, for example as indicated. Further substituents of aryl radicals Ar are, for example, optionally etherified or esterified hydroxy groups, such as hydroxy, lower alkoxy, halo-lower alkoxy, lower alkenyloxy, halo-lower alkenyloxy, lower alkynyloxy, lower alkylenedioxy, lower alkanoyloxy or halogen, nitro, optionally substituted amino, such as amino, lower alkylamino, di-lower alkylamino, N-lower alkyl-N-phenyl-lower alkylamino, lower alkyleneamino, oxa-lower alkyleneamino, thia-lower alkyleneamino or aza-lower alkyleneamino, it being possible for the aza-nitrogen atom to be unsubstituted or substituted, for example by lower alkyl, phenyl or phenyl-lower alkyl which are optionally substituted, for example as described above, or acylamino, for example lower alkanoylamino, azido, acyl, such as lower alkanoyl, or optionally functionally modified carboxy, such as carboxy, esterified carboxy, for example lower alkoxycarbonyl, or amidated carboxy, such as carbamoyl, N-lower alkylcarbamoyl or N,N-di-lower alkylcarbamoyl, or cyano, optionally functionally modified sulpho, such as sulpho or aminosulphonyl, and/or etherified mercapto, which may optionally be oxidised, such as lower alkylthio, lower alkylsulphinyl or lower alkylsulphonyl. Substituents of ring nitrogen atoms are especially the above-mentioned optionally substituted hydrocarbon radicals, such as lower alkyl or lower alkoxycarbonyl, also hydroxy or oxido.

Heterocyclic aryl radicals Ar, for example, may be in various tautomeric forms, depending on the nature of the substituents.

Partially saturated five- or six-membered monoaza-, diaza- or triaza-heteroaryl radicals are, for example, dihydropyrrolyl, dihydroimidazolyl, dihydropyridinyl, dihydropyrimidinyl or tetrahydrotriazinyl. Examples of such radicals having oxo substituents are 2-oxo-1,2-dihydro-1-pyrrolinyl, 2-oxo-1,2-dihydro-4-pyrimidinyl or 5,6-dioxo-1,4,5,6-tetrahydro-1,2,4-triazin-3-yl. A completely saturated heteroaryl radical corresponds to heterocyclyl. Five- or six-membered monoaza- or diaza-heterocyclyl is, for example, pyrrolidinyl, piperidinyl, imidazolidinyl or piperazinyl. Examples of such radicals having oxo substituents are 2-pyrrolidinon-1-yl, 2-piperidinon-1-yl and, especially, 2-imidazolidinon-1-yl.

An acyl radical Ac may be the corresponding radical of a carboxylic acid, especially lower alkanoyl, also unsubstituted or substituted benzoyl, for example benzoyl containing lower alkyl, lower alkoxy, nitro and/or halogen, or of an organic sulphonic acid, especially lower alkylsulphonyl or unsubstituted or substituted phenylsulphonyl, for example phenylsulphonyl containing lower alkyl, lower alkoxy, nitro and/or halogen. Acyl radicals Ac are, however, especially acyl radicals of monoesters, and also of monoamides, of carbonic acid, such as, especially, unsubstituted or substituted, for example free or etherified, hydroxy, such as lower alkoxy, or unsubstituted or substituted amino, such as, for example, amino described above, and especially di-substituted amino, such as di-lower alkylamino, N-lower alkyl-N-phenyl-lower alkylamino, or lower alkyleneamino optionally interrupted by oxygen or sulphur or by unsubstituted or substituted, for example lower alkyl-substituted, nitrogen, or lower alkoxycarbonyl containing a phenyl, thienyl, furyl, pyrryl or pyridyl radical each of which is unsubstituted or substituted, for example, by lower alkyl, lower alkoxy, nitro and/or by halogen, also lower alkenyloxy- or lower alkynyloxy-carbonyl, but also N-unsubstituted or N-mono- or N,N-di-substituted carbamoyl, such as N-lower alkylcarbamoyl, N,N-di-lower alkylcarbamoyl, N-hydroxycarbamoyl, or N,N-lower alkylenecarbamoyl that is optionally interrupted in the lower alkylene moiety by oxygen or sulphur or by unsubstituted or substituted, for example lower alkyl-substituted, nitrogen. Furthermore, acyl radicals Ac also include acyl radicals of cyclic carbonic acid derivatives, such as, for example, 5-tetrazolyl or unsubstituted or lower alkyl- or phenyl-substituted 4,5-dihydro-2-oxazolyl or 5,6-dihydro-4H-1,3-oxazin-2-yl.

Alkyl preferably contains from 1 to 12 carbon atoms, for example n-decyl, and is especially lower alkyl. Lower alkyl is, for example, methyl, ethyl, n-propyl, isopropyl, n-butyl, isobutyl, sec.-butyl or tert.-butyl, also n-pentyl, isopentyl, neopentyl, n-hexyl, isohexyl or n-heptyl.

A substituted lower alkyl radical $R_1$ contains as substituent, for example, unsubstituted or, especially, mono- or di-substituted amino, such as lower alkylamino, di-lower alkylamino, N-lower alkyl-N-phenyl-lower alkylamino, or lower alkyleneamino optionally interrupted by oxygen or sulphur or by nitrogen that is unsubstituted or substituted, for example, by lower alkyl or lower alkanoyl, such a substituent preferably being separated from the ring nitrogen atom by at least 2 carbon atoms. Lower alkyl $R_1$ may also be substituted, for example, by carboxy or functionally modified carboxy, for example carboxymethyl, or by lower alkoxy, the preferred type of lower alkoxy being that which is itself substituted by lower alkoxy, for example 2-methoxyethoxymethyl, or it may be substituted by phenyl which for its part optionally contains lower alkyl, lower alkoxy, halogen and/or nitro as substituent(s), for example benzyl, or by N-pyrrolyl, N-imidazolyl, N-pyrazolyl, N-indolyl or N-isoindolyl, for example N-imidazolylmethyl.

Functionally modified carboxy is, for example, esterified carboxy, for example lower alkoxycarbonyl, or amidated carboxy, such as, for example, carbamoyl, N-lower alkylcarbamoyl or N,N-di-lower alkylcarbamoyl, or cyano. Functionally modified carboxy as $R_2$ and $R_3$ is preferably cyano.

In the case of an amino-lower alkyl radical $R_5$ that is substituted by functionally modified carboxy, the latter is preferably carbamoyl or C-amidino [—C(═N-H)—NH$_2$].

Phenyl-lower alkyl is, for example, benzyl or 1- or 2-phenylethyl. It may be substituted in the phenyl ring, for example, by free or etherified hydroxy, lower alkyl, nitro, amino, lower alkylamino, di-lower alkylamino, lower alkanoylamino and/or by halogen.

Lower alkylene contains, for example, from two to seven, especially from three to five, chain carbon atoms and is, inter alia, 1,3-propylene or 1,4-butylene. Lower alkylene in which a carbon atom is replaced by a hetero atom is, for example, oxa-, thia- or aza-lower alkylene. Lower alkylene or aza-, oxa- or thia-lower alkylene, formed by the radicals $R_8$ and $R_9$ together, is preferably $C_2$–$C_7$-lower alkylene, $C_3$–$C_4$-aza-, $C_3$–$C_4$-oxa- or $C_3$–$C_4$-thia-lower alkylene, especially $C_4$–$C_5$-lower alkylene, $C_4$-oxa- or $C_4$-aza-lower alkylene, especially 1,5-pentylene, 3-oxa- or 3-aza-1,5-pentylene and more especially 3-aza-1,5-pentylene.

Lower alkylene or aza-, oxa- or thia-lower alkylene, formed by the radicals $R_5$ and $R_6$ together, is preferably lower alkylene having from 2 to 5 chain carbon atoms, and aza-, oxa- or thia-lower alkylene each having 3 or 4 chain carbon atoms, especially $C_2$-$C_5$-lower alkylene or $C_4$-aza-lower alkylene and especially 1,5-pentylene.

Lower alkylene or aza-, oxa- or thia-lower alkylene, formed by the radicals $R_4$ and $R_5$ together, is preferably $C_3$-$C_5$-lower alkylene, $C_2$-$C_4$-oxa- or $C_2$-$C_4$-thia-lower alkylene, especially 1,3-propylene, 2-oxa- or 2-thia-1,3-propylene and especially 1,3-propylene.

Lower alkylene in which a carbon atom is optionally replaced by a hetero atom and which is formed by the radicals $R_1$ and $R_2$ together or $R_1$ and $R_3$ together is preferably $C_3$-$C_5$-lower alkylene in which the carbon atom bonded directly to the $C_2$- or $C_6$-carbon atom of the 1,4-dihydropyridine ring is optionally replaced by an oxygen or sulphur atom or by a nitrogen atom that is substituted by hydrogen or lower alkyl, especially $C_3$-$C_5$-lower alkylene or 3-oxa-, 3-thia- or 3-aza-1,3-propylene (the numbering of the carbon atoms beginning at the nitrogen atom), and more especially 1,2-ethylene, 1,3-propylene or 1,4-butylene.

Lower alkylene and oxa-, thia- and aza-lower alkylene radicals may be substituted, for example, by hydroxy, lower alkoxy, amino, lower alkylamino, dilower alkylamino, halogen, carboxy and/or by functionally modified carboxy, and at the aza-nitrogen atom also by lower alkanoyl, phenyl or phenyl-lower alkyl or especially by lower alkyl. Radicals, such as, for example, $C_3$-$C_4$-aza-, $C_4$-oxa- or $C_3$-$C_4$-thia-lower alkylene contain the number of carbon atoms indicated and, in addition, the hetero atom indicated.

Naphthyl may be, for example, 1- or 2-naphthyl.

Pyrryl is, for example, 2- or 3-pyrryl, pyrazolyl, for example 3- or 4-pyrazolyl, imidazolyl, for example 2- or 4-imidazolyl, triazolyl, for example 1,3,5-1H-triazol-2-yl or 1,3,4-triazol-2-yl, and tetrazolyl, for example 1,2,3,4-1H-tetrazol-5-yl, while furyl is 2- or 3-furyl and thienyl is 2- or 3-thienyl. Isoxazolyl is, for example, 3-isoxazolyl, oxazolyl, for example 2- or 4-oxazolyl, oxadiazolyl, for example 1,3,4-oxadiazol-2-yl, isothiazolyl, for example 3-isothiazolyl, thiazolyl, for example 2- or 4-thiazolyl, and thiadiazolyl, for example 1,3,4-thiadiazol-2-yl. Benzoxadiazolyl and benzothiadiazolyl are preferably 2,1,3-benzoxadiazol-4-yl and 2,1,3-benzothiadiazol-4-yl.

Pyridyl is 2-, 3- or 4-pyridyl, pyridazinyl is, for example, 3-pyridazinyl, pyrimidinyl is 2-, 4- or 5-pyrimidinyl, pyrazinyl is 2-pyrazinyl, and triazinyl is, for example, 1,3,5-triazin-2-yl.

Indolyl is, for example, 2-, 3- or 5-indolyl, isoindolyl, for example 1-isoindolyl, benzimidazolyl, for example 2- or 5-benzimidazolyl, benzofuranyl, for example 2- or 3-benzofuranyl, benzothienyl, for example 3-benzothienyl, benzothiazolyl, for example 2-benzothiazolyl, quinolinyl, for example 2- or 4-quinolinyl, and isoquinolinyl, for example 1-isoquinolinyl.

Lower alkenyl is, for example, allyl or methallyl, and lower alkynyl is, for example, propargyl.

Cycloalkyl preferably has from 5 to 7 ring carbon atoms and is, for example, cyclopentyl or cyclohexyl, while cycloalkyl-lower alkyl may be, for example, cyclopropylmethyl, cyclopentylmethyl or cyclohexylmethyl.

Etherified hydroxy is especially lower alkoxy, also, for example, phenyl-lower alkoxy, aryloxy or heteroaryloxy.

Acyloxy is, for example, hydroxy that is substituted by one of the acyl radicals Ac defined above, preferably benzoyloxy which is optionally substituted by hydroxy, lower alkoxy, halogen, lower alkyl and/or nitro, and is especially lower alkanoyloxy.

Lower alkoxy is, for example, methoxy, ethoxy, n-propoxy, isopropoxy, n-butoxy, isobutoxy or tert.-butoxy.

In a lower alkoxy-lower alkoxy radical, the terminal lower alkoxy group is preferably separated from the linking carbon atom by more than one carbon atom; such radicals are, for example, 2-methoxyethoxy or 2-ethoxyethoxy.

Lower alkenyloxy is, for example, allyloxy or methallyloxy, and halo-lower alkenyloxy, which may contain one or more halogen atoms, the latter preferably having an atomic number of up to and including 35 and being especially fluorine and chlorine, is, for example, 1,2-dichlorovinyloxy.

In a halo-lower alkoxy radical there may be one or more halogen atoms present which preferably have an atomic number of up to and including 35 and are especially fluorine or chlorine; such radicals are, for example, 1,1,2-trifluoro-2-chloroethoxy or, preferably, difluoromethoxy.

Lower alkynyloxy is, for example, propargyloxy while lower alkylenedioxy is, for example, methylenedioxy or ethylenedioxy.

Lower alkanoyloxy is, for example, acetoxy, propionyloxy or pivaloyloxy.

Halo-substituted lower alkyl is, for example, trifluoromethyl, 1,1,2-trifluoro-2-chloroethyl or chloromethyl.

Halogen preferably has an atomic number of up to and including 35 and is especially fluorine or chlorine, also bromine, but may also be iodine.

Lower alkoxycarbonyl is, for example, methoxycarbonyl, ethoxycarbonyl, n-propoxycarbonyl, isopropoxycarbonyl, n-butoxycarbonyl, isobutoxycarbonyl or tert.-butoxycarbonyl.

N-lower alkylcarbamoyl is, for example, N-methylcarbamoyl or N-ethylcarbamoyl, while N,N-di-lower alkylcarbamoyl is, for example, N,N-dimethylcarbamoyl or N,N-diethylcarbamoyl.

Lower alkylamino is, for example, N-methylamino, N-ethylamino, N-n-propylamino or N-isopropylamino.

Di-lower alkylamino is, for example, N,N-dimethylamino, N-ethyl-N-methylamino or N,N-diethylamino, while N-lower alkyl-N-phenyl-lower alkylamino is, for example, N-benzyl-N-methylamino or N-methyl-N-(2-phenylethyl)-amino.

Lower alkyleneamino contains, for example, from 2 to 7, preferably 4 or 5, ring carbon atoms and is, for example, pyrrolidino or piperidino, while oxa-lower alkyleneamino may be, for example, morpholino, such as 4-morpholino (3-oxa-1,5-pentyleneamino), thia-lower alkyleneamino, for example thiomorpholino, such as 4-thiomorpholino, and optionally aza-substituted aza-lower alkyleneamino may be, for example, piperazino, such as 1-piperazino (3-aza-1,5-pentyleneamino), 4-methylpiperazino, 4-phenylpiperazino, 4-benzylpiperazino or 4-(2-phenylethyl)-piperazino.

Acylamino is, for example, amino substituted by one of the acyl radicals Ac defined above, preferably benzoylamino which is optionally substituted by hydroxy, lower alkoxy, halogen, lower alkyl and/or nitro, and is especially lower alkanoylamino.

Lower alkanoylamino is, for example, acetylamino or propionylamino.

Acyl as such is, for example, one of the acyl radicals Ac defined above, preferably benzoyl which is optionally substituted in the manner indicated for benzoylamino, and is especially lower alkanoyl, for example formyl, acetyl, propionyl or pivaloyl. Further preferred acyl radicals are furanylcarbonyl, thienylcarbonyl, pyrrylcarbonyl or pyridinylcarbonyl, and especially furan-2-ylcarbonyl.

Etherified mercapto is especially lower alkylthio but also, for example, phenylthio. Oxidised etherified mercapto is preferably lower alkylsulphinyl or lower alkylsulphonyl. Lower alkylthio is, for example, methylthio, ethylthio, n-propylthio or isopropylthio, while lower alkylsulphinyl is, for example, methylsulphinyl, and lower alkylsulphonyl is, for example, methylsulphonyl or ethylsulphonyl.

In an amino-lower alkyl group $R_1$, amino is preferably separated from the linking carbon atom by at least two carbon atoms; such radicals are especially 2-di-substituted amino-lower alkyl, such as 2-di-lower alkylaminoethyl, for example 2-dimethylaminoethyl or 2-diethylaminoethyl, 2-lower alkyleneaminoethyl, for example 2-pyrrolidinoethyl or 2-piperidinoethyl, 2-(4-morpholino)-ethyl, or 2-(4-lower alkylpiperazino)ethyl, for example 2-(4-methylpiperazino)-ethyl.

In a substituted lower alkoxycarbonyl group, the substituent is usually separated from the oxygen atom by at least 2, preferably by 2 or 3, carbon atoms. Such radicals are, for example, hydroxy-lower alkoxycarbonyl, such as 2-hydroxyethoxycarbonyl or 2,3-dihydroxypropoxycarbonyl, lower alkoxy-lower alkoxycarbonyl, for example 2-methoxyethoxycarbonyl, di-lower alkylamino-lower alkoxycarbonyl, for example 2-dimethylaminoethoxycarbonyl, 2-diethylaminoethoxycarbonyl or 3-dimethylaminopropoxycarbonyl, lower alkyleneamino-lower alkoxycarbonyl, for example 2-pyrrolidinoethoxycarbonyl or 2-piperidinoethoxycarbonyl, morpholino-lower alkoxycarbonyl, for example 2-(4-morpholino)-ethoxycarbonyl, or 4-lower alkylpiperazino-lower alkoxycarbonyl, for example 2-(4-methylpiperazino)-ethoxycarbonyl.

Phenyl-lower alkoxycarbonyl is, for example, benzyloxycarbonyl or 2-phenylethoxycarbonyl.

N,N-lower alkylenecarbamoyl is, for example, pyrrolidinocarbonyl or piperidinocarbonyl, corresponding radicals in which the lower alkylene moiety is interrupted by oxygen, sulphur or unsubstituted or substituted nitrogen being, for example, 4-morpholinocarbonyl, 4-thiomorpholinocarbonyl, 1-piperazinocarbonyl or 4-methyl-1-piperazinocarbonyl.

Salts of compounds according to the invention are especially pharmaceutically acceptable non-toxic salts, such as those of compounds of the formula I having acidic groups, for example having a free carboxy or sulpho group. Such salts are especially metal or ammonium salts, such as alkali metal and alkaline earth metal salts, for example sodium, potassium, magnesium or calcium salts, and also ammonium salts with ammonia or suitable organic amines, there being suitable for the salt formation especially aliphatic, cycloaliphatic, cycloaliphatic-aliphatic or araliphatic primary, secondary or tertiary mono-, di- or polyamines and also heterocyclic bases: such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, and also bases of the pyridine type, for example pyridine, collidine or quinoline. Compounds of the formula I having basic groups can form acid addition salts, for example, with inorganic acids, such as hydrochloric acid, sulphuric acid or phosphoric acid, or with suitable organic carboxylic or sulphonic acids, for example trifluoroacetic acid, and also with amino acids, such as arginine and lysine. If several acidic or basic groups are present, mono- or poly-salts can be formed. Compounds of the formula I having an acidic group, for example a free carboxy group, and a free basic group, for example an amino group, may also be in the form of internal salts, that is to say in zwitterionic form, or one part of the molecule may be in the form of an internal salt and another part may be in the form of a normal salt.

For isolation or purification it is also possible to use pharmaceutically unacceptable salts. Only the pharmaceutically acceptable non-toxic salts are used therapeutically and these are therefore preferred.

The compounds of the formula I and salts of such compounds having salt-forming properties have valuable pharmacological properties. They exhibit, especially, strong antihypertensive and hypotensive action which can be demonstrated, for example, in doses of from approximately 0.3 mg/kg p.o. upwards in conscious renally hypertonic rats using the test procedure described by Byrom and Wilson, J. Physiol. (London), Vol. 93, p. 301 (1938), Gerold et al., Helv. Physiol. Pharmacol. Acta, Vol. 24, p. 58 (1966) and Goldblatt et al., J. Exptl. Med., Vol. 59, p. 347 (1934). The blood pressure-reducing action can also be demonstrated, for example, in narcotised cats by the intravenous administration of doses of from approximately 0.001 mg/kg upwards. In addition, the compounds have long-lasting pharmacological action, for example a long-lasting hypotensive or vasodilative action which can be demonstrated, for example, in conscious dogs and in narcotised dogs by the intravenous administration of doses of from approximately 0.01 mg/kg upwards. The compounds of the formula I are also distinguished by the fact that they have negatively inotropic and negatively chronotropic effects; the former can be demonstrated, for example, in vitro by the inhibition of the contracting force of the isolated left atrium of guinea pigs stimulated at a constant frequency in a concentration of from approximately 10 nmol/l upwards, and the latter can be demonstrated in the spontaneously beating right atrium of guinea pigs in a concentration of from approximately 1 nmol/l upwards. The compounds of the formula I are distinguished by having only weak negatively inotropic effects relative to the negatively chronotropic action. Furthermore, as is generally the case with calcium antagonists, the compounds of the formula I cause an increase in the heart rate, for example in narcotised dogs, as a result of reflex cardiostimulation but this increase is delayed and limited. In narcotised rats, the heart rate is reduced by the administration of compounds of the formula I in spite of an increase in the activity of the sympathetic nervous system.

The compounds of the formula I also have a dilative action on the coronary vessels as can be demonstrated, for example, in the isolated, perfused hearts of guinea pigs according to Langendorff in concentrations of from approximately 0.1 nmol/1 upwards. It should be emphasised that the compounds of the formula I have only weak negatively inotropic effects relative to the dilative action on the coronary vessels. The affinity of the compounds for calcium channels can be demonstrated in vitro in the nitrendipine receptor binding test. $^3$H-nitrendipine is bound specifically by membrane preparations of guinea pig hearts. The IC$_{50}$ values which indicate the concentration of test compound necessary to reduce by 50% the specific binding of $^3$H-nitrendipine are, in the case of the compounds according to the invention, approximately 0.1 nmol/1 or above. In addition, electrophysiological tests on compounds of the formula I, for example the recording of the intercellular leakage of the action potential in the isolated papillary muscle of guinea pig hearts, point to a strong inhibition of the Ca$^{2+}$ion influx. Thus, for example, in a papillary muscle preparation partially depolarised by K$^+$ions, in concentrations of 10 nmol/1 or less, a 50% inhibition of the "slow potential" occurs. In tests carried out on a non-depolarised preparation, compounds of the formula I prolong to a remarkable extent the duration of the action potential in concentrations of from 10 nmol/1 upwards, possibly as a result of an additional action on the potassium outflow. Furthermore, in vitro in the isolated perfused mesenteric vessel bed of rats, the compounds of the formula I preferentially inhibit vasoconstriction induced by potassium or calcium ions (from approximately 0.1 nmol/1 upwards) over vasoconstriction induced by noradrenaline (from approximately 10 nmol/1 upwards). The compounds of the formula I are also distinguished by the relatively rapid onset of the pharmacological actions, by chemical resistance and, compared with their cardiovascular actions, a relatively low toxicity.

The compounds of the formula I and salts of such compounds having salt-forming properties can therefore be used, for example, as antihypertensive agents and coronary dilators for the treatment of cardiovascular disorders, such as, especially, *Angina pectoris* and hypertonia, also, for example, arrhythmia, cerebral and peripheral circulatory disorders, pulmonary hypertonia, migraines, vascular constrictions or cardiac insufficiency and other indications, such as, for example, arteriosclerosis, spasms of the smooth musculature, such as bronchi, uterus, intestines etc., or general functional disorders of the brain. The novel compounds are, however, also valuable intermediates for the manufacture of other compounds, especially pharmaceutically active compounds.

The invention relates especially to compounds of the formula I in which n represents 1, 2 or 3, Ar represents a monocyclic or bicyclic carbocyclic aryl radical or a five- or six-membered monocyclic heteroaryl radical which contains as ring members from one up to and including four ring nitrogen atoms, one ring oxygen or ring sulphur atom, or one or two ring nitrogen atoms together with one ring oxygen atom or one ring sulphur atom and which optionally contains a fused-on benzo ring, and is especially phenyl, naphthyl, pyrryl, pyrazolyl, imidazolyl, triazolyl, tetrazolyl, furyl, thienyl, isoxazolyl, oxazolyl, oxadiazolyl, isothiazolyl, thiazolyl, thiadiazolyl, pyridyl, pyridazinyl, pyrimidinyl, pyrazinyl, triazinyl, indolyl, isoindolyl, benzoxadiazolyl, benzothiadiazolyl, benzimidazolyl, benzofuranyl, benzothienyl, quinolinyl or isoquinolinyl, it being possible for ring carbon atoms in these radicals to be optionally substituted by lower alkyl, lower alkenyl, lower alkynyl, lower alkylene, cycloalkyl, phenyl, phenyl-lower alkyl, phenyl-lower alkoxy and/or by phenyl-lower alkylthio (it being optionally possible for lower alkyl, phenyl, phenyl-lower alkyl, phenyl-lower alkoxy and/or phenyl-lower alkylthio to contain as substituent(s) hydroxy, lower alkoxy, halo-lower alkoxy, lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkylcarbamoyl and/or cyano, and for the cyclic radicals also to contain as substituent lower alkyl which may itself be substituted as indicated) and/or by hydroxy, lower alkoxy, halo-lower alkoxy, lower alkenyloxy, lower alkynyloxy, lower alkylenedioxy, lower alkanoyloxy, halogen, nitro, amino, lower alkylamino, di-lower alkylamino, N-lower alkyl-N-phenyl-lower alkylamino, lower alkyleneamino, oxa-lower alkyleneamino, thia-lower alkyleneamino and/or aza-lower alkyleneamino, (in which the aza-nitrogen atom may be substituted by lower alkyl, phenyl or phenyl-lower alkyl, which substituents may contain hydroxy, lower alkoxy, halo-lower alkoxy, lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkylcarbamoyl and/or cyano as substituent(s), and/or by lower alkanoylamino, azido, carboxy, lower alkoxycarbonyl, carbamoyl, N-lower alkylcarbamoyl, N,N-di-lower alkylcarbamoyl, cyano, sulpho, aminosulphonyl, lower alkylthio, lower alkylsulphinyl and/or by lower alkylsulphonyl, and/or for ring nitrogen atoms in these radicals to be optionally substituted by lower alkoxycarbonyl or by lower alkyl which may optionally contain hydroxy, lower alkoxy, halo-lower alkoxy, lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkylcarbamoyl or cyano as substituent, or by hydroxy or oxido, the radical Ac represents lower alkanoyl, benzoyl that is unsubstituted or substituted by lower alkyl, lower alkoxy, nitro and/or by halogen, lower alkylsulphonyl, phenylsulphonyl that is unsubstituted or substituted by lower alkyl, lower alkoxy, nitro and/or by halogen, lower alkoxycarbonyl, hydroxy-lower alkoxycarbonyl, lower alkoxy-lower alkoxycarbonyl, amino-lower alkoxycarbonyl, lower alkylamino-lower alkoxycarbonyl, N,N-di-lower alkylamino-lower alkoxycarbonyl, N-lower alkyl-N-phenyl-lower alkylamino-lower alkoxycarbonyl, N,N-lower alkyleneamino-lower alkoxycarbonyl, morpholino-lower alkoxycarbonyl, thiomorpholino-lower alkoxycarbonyl, piperazino-lower alkoxycarbonyl, 4-lower alkyl-piperazino-lower alkoxycarbonyl, phenyl-, thienyl-, furyl-, pyrryl- or pyridyl-lower alkoxycarbonyl that is unsubstituted or substituted by lower alkyl, lower alkoxy, nitro and/or by halogen, lower alkenyloxy- or lower alkynyloxy-carbonyl, carbamoyl, N-lower alkylcarbamoyl, N,N-di-lower alkylcarbamoyl, N-hydroxycarbamoyl, N,N-lower alkylenecarbamoyl, morpholinocarbonyl, thiomorpholinocarbonyl, piperazinocarbonyl, 4-lower alkylpiperazinocarbonyl, 5-tetrazolyl, or unsubstituted or lower alkyl- or phenyl-substituted 4,5-dihydro-2-oxazolyl or 5,6-dihydro-4H-1,3-oxazin-2-yl, Z represents a radical —OR$_7$ or —NR$_8$R$_9$, R$_1$ represents hydrogen; lower alkyl that is optionally substituted by lower alkylamino, di-lower alkylamino, lower alkyleneamino, morpholino, thiomorpholino, piperazino, which optionally contains lower alkyl or lower alkanoyl as substituent at a nitrogen atom, carboxy, functionally modified carboxy, lower alkoxy, lower alkoxy-lower alkoxy or phenyl, which itself optionally contains lower alkyl, lower alkoxy, halogen and/or nitro as substituent(s), or by N-pyrrolyl, N-imidazolyl, N-pyrazolyl, N-indolyl or by N-isoindolyl; phenyl which is optionally substituted in the same manner as a phenyl-lower alkyl radical $R_1$; hydroxy, lower alkoxy or phenyl-lower alkoxy, $R_2$ and $R_3$, independently of one another, each represents hydrogen, lower alkyl which is optionally substituted by hydroxy, by lower alkoxy, which optionally contains amino, lower alkylamino, di-lower alkylamino or acylamino as substituent, by acyloxy or by phenyl, or each represents formyl, di-lower alkyl acetal or dithioacetal, lower alkylene acetal or dithioacetal, functionally modified carboxy; phenyl which optionally contains as substituent(s) lower alkyl, hydroxy, lower alkoxy, lower alkylenedioxy, halogen, nitro, amino, lower alkylamino, di-lower alkylamino, lower alkanoylamino, carboxy, functionally modified carboxy and/or lower alkylthio; pyrryl, furyl, thienyl or pyridyl, these radicals optionally being substituted in the same manner as a phenyl radical $R_2$ or $R_3$; amino, lower alkylamino or di-lower alkylamino, $R_4$ represents hydrogen or lower alkyl, $R_5$ represents hydrogen, lower alkyl that is unsubstituted or substituted by free or etherified hydroxy, by free or etherified mercapto, which may optionally be oxidised, by carboxy, by functionally modified carboxy, by amino which itself optionally contains lower alkyl, carboxy, functionally modified carboxy or acyl as substituent, by a monocyclic or bicyclic carbocyclic aryl radical or by a five- or six-membered heteroaryl radical according to the above definition of Ar, or represents phenyl that is unsubstituted or substituted by free or etherified hydroxy, lower alkyl, nitro, amino, lower alkylamino, di-lower alkylamino, lower alkanoylamino and/or by halogen, or a monocyclic five- or six-membered heteroaryl radical according to the above definition of Ar that is optionally substituted in the same manner, $R_6$ represents hydrogen, lower alkyl, phenyl-lower alkyl that is unsubstituted or substituted by free or etherified hydroxy, lower alkyl, nitro, amino, lower alkylamino, di-lower alkylamino, lower alkanoylamino and/or by halogen, phenyl that is unsubstituted or substituted in the same manner as a phenyl-lower alkyl radical $R_6$, or a monocyclic five- or six-membered heteroaryl radical that is optionally substituted in the same manner, and $R_7$, $R_8$ and $R_9$, independently of one another, each represents hydrogen; alkyl that is optionally substituted by amino, lower alkylamino, di-lower alkylamino, lower alkyleneamino, oxa-, thia- or aza-lower alkyleneamino in which the aza-nitrogen atom optionally carries lower alkyl or lower alkanoyl as substituent, acylamino, free or etherified hydroxy or by a carbocyclic aryl radical or heteroaryl radical as defined above for the group Ar; or each represents a carbocyclic aryl radical or heteroaryl radical as defined above for the group Ar; in which $R_1$ and $R_2$ together or $R_1$ and $R_3$ together may represent $C_3$–$C_5$-lower alkylene in which the carbon atom bonded directly to the C2- or C6-carbon atom of the 1,4-dihydropyridine ring is optionally replaced by an oxygen or sulphur atom or by a nitrogen atom that is substituted by hydrogen or lower alkyl, in which $R_4$ and $R_5$ may together represent lower alkylene or oxa-, thia- or aza-lower alkylene each of which is unsubstituted or substituted by free or etherified hydroxy, amino, lower alkylamino, di-lower alkylamino and/or by halogen, and at the aza-nitrogen atom also by lower alkyl, in which $R_5$ and $R_6$ may together represent lower alkylene or aza-, oxa- or thia-lower alkylene, these radicals being optionally substituted at carbon atoms by free or etherified hydroxy, amino, lower alkylamino, di-lower alkylamino, halogen, carboxy and/or by functionally modified carboxy and at the azanitrogen atom optionally by lower alkyl, and in which $R_8$ and $R_9$ may together represent lower alkylene or aza-, oxa- or thia-lower alkylene, these radicals being optionally substituted at carbon atoms by free or etherified hydroxy, amino, lower alkylamino, di-lower alkylamino, halogen, carboxy, functionally modified carboxy or by a five- or six-membered monoaza-, diaza- or triaza-heteroaryl radical which is optionally completely or partially saturated and is optionally substituted at carbon atoms by oxo and optionally substituted at the aza-nitrogen atoms by lower alkyl or phenyl, which may itself contain lower alkyl, halogen, lower alkoxy and/or nitro as substituent(s); and being optionally substituted at the aza-nitrogen atom by lower alkyl which itself optionally contains a carbocyclic aryl radical or heteroaryl radical as defined above for the group Ar and/or free or etherified hydroxy, acyloxy, amino, lower alkylamino and/or di-lower alkylamino as substituent(s); by acyl or phenyl, which may itself contain lower alkyl, halogen, lower alkoxy and/or nitro as substituent(s), to optical isomers of compounds of the formula I, mixtures of these optical isomers, and salts of such compounds having salt-forming groups.

The invention relates more especially to compounds of the formula I in which n represents 1, 2 or 3, Ar represents phenyl which is optionally substituted by lower alkyl, phenyl, phenyl-lower alkyl, phenyl-lower alkoxy and/or by phenyl-lower alkylthio (it being possible for these radicals themselves to contain hydroxy, lower alkoxy, lower alkylenedioxy, halogen, carboxy, lower alkoxycarbonyl and/or cyano as substituent(s), and for the cyclic radicals also to contain lower alkyl as substituent) and/or by hydroxy, lower alkoxy, halo-lower alkoxy, lower alkylenedioxy, halogen, nitro, amino, lower alkylamino, di-lower alkylamino, lower alkanoylamino, carboxy, lower alkoxycarbonyl, carbamoyl, cyano, sulpho, aminosulphonyl, lower alkylthio, lower alkylsulphinyl and/or by lower alkylsulphonyl, or represents pyrryl, furyl, thienyl, pyridyl, benzoxadiazolyl or benzothiadiazolyl, which radicals are optionally substituted in the same manner as a phenyl radical Ar and contain as substituent(s) especially lower alkyl, lower alkoxy, halogen and/or phenyl which is optionally substituted by lower alkyl, lower alkoxy, halogen and/or by nitro, the radical Ac represents lower alkanoyl, lower alkylsulphonyl, lower alkoxycarbonyl, hydroxy-lower alkoxycarbonyl, lower alkoxy-lower alkoxycarbonyl, N,N-di-lower alkylamino-lower alkoxycarbonyl, N-lower alkyl-N-phenyl-lower alkylamino-lower alkoxycarbonyl, N,N-lower alkyleneamino-lower alkoxycarbonyl, (4-morpholino)-lower alkoxycarbonyl, lower alkenyloxy- or lower alkynyloxy-carbonyl, carbamoyl, N-lower alkylcarbamoyl, N,N-di-lower alkylcarbamoyl, N,N-lower alkylenecarbamoyl, 4-morpholinocarbonyl or 4-lower alkyl-1-piperazinocarbonyl, Z represents a radical —$OR_7$ or —$NR_8R_9$, $R_1$ represents hydrogen, lower alkyl, di-lower alkylamino-lower alkyl, lower alkyleneamino-lower alkyl, (4-morpholino)-lower alkyl, carboxy-lower alkyl, lower alkoxycarbonyl-lower alkyl or lower alkoxy-lower alkoxy-lower alkyl, wherein di-lower alkylamino, lower alkyleneamino and 4-morpholino are separated from the ring nitrogen atom by at least two carbon atoms, or represents phenyl-lower alkyl, phenyl, hydroxy or lower alkoxy, $R_2$ and $R_3$, independently of one another, each represents lower alkyl which is optionally substituted by hydroxy, by lower alkoxy, which optionally contains amino, lower alkylamino or di-lower alkylamino as substituent, by lower alkanoyloxy or by phenyl, or each represents formyl, di-lower alkyl acetal or dithioacetal, lower alkylene acetal or dithioacetal, cyano, phenyl, thienyl or amino, $R_4$ represents hydrogen or lower alkyl, $R_5$ represents hydrogen, lower alkyl that is unsubstituted or substituted by hydroxy, lower alkoxy, mercapto, lower alkylthio, carboxy, carbamoyl, amino, lower alkanoylamino, carbamoylamino, guanidino, phenyl, which may for its part be hydroxy- and/or halo-substituted, by imidazolyl or by indolyl, or represents phenyl that is unsubstituted or substituted by hydroxy, lower alkoxy, lower alkyl, nitro, amino, lower alkylamino, di-lower alkylamino and/or by halogen, or represents pyrryl, pyrazolyl, imidazolyl, triazolyl, tetrazolyl, furyl, thienyl, isoxazolyl, oxazolyl, oxadiazolyl, isothiazolyl, thiazolyl, thiadiazolyl, pyridyl, pyridazinyl, pyrimidinyl, pyrazinyl or triazinyl, each of which is unsubstituted or substituted as indicated for a phenyl radical $R_5$, $R_6$ represents hydrogen, lower alkyl, phenyl-lower alkyl, phenyl-lower alkyl that is unsubstituted or substituted by hydroxy, lower alkoxy, lower alkyl, nitro, amino, lower alkylamino, di-lower alkylamino and/or by halogen, or phenyl, pyrryl, pyrazolyl, imidazolyl, triazolyl, tetrazolyl, furyl, thienyl, isoxazolyl, oxazolyl, oxadiazolyl, isothiazolyl, thiazolyl, thiadiazolyl, pyridyl, pyridazinyl, pyrimidinyl, pyrazinyl or triazinyl, each of which is unsubstituted or substituted as indicated for a phenyl-lower alkyl radical $R_6$, and $R_7$, $R_8$ and $R_9$, independently of one another, each represents hydrogen, lower alkyl, or lower alkyl that is substituted by amino, lower alkylamino, di-lower alkylamino, lower alkyleneamino, oxa-, thia- or aza-lower alkyleneamino, in which the aza-nitrogen atom is optionally lower alkyl-substituted, lower alkanoylamino, hydroxy, lower alkoxy or by phenyl, which may be unsubstituted or may itself be substituted by amino, lower alkylamino, di-lower alkylamino, lower alkyleneamino, hydroxy, lower alkoxy, halogen and/or by nitro, or lower alkyl that is substituted by pyrryl, furyl, thienyl or by pyridyl, it being possible for these groups to be substituted in the same manner as phenyl, or each represents phenyl, pyrryl, furyl, thienyl or pyridyl, which groups may be substituted in the same manner as a phenyl-lower alkyl radical $R_7$, $R_8$ or $R_9$; in which $R_1$ and $R_2$ together or $R_1$ and $R_3$ together may represent $C_3$–$C_5$-lower alkylene in which the carbon atom bonded directly to the C2- or C6-carbon atom of the 1,4-dihydropyridine ring is optionally replaced by an oxygen or sulphur atom or by a nitrogen atom that is substituted by hydrogen or lower alkyl, in which $R_4$ and $R_5$ may together represent unsubstituted or hydroxy-substituted $C_3$–$C_5$-lower alkylene, $C_2$–$C_4$-oxa- or $C_2$–$C_4$-thia-lower alkylene, in which $R_5$ and $R_6$ may together represent lower alkylene having from 2 to 5 chain carbon atoms or aza-lower alkylene having 3 or 4 chain carbon atoms, which radicals may be unsubstituted or substituted by hydroxy, lower alkoxy, amino, lower alkylamino or by di-lower alkylamino, and in which $R_8$ and $R_9$ may together represent $C_2$–$C_7$-lower alkylene, $C_3$–$C_4$-aza-, $C_3$–$C_4$-oxa- or $C_3$–$C_4$-thia-lower alkylene, these radicals being optionally substituted at carbon atoms by hydroxy, lower alkoxy, amino, lower alkylamino, di-lower alkylamino or by five- or six-membered monoaza- or diaza-heterocyclyl which is optionally substituted at carbon atoms by oxo and optionally substituted at the aza-nitrogen atoms by lower alkyl or phenyl, which may itself contain lower alkyl, halogen, lower alkoxy and/or nitro as substituent(s); and being optionally substituted at the aza-nitrogen atom by lower alkyl (which may itself be substituted by phenyl, pyrryl, furyl, thienyl and/or by pyridyl, which radicals themselves optionally contain lower alkyl, hydroxy, lower alkoxy, halogen and/or nitro as substituent(s), and/or by hydroxy, lower alkoxy, lower alkanoyloxy, amino, lower alkylamino and/or by di-lower alkylamino) by benzoyl, lower alkanoyl, furanylcarbonyl, thienylcarbonyl, pyrrylcarbonyl, pyridinylcarbonyl or by phenyl, which may itself contain lower alkyl, halogen, lower alkoxy and/or nitro as substituent(s), to optical isomers of compounds of the formula I, mixtures of these optical isomers, and salts of such compounds having salt-forming groups.

The invention relates most especially to compounds of the formula I in which n represents 1 or 2, Ar represents phenyl, thienyl, furyl or benzoxadiazolyl, which groups are optionally mono-, di- or tri-substituted by lower alkyl, lower alkoxy, halo-lower alkoxy, phenyl-lower alkoxy, phenyl-lower alkylthio, lower alkylenedioxy, halogen, trifluoromethyl, nitro, lower alkanoylamino and/or by cyano, the radical Ac represents lower alkanoyl, lower alkylsulphonyl, lower alkoxycarbonyl, 2-lower alkoxy-lower alkoxycarbonyl, N,N-di-lower alkylamino-lower alkoxycarbonyl, N-lower alkyl-N-phenyl-lower alkylamino-lower alkoxycarbonyl, carbamoyl, N-lower alkylcarbamoyl, N,N-di-lower alkylcarbamoyl, N,N-lower alkylenecarbamoyl or 4-morpholinocarbonyl, Z represents a radical —$OR_7$ or —$NR_8R_9$, $R_1$ represents hydrogen, lower alkyl, 2-(di-lower alkylamino)-lower alkyl, 2-(lower alkyleneamino)-lower alkyl, 2-(4-morpholino)-lower alkyl, carboxy-lower alkyl or lower alkoxy-lower alkoxy-lower alkyl, $R_2$ and $R_3$, independently of one another, each represents lower alkyl, hydroxy-lower alkyl, cyano or amino, $R_4$ represents hydrogen or lower alkyl, $R_5$ represents hydrogen, lower alkyl that is unsubstituted or substituted by hydroxy, lower alkoxy, mercapto, lower alkylthio, carboxy, carbamoyl, amino, carbamoylamino, guanidino, phenyl, which may itself be hydroxy-substituted, or by imidazol-4-yl or indol-3-yl, or represents phenyl, thiazolyl, imidazolyl, furyl, thienyl, pyridyl or pyrimidinyl, which radicals are optionally substituted by hydroxy, lower alkoxy and/or by amino, $R_6$ represents hydrogen, lower alkyl, phenyl-lower alkyl, which is unsubstituted or substituted by hydroxy, lower alkoxy and/or by amino, or phenyl, thiazolyl, imidazolyl, furyl, thienyl, pyridyl or pyrimidinyl, which radicals are optionally substituted in the same manner as a phenyl-lower alkyl radical $R_6$, and $R_7$, $R_8$ and $R_9$, independently of one another, each represents hydrogen or lower alkyl that is unsubstituted or substituted by amino, lower alkylamino, di-lower alkylamino, lower alkyleneamino, oxa- or aza-lower alkyleneamino, in which the aza-nitrogen atom is optionally lower alkyl-substituted, hydroxy, lower alkoxy, phenyl, which may be unsubstituted or, for its part, amino-, hydroxy-, lower alkoxy- and/or halo-substituted, or by thienyl or pyridyl, which groups may be substituted in the same manner as phenyl; in which $R_4$ and $R_5$ may together represent $C_3$–$C_4$-lower alkylene, in which $R_5$ and $R_6$ may together represent $C_2$–$C_5$-lower alkylene or $C_4$-aza-lower alkylene and in which $R_8$ and $R_9$ may together represent $C_4$–$C_5$-lower alkylene which is optionally substituted by 2-imidazolidinon-1-yl, which may contain phenyl or lower alkyl as substituent in the 3-position, $C_4$-oxa- or $C_4$-aza-lower alkylene, in which the aza-nitrogen atom may be substituted by lower alkyl (which is itself unsubstituted or mono- or di-substituted by phenyl, which may contain lower alkyl, lower alkoxy, halogen and/or nitro as substituent(s), by thienyl and/or by pyridyl) or may be substituted by benzoyl, furanylcarbonyl, phenyl or by lower alkoxyphenyl, to optical isomers of compounds of the formula I, mixtures of these optical isomers, and pharmaceutically acceptable salts of such compounds having salt-forming groups.

The invention relates chiefly to compounds of the formula I in which n represents 1 or 2, Ar represents phenyl that is unsubstituted or mono- or di-substituted by lower alkyl, lower alkoxy, halo-lower alkoxy, benzyloxy, benzylthio, halogen, trifluoromethyl, nitro and/or by cyano, or represents 2- or 3-thienyl but also 2,1,3-benzoxadiazol-4-yl, the radical Ac represents lower alkylsulphonyl or lower alkoxycarbonyl, Z represents a radical —$OR_7$ or —$NR_8R_9$, $R_1$ represents hydrogen, and also 2-(4-morpholino)-ethyl, $R_2$ represents lower alkyl, hydroxymethyl, cyano or amino, $R_3$ represents lower alkyl, $R_4$ represents hydrogen or lower alkyl, $R_5$ represents hydrogen, lower alkyl that is unsubstituted or substituted by phenyl, which may itself be hydroxy-substituted, or represents phenyl or unsubstituted or amino-substituted thiazolyl, $R_6$ represents hydrogen, lower alkyl or phenyl, $R_7$ represents hydrogen, lower alkyl, or lower alkyl that is substituted by phenyl, amino, lower alkylamino, di-lower alkylamino, 4-morpholino, 1-piperazino, which may itself contain lower alkyl as substituent at the 4-nitrogen atom, or by lower alkoxy, $R_8$ and $R_9$, independently of one another, each represents hydrogen or lower alkyl that is unsubstituted or substituted by lower alkoxy, phenyl or by pyridyl; in which $R_4$ and $R_5$ may together represent 1,3-propylene, in which $R_5$ and $R_6$ may together represent 1,5-pentylene and in which $R_8$ and $R_9$ may together represent 1,5-pentylene, 3-(3-phenyl-2-imidazolidinon-1-yl)-1,5-pentylene, 3-(2-imidazolidinon-1-yl)-1,5-pentylene or 3-oxa- or 3-aza-1,5-pentylene, in which the aza-nitrogen atom is optionally substituted by lower alkyl, benzyl, diphenylmethyl, the radical benzyl or diphenylmethyl optionally containing halogen, lower alkyl and/or lower alkoxy as substituent(s), or by benzoyl, furanylcarbonyl, phenyl or by lower alkoxy-phenyl, to optical isomers of compounds of the formula I, mixtures of these optical isomers, and pharmaceutically acceptable salts of such compounds having salt-forming groups.

The invention relates first and foremost to compounds of the formula I in which n represents 1, Ar represents 2- or 3-nitrophenyl, 2- or 3-difluoromethoxyphenyl, 2- or 3-methylphenyl, 2- or 3-trifluoromethylphenyl, 2,3-dimethylphenyl, 2,3-dichlorophenyl, 2- or 3-benzyloxyphenyl or 2- or 3-benzylthiophenyl, Ac represents lower alkoxycarbonyl, Z represents a radical —$OR_7$ or —$NR_8R_9$, $R_1$ represents hydrogen, $R_2$ and $R_3$, independently of one another, each represents lower alkyl, $R_4$ represents hydrogen, $R_5$ represents lower alkyl or phenyl, $R_6$ represents hydrogen, $R_7$ represents lower alkyl that is unsubstituted or substituted by 4-morpholino, 1-piperazino or by 4-lower alkyl-1-piperazino, $R_8$ and $R_9$, independently of one another, each represents hydrogen or lower alkyl that is unsubstituted or substituted by phenyl or pyridyl; and in which $R_8$ and $R_9$ may together represent 3-aza-1,5-pentylene in which the aza-nitrogen atom is optionally substituted by benzyl or diphenylmethyl, to optical isomers of compounds of the formula I, mixtures of these optical isomers, and pharmaceutically acceptable salts of such compounds having salt-forming groups.

Preferred are compounds of the formula I in which Ar represents 2- or 3-nitrophenyl, 2- or 3-difluoromethoxyphenyl, 2- or 3-methylphenyl, 2- or 3-trifluoromethylphenyl, 2,3-dimethylphenyl, 2,3-dichlorophenyl, 2- or 3-benzyloxyphenyl or 2- or 3-benzylthiophenyl, but also 2,1,3-benzoxadiazol-4-yl. Of particular importance are compounds of the formula I in which Ar represents 2- or 3-nitrophenyl, and very especially 3-nitrophenyl. A further preferred embodiment of the invention are compounds of the formula I in which Ac represents lower alkoxycarbonyl, 2-lower alkoxy-lower alkoxycarbonyl, lower alkylsulphonyl, carbamoyl, N-alkyl- or N,N-dialkyl-carbamoyl, especially lower alkoxycarbonyl, 2-lower alkoxy-lower alkoxycarbonyl, carbamoyl, N-alkyl- or N,N-dialkylcarbamoyl, and more especially lower alkoxycarbonyl. Emphasis should be placed on compounds of the formula I in which Z represents a radical —$NR_8R_9$. Compounds of the formula I in which Z represents a radical —$OR_7$ are preferred. Also preferred are compounds of the formula I in which $R_1$ represents hydrogen. Likewise preferred are compounds of the formula I in which $R_2$ and/or $R_3$ represent(s) lower alkyl, hydroxy-lower alkyl, especially hydroxymethyl, cyano or amino. Emphasis should be placed on compounds of the formula I in which one of the radicals $R_2$ and $R_3$ is lower alkyl and the other is one of the radicals indicated for $R_2$ and $R_3$ under formula I, especially lower alkyl, hydroxy-lower alkyl, cyano or amino. Of particular interest are compounds of the formula I in which $R_2$ represents lower alkyl, especially methyl or ethyl, and more especially methyl. Also preferred are compounds of the formula I in which $R_3$ represents lower alkyl, especially methyl or ethyl, and more especially methyl. Of particular importance are compounds of the formula I in which $R_4$ represents hydrogen. Preferred are compounds of the formula I in which $R_5$ represents lower alkyl or phenyl, especially $C_3$–$C_4$-lower alkyl or phenyl, more especially isopropyl, sec.-butyl (1-methylpropyl) or phenyl, and first and foremost isopropyl. Emphasis should also be placed on compounds of the formula I in which $R_6$ represents hydrogen. Likewise preferred are compounds of the formula I in which $R_7$ represents lower alkyl that is unsubstituted or substituted by 4-morpholino or by 4-lower alkyl-1-piperazino, and especially $C_2$–$C_4$-lower alkyl. Emphasis should also be placed on compounds of the formula I in which $R_8$ and $R_9$ together represent 3-aza-1,5-pentylene in which the aza-nitrogen atom is substituted by benzyl or diphenylmethyl.

The invention relates especially to the specific compounds described in the Examples. Furthermore, it relates to all optical isomers as well as to any mixture of optical isomers, e.g. mixtures consisting of all optical isomers, of the specific compounds described in the Examples.

The compounds of the formula I and salts of such compounds having salt-forming properties can be manufactured in a manner known per se, for example as follows:

(a) a compound of the formula II

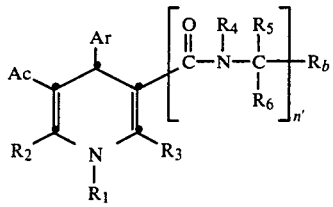

(II)

in which n' represents 0, 1 or 2 and $R_b$ represents an optionally activated carboxy group, with the proviso that $R_b$ is other than a radical C(=O)—Z when n' represents 1 or 2, is reacted with a compound of the formula III

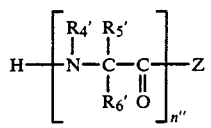

(III)

in which n" represents 1, 2 or 3, and $R_4'$, $R_5'$ and $T_6'$ have the meanings given for $R_4$, $R_5$ and $R_6$ under formula I, but can be other than the radicals $R_4$, $R_5$ and $R_6$ in formula II, with the proviso that the sum of n' and n" is not greater than 3, or (a') in a compound of the formula IIa

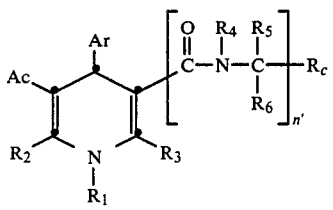

(IIa)

in which n' represents 1, 2 or 3 and $R_c$ represents a group that can be converted into the radical C(=O)—Z, this group is converted into the radical C(=O)—Z, or (b) a compound of the formula IV, or a reactive derivative thereof, is reacted with a compound of the formula V, or with a tautomer thereof, and with a compound of the formula VI

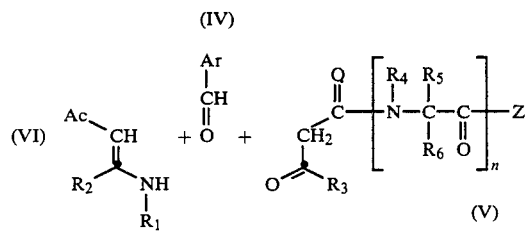

(b') in exactly the same manner as in process (b), a compound of the formula Va is reacted with a compound of the formula VI,

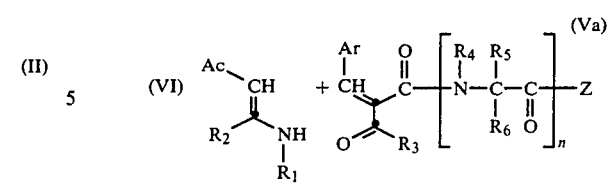

or
(c) a compound of the formula VII

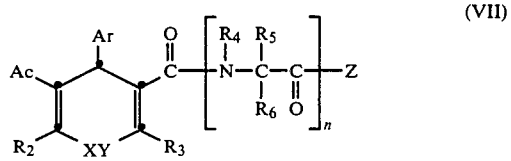

(VII)

in which one of the radicals X and Y is a group of the formula —NH—$R_1$ and the other is hydroxy, or both are a group of the formula —NH—$R_1$, or a tautomer thereof, or a corresponding tautomeric mixture, is cyclised, or (d) a compound of the formula Ar—CHO (IV), or a reactive functional derivative thereof, is reacted with a compound of the formula VIII

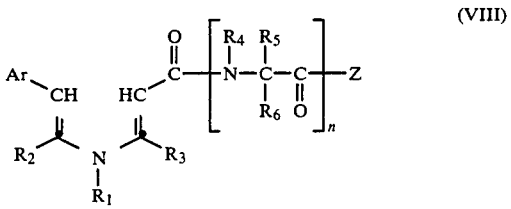

(VIII)

or with a tautomer thereof or with a corresponding tautomeric mixture, or (e) in a compound of the formula IX

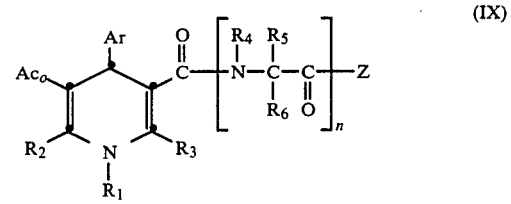

(IX)

in which $Ac_o$ represents a radical that can be converted into the group Ac, this radical is converted into the group Ac, wherein in the above starting materials of the formulae II to IX, IIa and Va, which can also be used in the form of their salts if they have salt-forming properties, the symbols n, Ar, Ac, $R_1$, $R_2$, $R_3$, $R_4$, $R_5$, $R_6$ and Z have the meanings given under formula I, and, if desired, a resulting compound of the formula I is converted into a different compound of the formula I, and/or, if desired, a resulting salt is converted into the free compound or into a different salt, and/or, if desired, a resulting free compound of the formula I having salt-forming properties is converted into a salt, and/or, if desired, a resulting mixture of isomers or racemates is separated into the individual isomers or racemates, and/or, if desired, resulting racemates are split into the optical antipodes.

In a compound of the formula II, $R_b$ is, for example, a free carboxy group or a carboxy group that has been activated for the purpose of linking an amide or peptide bond.

In order to carry out process variant (a), the carboxy group can be activated, for example, by conversion into an acid azide, anhydride, imidazolide or isoxazolide or into an activated ester, such as one of those mentioned below, or by reaction with a carbodiimide, such as N,N'-dicyclohexyl carbodiimide, optionally with the addition of N-hydroxysuccinimide, an unsubstituted or, for example, halo-, methyl- or methoxy-substituted 1-hydroxybenzotriazole or 4-hydroxybenzo-1,2,3-triazin-3-oxide (inter alia, cf. German Offenlegungsschrift 1 917 690, German Offenlegungsschrift 1 937 656, German Offenlegungsschrift 2 202 613), or especially with the addition of N-hydroxy-5-norbornene-2,3-dicarboximide, or by reaction with N,N'-carbonyldiimidazole. It can also be activated by converting it first, for example with trimethylsilyl chloride, into the corresponding trimethylsilyl ester and then with a suitable halogenating agent, for example thionyl chloride, into the corresponding acid halide, especially the acid chloride.

Suitable for the formation of activated esters that are mentioned above are, for example, phenols and thiophenols that are optionally substituted by electron-attracting substituents, such as phenol, thiophenol, thiocresol, p-nitrothiophenol, 2,4,5- and 2,4,6-trichlorophenol, penta(fluoro or chloro)phenol, o- and p-nitrophenol, 2,4-dinitrophenol or p-cyanophenol, and also, for example, N-hydroxysuccinimide, N-hydroxyphthalimide and N-hydroxypiperidine.

In order to carry out process (a), a compound of the formula II and a compound of the formula III are subjected to a condensation reaction in a manner known per se.

The most common method of linking amide or peptide bonds is the carbodiimide method, and also the azide method, the activated esters method and the anhydride method, and also the Merrifield method, the N-carboxyanhydrides or N-thiocarboxyanhydrides method and the acid chloride method.

In an especially preferred method of manufacturing the compounds of the formula I, there is used as coupling method the carbodiimide method with N,N'-dicyclohexyl carbodiimide in the presence of 1-hydroxybenzotriazole. In this method, a compound of the formula II in which $R_b$ represents a free carboxy group is first converted by 1-hydroxybenzotriazole temporarily into the corresponding benzotriazol-1-yl ester which is then reacted, under the action of the above-mentioned carbodiimide, with a compound of the formula III, preferably one in which Z represents $OR_7$ and $R_7$ represents optionally substituted lower alkyl or in which Z represents $NR_8R_9$, to form a compound of the formula I.

The starting materials of the formula II and of the formula III can be used, independently of one another, in the form of racemates, racemic mixtures, optical isomers or in the form of mixtures of several optical isomers. For example, Chem. Pharm. Bull. 28, 2809–2812 (1980) describes the manufacture of optical isomers of the formula II from a racemic compound of the formula II.

Very many starting materials of the formula III (amino acids, di- and tri-peptides and their C-terminal optionally substituted lower alkyl esters) are known, both in the form of racemates, or racemic mixtures and in the form of optical isomers, and others can be manufactured analogously to the known starting materials.

Starting materials of the formula II in which n' represents 0 are known, for example from European Patent Application No. 11.706, and others can be manufactured analogously to the known starting materials. A starting material of the formula II in which n' represents 1 or 2 can be manufactured, for example, as follows: a compound of the formula II in which n' represents 0 is reacted with a compound of the formula IIIa

or with a compound of the formula IIIb

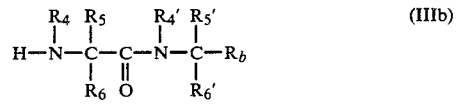

in which $R_b$ has the meaning given under formula II and $R_4$, $R_5$ and $R_6$ have the meanings given under formula I and $R_4'$, $R_5'$ and $R_6'$ have the meanings given for $R_4$, $R_5$ and $R_6$ under formula I but can be other than $R_4$, $R_5$ and $R_6$, in the same manner as described above for the manufacture of compounds of the formula I from a compound of the formula II and a compound of the formula III. Compounds of the formulae IIIa and IIIb are known; they are either identical with compounds of the formula III in which Z represents $OR_7$ and $R_7$ represents hydrogen and n'' represents 1 or 2, respectively, or can be manufactured from these same compounds according to the same activation methods as described above for compounds of the formula II.

The process variant (a') includes, inter alia, the conversion of compounds of the formula IIa in which $R_c$ represents, for example, a protected and/or functionally modified carboxy group into compounds of the formula I. A protected carboxy group should be understood as being a carboxy group protected by a protecting group such as customarily used in peptide chemistry. Such protecting groups can be readily removed, that is to say without undesired secondary reactions taking place, for example by solvolysis, reduction, photolysis or alternatively under physiological conditions, compounds of the formula I in which Z represents $OR_7$ and $R_7$ represents hydrogen generally being obtained.

Protecting groups of this type and the manner in which they are removed are described, for example, in "Protective Groups in Organic Chemistry", Plenum Press, London, New York, 1973, and also in "The Peptides", Vol. I, Schröder and Lübke, Academic Press, London, New York, 1965, and in "Methoden der organischen Chemie", Houben-Weyl, 4th Edition, Vol. 15/1, Georg Thieme Verlag, Stuttgart, 1974.

Thus, carboxy groups are protected, for example, by hydrazide formation or by esterification. Suitable for esterification are, for example, lower substituted alkanols, such as cyanomethanol, 2,2,2-trichloroethanol or benzoylmethanol. An especially advantageous category of substituted alkanols are ethanols that carry in the $\beta$-position a tri-substituted silyl group, such as a triphenylsilyl, dimethylbutylsilyl or, especially, trimethylsilyl group. As described, for example, in Belgian Pat. No. 851.576, these alcohols are especially suitable for protecting carboxy groups because, although the corresponding β-silylethyl esters, for example β-(trimethylsilyl)-ethyl ester, possess the stability of customary alkyl esters, they can be removed selectively under mild conditions by the action of reagents that yield fluoride ions, for example fluorides of quaternary organic bases, such as tetraethylammonium fluoride. Like the customary substituted alkyl esters, they can also, however, be removed by alkaline hydrolysis, for example by means of alkali metal hydroxides, carbonates or bicarbonates.

If in a compound of the formula IIa (or I) $R_c$ represents a functionally modified carboxy group, for example cyano, an imido ester, especially an imido-lower alkyl ester, an optionally substituted carbamoyl group or an acid halide, then this compound can be converted in a manner known per se, especially by hydrolysis in alkaline or acidic medium, into a compound of the formula I in which Z represents $OR_7$ and $R_7$ represents hydrogen, it also being possible in the former case to obtain a salt directly. A compound of the formula IIa in which $R_c$ represents cyano can also be converted in customary manner, for example by the addition of optionally substituted lower alkanols in the presence of an anhydrous acid, such as hydrogen chloride, and subsequent careful hydrolysis of the resulting imido ester, into a compound of the formula I in which $R_7$ represents optionally substituted lower alkyl; the same result can be obtained by reacting a compound of the formula IIa in which $R_c$ represents an acid halide with optionally substituted lower alkanols.

In this process variant, it is, however, also possible to use starting materials of the formula IIa in which $R_c$ represents, for example, formyl or a reactive derivative thereof, as defined below, hydroxymethyl or methyl; these starting materials can be converted by customary oxidation methods into compounds of the formula I, preferably those in which Z represents $OR_7$ and $R_7$ represents hydrogen.

Especially when carrying out process variant (a'), care must be taken that undesired secondary reactions, which could result in the conversion of additional groupings in the molecule, do not take place.

Starting materials of the formula IIa in which n' represents 1, 2 or 3 can be manufactured, for example, in a manner analogous to that described above for the compounds of the formula II in which n' represents 1 or 2, that is to say by reacting a compound of the formula II in which n' represents 0 or 1 with compounds that differ from those of the formulae IIIa and IIIb in that they contain $R_c$ instead of $R_b$.

Reactive functional derivatives of the aldehyde of the formula IV used as starting material in process variant (b), and also reactive functional derivatives of formyl groups in general, are, inter alia, the corresponding acetals, such as di-lower alkyl acetals, for example dimethyl or diethyl acetals, acylals, such as di-lower alkanoylacylals, for example diacetylacylals, or especially the corresponding dihalomethyl, for example dichloromethyl or dibromomethyl, compounds, also addition compounds, such as those with water or an alkali metal bisulphite, for example potassium bisulphite.

A variant of this process consists in first reacting a compound of the formula IV with a compound of the formula V, for example in the presence of an organic or inorganic base, for example a catalytic amount of piperidine, or preferably in the presence of an inorganic or organic acid, for example a mineral acid, such as, for example, hydrochloric acid, or, for example, p-toluenesulphonic acid, and allowing the resulting intermediate of the formula Va

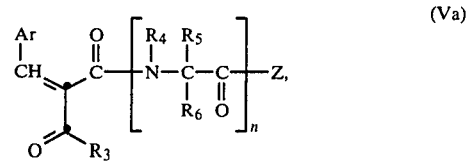

after isolating it or without isolating it, to react with a compound of the formula VI.

Starting materials of the formulae IV and VI are known, and others can be manufactured analogously to the known starting materials. A starting material of the formula V can be obtained in a manner known per se, for example by reacting a compound of the formula III, for example with diketene according to Pharm. Acta. Helv. 38, 616 (1963).

Normally, the starting materials of the formula VII used in process variant (c) are formed in situ and the cyclisation according to the process takes place under the reaction conditions used for the manufacture of the starting material. For example, the starting materials of the formula VII and, under the reaction conditions, generally also the corresponding end products of the formula I can be obtained by (ca) reacting a compound of the formula IV or a reactive functional derivative thereof defined above with a compound of the formula

a compound of the formula V and a compound of the formula $R_1$-$NH_2$ (X), or (cb) by reacting a compound of the formula IV or a reactive functional derivative thereof with a compound of the formula

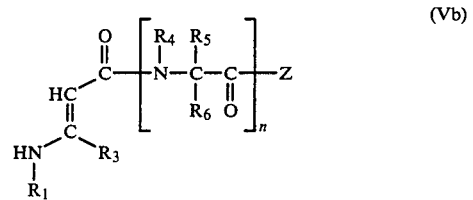

and a compound of the formula VIb or VI, or (cc) by reacting a compound of the formula X with a compound of the formula

and a compound of the formula V, or (cd) by reacting a compound of the formula X with a compound of the formula Va and a compound of the formula VIb or VI, or (ce) by reacting a compound of the formula X with a compound of the formula

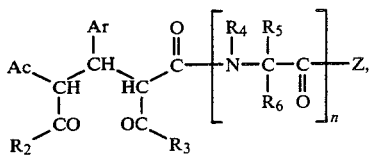

(XI)

or (cf) by reacting a compound of the formula VI with a compound of the formula Va or of the formula

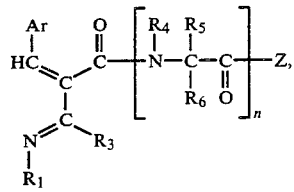

(Vc)

or (cg) by reacting a compound of the formula Vb with a compound of the formula VIa or with a compound of the formula

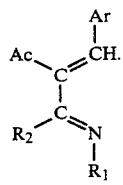

(VIc)

With the exception of the compounds of the formulae IV and X, the compounds of the formulae V, Va-c, VI, VIa-c, VII and XI can be used in the form of tautomers or in the form of tautomeric mixtures; starting materials of the above formulae having salt-forming properties can also be used in the form of salts. Furthermore, in the above-mentioned compounds, the symbols n, Ar, Ac, $R_1$, $R_2$, $R_3$, $R_4$, $R_5$, $R_6$ and Z have the meanings given under formula I.

A compound of the formula X can also be used in the form of an agent that yields the compound in situ, for example ammonia in the form of an ammonium salt, such as ammonium acetate or ammonium bicarbonate, or a light metal compound, for example an alkali metal compound, such as sodium amide or lithium N-methylamide.

The cyclisation reaction (c), and also the condensation reactions (ca) to (cg) for the manufacture of the starting material, usually formed in situ, for the cyclisation reaction, and also process variant (b) are variants of the dihydropyridine synthesis according to Hantzsch. In variant (ca), a total of three molecules of water are removed; in other variants an addition reaction takes the place of some of the water removal, that is to say the removal of water occurs as early as during the manufacture of one or two starting materials. In the reaction of compounds of the formula IV with compounds of the formula Vb and VI according to variant (cb), of compounds of the formula VI with compounds of the formula Vc according to variant (cf), or of compounds of the formula Vb with compounds of the formula VIc according to variant (cg), a compound of the formula X is removed in addition to or instead of water.

If compounds of the formula I are to be manufactured according to variant (ca), undesired secondary products, for example of the type of the 1,4-dihydropyridine-3,5-dicarboxylic acid derivatives, such as corresponding diesters, may be formed. By not adding the reactants simultaneously, the formation of such secondary products can, however, be reduced in that a specific course of reaction is promoted which takes place in situ according to another variant, since, in accordance with the order in which the reaction components are added, for example first a compound of the general formula VI or of the formula Vb can be formed.

The cyclisation and condensation reactions according to the process are carried out in a manner known per se, if necessary in the presence of a condensation agent, especially a basic condensation agent, such as an excess of a basic reaction component or an additional, for example organic, base, such as piperidine or ethyldiisopropylamine, or a metal alcoholate, such as an alkali metal lower alkoxide, or, if a compound of the formula X is in the form of a compound with a light metal, for example in the form of sodium amide, in the presence of acidic agents, for example an organic carboxylic acid, for example acetic acid, and/or a suitable dehydrating or water-absorbing agent, also generally in the presence of an inert organic solvent and at reaction temperatures in the range of from approximately room temperature to approximately 150° C., especially at the boiling temperature of the solvent. If appropriate, the reaction takes place in an inert gas atmosphere, for example a nitrogen atmosphere, and/or, for example when using a low-boiling solvent and/or a starting material of the formula X, in a closed vessel under elevated pressure.

The starting materials used in the process variants are known or can be manufactured according to processes known per se. For example, a compound of the formula Va can be manufactured from a compound of the formula V and a compound of the formula IV, a compound of the formula VIa can be manufactured from a compound of the formula VIb and a compound of the formula IV, a compound of the formula Vb can be manufactured from a compound of the formula V and a compound of the formula X, a compound of the formula Vc can be manufactured from a compound of the formula Vb and a compound of the formula IV, a compound of the formula VIc can be manufactured from a compound of the formula VI and a compound of the formula IV and a compound of the formula XI can be manufactured from a compound of the formula VIb and a compound of the formula Va.

The process variant (d) is carried out in a manner known per se. Reactive functional derivatives of the aldehyde of the formula IV are described above. The reaction is carried out in the absence, but preferably in the presence, of a solvent or diluent or a corresponding mixture and/or in the presence of a condensation agent, the operation being effected while cooling, at room temperature, or preferably while heating, for example in a temperature range of from approximately 0° C. to approximately 200° C., preferably from approximately 40° C. to approximately 150° C., and, if necessary, in a closed vessel, optionally under pressure and/or under an inert gas atmosphere.

The starting material of the formula VIII can be manufactured in a manner known per se; for example, by reacting a compound of the formula V, preferably one in which Z is other than a hydroxy group, with a compound of the formula VI, the starting material of the formula VIII can be obtained directly.

Depending on the radical $Ac_o$ they contain, the starting materials of the formula IX used in process variant (e) may be, for example, carboxylic acids ($Ac_o$ is carboxy), carboxylic acid anhydrides, especially mixed anhydrides, such as acid halides, for example acid chlorides or bromides, ($Ac_o$ is halocarbonyl, for example chloro- or bromo-carbonyl), and also activated esters, for example cyanomethyl or pentachlorophenyl esters, ($Ac_o$ is cyanomethoxycarbonyl or pentachlorophenoxycarbonyl). Such starting materials can be converted, optionally in the presence of condensation agents, by treatment with an alcohol, such as an unsubstituted or substituted lower alkanol, or a reactive derivative thereof, for example a corresponding alcoholate, such as an alkali metal alcoholate, and free carboxylic acids can also be converted by reaction with suitable diazo compounds, such as unsubstituted or substituted diazo-lower alkanes, into compounds of the formula I in which Ac represents the acyl radical of a monoester of carbonic acid. Such compounds can also be obtained when there are used as starting materials of the formula IX salts, especially alkali metal or alkaline earth metal salts, of free carboxylic acid, and these are treated with reactive esters of alcohols, such as unsubstituted or substituted lower alkanols, such as corresponding halides, for example chlorides, bromides or iodides, or organic sulphonic acid esters, for example lower alkanesulphonic acid esters or arenesulphonic acid esters, such as methanesulphonic acid and p-toluenesulphonic acid esters, or when corresponding hydrolysable iminoesters, such as corresponding imino-lower alkyl esters, are hydrolysed to form the esters.

The reaction of free carboxylic acids with alcohols, such as unsubstituted or substituted lower alkanols, advantageously takes place in the presence of an acidic water-removing catalyst, such as a protonic acid, for example hydrochloric acid, hydrobromic acid, sulphuric acid, phosphoric acid or boric acid, benzenesulphonic acid or toluenesulphonic acid, or a Lewis acid, for example boron trifluoride etherate, in an excess of the alcohol used and/or in an inert solvent, if necessary with the removal by distillation, for example azeotropic distillation, of the water freed during the reaction. The reactions can also be carried out in the presence of water-binding condensation agents, such as suitably substituted carbodiimides, for example N,N'-diethyl, N,N'-dicyclohexyl or N-ethyl-N'-(3-dimethylaminopropyl) carbodiimide, optionally in inert organic solvents. Mixed anhydrides, especially acid halides, are reacted, for example, in the presence of acid-binding agents, for example organic bases, especially tertiary nitrogen bases, such as triethylamine, ethyldiisopropylamine or pyridine, or also inorganic bases, for example alkali metal or alkaline earth metal hydroxides or carbonates, such as sodium, potassium or calcium hydroxide or carbonate, with alcohols or with alcoholates, for example alkali metal lower alkoxides.

The reactions of reactive esters, for example cyanomethyl or pentachlorophenyl esters, with alcohols are carried out, for example, in a solvent that is inert towards the reactants and in a temperature range of from approximately 0° C. to approximately 120° C., preferably at from room temperature up to approximately 60° C.

The hydrolysis of iminoester starting materials, especially imino-lower alkyl ester starting materials, is carried out, for example, by means of water-containing mineral acids, such as hydrochloric acid or sulphuric acid; for example, the iminoester salts, for example hydrochlorides, obtained during the addition of hydrogen chloride to nitriles and the reaction with anhydrous alcohols, especially unsubstituted or substituted lower alkanols, can be hydrolysed directly to the corresponding esters after the addition of water. It is also possible, for example, to obtain the desired ester compound of the formula I from a mixture of the nitrile starting material, an alcohol and sulphuric acid having a suitable water content, without isolating the iminoester formed in situ.

Compounds of the formula I in which the radical Ac is the acyl radical of a carbonic acid monoamide can be obtained from compounds of the formula IX in which $Ac_o$ represents a carboxy group, an acid anhydride group, such as halocarbonyl, for example chlorocarbonyl, or an activated ester group, such as cyanomethoxycarbonyl or pentachlorophenoxycarbonyl, by reacting such starting materials, optionally in the presence of a suitable condensation agent, with ammonia or an ammonia-yielding agent or an N-mono- or N,N-di-substituted amine.

These conversions of carboxy groups and suitably functionally modified reactive carboxy groups into optionally N-mono- or N,N-di-substituted carbamoyl groups can be carried out in a manner known per se, for example in accordance with the processes described for the formation of the ester groups.

Compounds of the formula I in which the group Ac is carbamoyl can also be obtained starting from compounds of the formula IX in which the radical $Ac_o$ is cyano. Such starting materials can be converted by hydrolysis, preferably under acidic or basic conditions, for example in the presence of an alkali metal hydroxide, such as sodium hydroxide, and, if desired, in the presence of hydrogen peroxide, in an aqueous-alcoholic solvent, such as aqueous ethanol, into the desired compounds of the formula I with a carbamoyl group Ac.

The reactions mentioned above or below can be carried out under reaction conditions known per se, in the absence or generally in the presence of solvents or diluents, and, depending on the type of reaction and/or reactants, at reduced or elevated temperature, for example in a temperature range of from approximately $-10°$ C. to approximately 150° C., under atmospheric pressure or in a closed vessel, optionally under pressure, and/or in an inert atmosphere, for example under a nitrogen atmosphere.

Starting materials of the formula IX having a free carboxy group $Ac_o$ can be obtained, for example, by manufacturing the corresponding 2-cyanoethyl ester and cleaving this to form the free carboxylic acid under mild conditions, for example by means of aqueous or aqueous-lower alkanolic 1N sodium hydroxide at room temperature. The 2-cyanoethyl ester itself can be obtained, for example, by reacting a compound of the formula IV with a compound of the formula VI in which Ac represents a 2-cyanoethoxycarbonyl group and with a compound of the formula V. The free carboxy group present in the starting material of the formula IX can, if necessary, be converted in a manner known per se into the desired reactive functionally modified form.

The nitrile compounds of the formula IX which also come into consideration as starting materials for process variant (e) can be manufactured, for example, analogously to the above-mentioned 2-cyanoethyl ester compounds by using intermediates that contain a cyano group in the place of the radical Ac.

Compounds of the formula I in which $R_3$ represents functionally modified formyl can be manufactured, for example, according to process (b) from a compound of the formula V in which $R_3$ represents functionally modified formyl, for example a di-lower alkyl acetal, and from a compound of the formula IV and a compound of the formula VI (cf. also European Patent Application No. 107 203).

Compounds of the formula I in which $R_3$ represents functionally modified formyl can be converted in a manner known per se into compounds of the formula I in which $R_3$ represents formyl, and these compounds can themselves be converted in a manner known per se into other compounds of the formula I in which $R_3$ represents, for example, hydroxymethyl, hydroxyimino or cyano (cf. Belgian Pat. No. 879,263). It is also possible, for example, analogously to process (b), to manufacture, from a compound of the formula V in which n represents 0, $R_3$ represents functionally modified formyl and Z preferably represents a group $-OR_7$ in which $R_7$ represents, for example, an acid-protecting group, for example 2-cyanoethyl or carbamoylmethyl, and from a compound of the formula IV and a compound of the formula VI, first a compound of the formula II in which n represents 0 and $R_3$ represents functionally modified formyl. In the last-mentioned compound the radical $R_3$ can again be converted as indicated above, for example, into formyl, hydroxymethyl, hydroxyimino or cyano. The mentioned compounds of the formula II can be converted according to process (a) into compounds of the formula I.

Compounds of the formula I in which $R_2$ represents functional formyl can also be obtained in analogous manner, that is to say, for example, according to process (cb) by reacting a compound of the formula IV and a compound of the formula Vb with a compound of the formula VIb in which $R_2$ represents functionally modified formyl. Such compounds of the formula I can again be converted in a manner known per se into other compounds of the formula I in which $R_2$ represents, for example, formyl, hydroxymethyl, hydroxyimino or cyano.

Compounds of the formula II, and analogously also of the formula I, in which $R_3$ represents amino can be manufactured, for example, according to process (c), especially according to variant (cb), from a compound of the formula Vb' which is completely analogous to a compound of the formula Vb in which $R_3$ represents amino and n represents, for example, 0

(Vb')

and from a compound of the formula IV and a compound of the formula VIb (cf. Liebigs Ann. Chem. 1977, 1895–1908). Starting compounds of the formula Vb' can be obtained according to the customary amidine syntheses, for example by converting a compound NC—CH$_2$—COZ into the corresponding imino ether, for example by means of methanol and HCl, and by treating the latter with, for example, ammonia.

In a similar manner, it is also possible to manufacture compounds of the formula I in which $R_2$ represents amino, that is to say, for example, according to process (b) from a compound of the formula IV, a compound of the formula V, and a compound of the formula VI in which $R_2$ represents amino.

Compounds of the formula I in which Ac represents an acyl radical of cyclic carbonic acid derivatives and/or $R_2$ represents a carbocyclic or heterocyclic aryl radical, can be manufactured, for example, according to process (b), the starting compounds of the formula VI being obtainable, for example, analogously to the processes described in U.S. Pat. No. 4,414,213.

Compounds of the formula I in which $R_1$ represents unsubstituted or substituted lower alkyl can be obtained, for example, by N-alkylation from corresponding compounds of the formula I in which $R_1$ represents hydrogen (cf. U.S. Pat. No. 4,258,042).

Compounds of the formula I in which $R_1$ represents, for example, hydroxy can be manufactured, for example, according to process (c), especially variant (ce), from a compound of the formula XI and hydroxylamine (cf. European Patent Application No. 93 945). From such compounds of the formula I in which $R_1$ represents hydroxy there are obtained by methods of O-alkylation and O-acylation known per se compounds of the formula I in which $R_1$ represents etherified or esterified hydroxy.

Compounds of the formula I in which $R_1$ and $R_2$ together represent unsubstituted or substituted lower alkylene in which a carbon atom is optionally replaced by a hetero atom, can be manufactured, for example, according to process (b') (cf. Liebigs Ann. Chem. 1977, 1888–1894). In a completely analogous manner, compounds of the formula I can be obtained in which $R_1$ and $R_3$ together represent unsubstituted or substituted lower alkylene in which a carbon atom is optionally replaced by a hetero atom, for example by reacting a compound of the formula VIa with a compound of the formula Vb according to process (cg).

Compounds of the formula I in which $R_3$ represents hydrogen can be obtained, for example, by reacting a compound of the formula VIa with a compound of the formula Vb in which $R_3$ represents di-lower alkylamino or lower alkyleneamino. There are first formed 3,4-dihydropyridines which, by means of hydrogenation, for example in glacial acetic acid over PtO$_2$, in an addition-elimination reaction, yield the desired compounds [cf. Angew. Chem. 93, 755–763 (1981)]. Compounds of the formula I in which $R_2$ represents hydrogen can be obtained in a completely analogous manner from a compound of the formula Va and a compound of the formula VI in which $R_2$ represents di-lower alkylamino or lower alkyleneamino.

There is a large amount of information in the literature on the manufacture of 4-aryl-1,4-dihydropyridines, for example in Angew. Chem. 93, 755–763 (1981), Liebigs Ann. Chem. 1977, 1888–1894 and 1895–1908, BE 879 263, DE-A-3 207 982, in European Patent Application Nos. 26 317, 60 897, 93 945 and 107 203, and in U.S. Pat. Nos. 4,258,042 and 4,414,213.

Compounds of the formula I obtainable according to the invention can be converted in a manner known per se into other compounds of the formula I.

For example, in compounds of the formula I in which $R_1$ represents hydrogen, an organic radical $R_1$ can be introduced by treatment with a reactive ester of an alcohol of the formula $R_1$—OH (XII), and compounds of the formula I are thereby produced in which $R_1$ is other than hydrogen.

Reactive esters of compounds of the formula XII, for example of unsubstituted or substituted lower alkanols, are those with strong inorganic or organic acids; there come into consideration, for example, the corresponding halides, especially chlorides, bromides or iodides, also sulphates, and lower alkanesulphonic acid esters or arenesulphonic acid esters, for example methanesulphonic acid, benzenesulphonic acid and p-toluenesulphonic acid esters. The reaction is carried out, if necessary, while cooling or heating, for example in a temperature range of from approximately 0° C. to approximately 100° C., in the presence of a suitable basic condensation agent, for example an alkali metal, an alkali metal amide or an alkali metal hydride, or an alkali metal-lower alkoxide, such as sodium or potassium methoxide, ethoxide or tert.-butoxide, in the presence or absence of a solvent or diluent, at reduced or elevated temperature, for example in a temperature range of from approximately 0° C. to approximately 100° C., and/or under atmospheric pressure or in a closed vessel.

There are preferably used in such N-substitution reactions especially compounds of the formula I that have no other primary or secondary amino groups as substituents since these might perhaps also react with the reactive ester of an alcohol of the formula XII.

Compounds of the formula I in which Z represents the radical $NR_8R_9$ or $OR_7$ in which $R_7$ represents optionally substituted lower alkyl can be converted in the same manner as described above for compounds of the formula IIa in which $R_c$ represents a functionally modified carboxy group, for example by hydrolysis in an alkaline or acidic medium, into compounds of the formula I in which Z represents hydroxy. Conversely, compounds of the formula I in which Z represents hydroxy can be converted in a manner known per se according to customary esterification methods, for example with an excess of a lower alkanol in the presence of an acid, for example hydrochloric acid, as catalyst, into compounds of the formula I in which Z represents $OR_7$ and $R_7$ represents optionally substituted lower alkyl. Analogously, compounds of the formula I in which Z represents hydroxy can also be converted according to customary methods of amide formation, for example by reaction with ammonia or a primary or secondary amine, optionally while removing the water formed during the reaction, into compounds of the formula I in which Z represents the group $NR_8R_9$.

Compounds of the formula I in which n represents 1 or 2 and Z represents hydroxy are identical with compounds of the formula II in which n' represents 1 or 2 and $R_b$ represents carboxy. They can be converted according to process (a) by reaction with a compound of the formula III into other compounds of the formula I in which n represents 2 or 3.

Compounds of the formula I in which Z represents $OR_7$ and $R_7$ represents benzyl can be converted, for example, by hydrogenolysis into other compounds of the formula I in which Z represents hydroxy.

In addition, substituents present in compounds of the formula I obtainable according to the process can be converted into other substituents.

For example, esterified carboxy groups, such as corresponding groups Ac and/or $C(=O)-OR_7$, can be converted by transesterification into other esters. There are preferably used corresponding alcohol compounds having a boiling point clearly above that of the alcohol of the esterified group in the compound of the formula I to be converted and the reaction is carried out, for example, in an excess of the hydroxy compound and/or in an inert organic solvent which preferably also has a boiling point clearly above that of the alcohol of the esterified group, preferably in the presence of a catalyst, for example an alkali metal-lower alkoxide, such as sodium or potassium methoxide or ethoxide, or a lower alkylester of ortho-titanic acid, e.g. the ortho-titanic acid isopropylester, at elevated temperature and generally while distilling off the alcohol which has been freed.

Esterified carboxy groups, for example corresponding radicals Ac or especially a radical $Z=C(=O)-OR_7$, can, for example, also be converted into other esters by, for example, first subjecting them to acidic or, preferably, alkaline hydrolysis and then converting the resulting acids in a manner known per se into other esters.

Compounds of the formula I having esterified carboxy groups, such as lower alkoxycarbonyl groups, especially corresponding groups Ac or the radical $C(=O)-OR_7$, can be converted into compounds having corresponding carbamoyl groups, for example, by treatment with ammonia, and also mono- or di-substituted amines, if necessary at elevated temperature and/or in a closed vessel.

Suitable substituents of an aromatic radical, for example halogen atoms, especially fluorine atoms, can be exchanged for other substituents, for example an optionally substituted amino group (for example by treatment with a primary or secondary amine, for example a compound of the formula X).

All the starting materials mentioned in the described processes and subsequent operations that contain one or more optically active carbon atoms can be used in the corresponding reactions in the form of racemic mixtures, racemates, optical isomers or mixtures of optical isomers and generally result in compounds of the formula I that at the corresponding carbon atom(s) have the same configuration or the same configurations as the starting material.

Depending upon the reaction conditions, the compounds of the formula I can be obtained in free form or in the form of salts.

Resulting acid addition salts can be converted in a manner known per se into the free compounds, for example by treatment with a base, such as an alkali metal hydroxide, or into different salts, for example by treatment with suitable acids or derivatives thereof. Resulting free compounds having salt-forming properties, for example having appropriate basic groups, can be converted into their salts, for example by treatment with acids or appropriate anion exchangers.

As a result of the close relationship between the compounds of the formula I in free form and in the form of salts, hereinbefore and hereinafter the free compounds or their salts are to be understood as meaning optionally also the corresponding salts or free compounds, respectively, where appropriate and expedient.

The compounds, including their salts, can also be obtained in the form of their hydrates, or their crystals can include, for example, the solvent used for crystallisation.

Depending upon the reaction and/or the type of starting materials, the compounds of the formula I may be obtained in the form of racemates, racemic mixtures or optical antipodes.

Resulting racemic mixtures can be separated into the pure racemates or diastereoisomers on the basis of the physico-chemical differences between the racemates in known manner, for example by chromatography and/or fractional crystallisation.

Racemates can be separated into the optical anitpodes according to methods known per se, for example by recrystallisation from an optically active solvent, with the aid of suitable micro-organisms or by reaction of a compound of the formula I having salt-forming, for example basic, properties with an optically active salt-forming agent, such as an optically active acid, and separation of the mixtures of salts obtained in this manner, for example on the basis of their different solubilities, into the diastereoisomeric salts from which the antipodes can be freed, for example by treatment with a base.

Optical antipodes of neutral compounds of the formula I can be obtained, for example, also according to process (e) using an optically active acid of the formula IX, it being possible for this to be formed, for example, from the corresponding racemic acid in customary manner, for example by salt formation with an optically active base, separation of the diastereoisomeric salts and liberation of the optically active acid, or using a reactive functional derivative of an optically active acid.

It is also possible, for example, to transesterify compounds of the formula I that have an esterified carboxy group, for example a corresponding group Ac, using an optically active alcohol in accordance with the process described above, and to separate the resulting diastereoisomeric mixture, for example by means of fractional crystallisation, into the antipodes.

Advantageously, the pharmacologically more active isomer or the more active antipode is isolated from a diastereoisomeric mixture or racemate. As a rule, pharmacological activity is especially great if the following configuration is present at the C4-carbon atom of the 1,4-dihydropyridine skeleton: 4R if, in accordance with the rule of Cahn, Ingold and Prelog, the substituent in the 5-position, that is to say the amino acid side chain, has lower priority than the radical Ac in the 3-position of the dihydropyridine nucleus and higher priority than the radical Ar. Conversely, 4S if the radical Ac has a lower priority than the amino acid side chain and a higher priority than the radical Ar. The following configuration at the C4-carbon atom is therefore preferred, in which the carbon atoms C3, C4 and C5 lie in the plane of the paper, the radical Ar lies above the plane of the paper and the hydrogen atom lies below the plane of the paper:

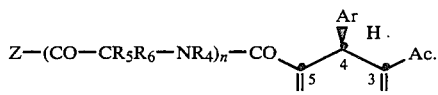

The invention relates also to those forms of the process according to which a compound obtainable as an intermediate at any stage of the process is used as starting material and the remaining steps are carried out, or a starting material is used in the form of a derivative, for example a salt, and/or its racemates or antipodes, or is formed under the reaction conditions.

In the process of the present invention it is preferable to use those starting materials which result in the compounds described at the beginning as being especially valuable. The present invention also relates to novel starting materials and to processes for their manufacture. The invention also relates to novel intermediates obtainable according to the process and to processes for their manufacture.

The invention relates also to the use of the compounds of the formula I or pharmaceutically acceptable salts of such compounds having salt-forming properties, especially as compounds that can be used pharmacologically, more especially compounds that can be used for the dilation of the coronary vessels and/or as antihypertensives. They can be used, preferably in the form of pharmaceutical preparations, in a method for the prophylactic and/or therapeutic treatment of the animal or human body, especially for the treatment of Angina pectoris, hypertonia and other cardiovascular disorders.

The dosage of the active ingredient, which is administered alone or together with the customary carriers and adjuncts, depends upon the species to be treated, age and individual condition and on the mode of administration. The daily doses for mammals of approximately 70 kg body weight, depending upon the type of disorder, individual condition and age, are preferably between 1 and 100 mg and especially between 2 and 20 mg.

The invention relates also to pharmaceutical preparations that contain compounds of the formula I, or pharmaceutically acceptable salts of such compounds having salt-forming properties, as active ingredients and to processes for their manufacture.

The pharmaceutical preparations according to the invention are for enteral, such as peroral or rectal, sublingual and parenteral administration to warm-blooded animals. Appropriate dosage unit forms, especially for peroral and/or sublingual administration, for example dragées, tablets or capsules, preferably contain from approximately 0.5 to approximately 100 mg, especially from approximately 5 to approximately 50 mg, of a compound of the formula I, or a pharmaceutically acceptable salt of such a compound that is capable of salt-formation, together with pharmaceutically acceptable carriers.

Suitable carriers are, especially, fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methylcellulose and/or polyvinylpyrrolidone, and/or, if desired, disintetrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores may be provided with suitable coatings that may be resistant to gastric juices, there being used, inter alia, concentrated sugar solutions that may contain gum arabic, talc, polyvinylpyrrolidone, polyethylene glycol and/or titanium dioxide, or lacquer solutions in suitable organic solvents or solvent mixtutes, or, for the manufacture of coatings resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical preparations are dry-filled capsules consisting of gelatine, and also soft sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added. There are preferred, inter alia, capsules that either can be readily bitten through in order, for example at the first signs of an attack of Angina pectoris, to obtain as rapid an action as possible through sublingual absorption of the active ingredient, or can be swallowed without chewing.

There come into consideration as rectally administrable pharmaceutical preparations, for example, suppositories that consist of a combination of the active ingredient and a suppository base. Suitable as suppository bases are, for example, natural or synthetic triglycerides, paraffin hydrocarbons, polyethylene glycols or higher alkanols. It is also possible to use gelatine rectal capsules that contain a combination of the active ingredient and a base material; suitable base materials are, for example, liquid triglycerides, polyethylene glycols or paraffin hydrocarbons.

Suitable for parenteral administration are especially aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that contain viscosity-increasing substances, for example sodium carboxymethylcellulose, sorbitol and/or dextran and optionally stabilisers.

The pharmaceutical preparations of the present invention can be manufactured in a manner known per se, for example by means of conventional mixing, granulating, confectioning, dissolving or lyophilising processes. Thus, pharmaceutical preparations for oral administration can be obtained by combining the active ingredient with solid carriers, optionally granulating a resulting mixture, and processing the mixture or granulate, if desired or necessary after the addition of suitable adjuncts, to form tablets or dragée cores.

The following examples (a) to (c) are intended to illustrate the manufacture of some typical forms of administration but do not in any way represent the only forms thereof.

(a) Tablets containing 25 mg of active ingredient can be manufactured as follows:

| Composition: (for 1000 tablets) | |
|---|---|
| active ingredient | 25.0 g |
| corn starch | 70.0 g |
| lactose (fine) | 78.5 g |
| cellulose | 75.0 g |
| magnesium stearate | 1.5 g |
| water | q.s. |

The active ingredient is mixed with 60 g of corn starch and the lactose and kneaded with a paste made from 10 g of corn starch and water. The moist mass is granulated, dried and mixed with the crystalline cellulose and the magnesium stearate. The homogeneous mixture is compressed to form 250 mg tablets (having a breaking groove); the tablets are 9 mm in diameter.

(b) Capsules containing 10 mg of active ingredient can be manufactured as follows:

| Composition: | |
|---|---|
| active ingredient | 2500 mg |
| talc | 200 mg |
| colloidal silica | 50 mg |

The active ingredient is intimately mixed with the talc and the colloidal silica and the mixture is forced through a sieve of 0.5 mm mesh width and the mixture is then introduced in 11 mg portions into hard gelatine capsules of suitable size.

(c) A sterile solution of 5.0 g of the active ingredient in 5000 ml of distilled water is introduced into 5 ml ampoules, the ampoules containing 5 mg of active ingredient in 5 ml of solution.

The following Examples illustrate the manufacture of the novel compounds of the formula I but are not intended to limit the scope of the invention in any way. Temperatures are given in degrees Centigrade.

EXAMPLE 1

A mixture of 9.6 g of 1,4-dihydro-2,6-dimethyl-4-(3-nitrophenyl)-pyridine-3,5-dicarboxylic acid 3-(1-benzotriazolyl)-ester-5-methyl ester, 3.6 g of L-valine ethyl ester hydrochloride and 2.5 ml of N-ethylmorpholine in 90 ml of anhydrous dimethylformamide is stirred for 16 hours at 80° under a nitrogen atmosphere. 300 ml of ice-water are added to the yellow reaction mixture while cooling with ice-water. The whole is then stirred for a further 1 hour in an ice bath at from 0° to 5°, the crude product being precipitated in the form of a highly viscous mass. The solvent is decanted off and the residue is dried under reduced pressure. The resulting resinous crude product is a 1:1 diastereoisomeric mixture of (4R)- and (4S)-1,4-dihydro-2,6-dimethyl-3-methoxycarbonyl-4-(3-nitrophenyl)-pyridine-5-carboxylic acid N-[(1S)-1-ethoxycarbonyl-2-methyl-1-propyl]-amide.

In order to separate the diastereoisomers, 30 ml of diisopropyl ether are added to the crude product and the whole is stirred for 1 hour at from 0° to 5°, (+)-(4S)-1,4-dihydro-2,6-dimethyl-3-methoxycarbonyl-4-(3-nitrophenyl)-pyridine-5-carboxylic acid N-[(1S)-1-ethoxycarbonyl-2-methyl-1-propyl]-amide crystallising in the form of slightly yellow crystals. This first diastereoisomer is uniform in configuration; it melts at from 198° to 200° and its specific rotation is $[\alpha]_D^{20} + 75°$ (c=0.6, ethanol).

In order to isolate the second diastereoisomer, the mother liquor is concentrated by evaporation under reduced pressure. The residue is purified by chromatography over approximately 100 times the amount of silica gel (elution with a 7:3 mixture of hexane and ethyl acetate) and the crude second diastereoisomer is crystallised by stirring in 20 ml of diethyl ether at from 0° to 5°. The resulting (−)-(4R)-1,4-dihydro-2,6-dimethyl-3-methoxycarbonyl-4-(3-nitrophenyl)-pyridine-5-carboxylic acid N-[(1S)-1-ethoxycarbonyl-2-methyl-1-propyl]-amide melts at from 147° to 148°. The crude product is purified further by means of recrystallisation from acetone. The resulting pale yellow, fine-leaved needles melt at from 156° to 157°, deep yellow, rhomboid crystals beginning to grow out of the melt at the same time, as a new crystal modification; renewed melting takes place at from 171° to 172°. This crystalline second diastereoisomer is uniform in configuration and exhibits a specific rotation of $[\alpha]_D^{20} = -34.9°$ (c=1.0, ethanol).

The starting material can be manufactured as follows: A solution of 6.7 g of 1,4-dihydro-2,6-dimethyl-4-(3-nitrophenyl)-pyridine-3,5-dicarboxylic acid monomethyl ester [see European Patent Application No. 11.706], 3.4 g of 1-hydroxybenzotriazole and 4.6 g of N,N'-dicyclohexyl carbodiimide in 100 ml of anhydrous dimethylformamide is left to stand for 16 hours at from 0° to 5° under a nitrogen atmosphere. The N,N'-dicyclohexylurea that has crystallised out is filtered off. While cooling in an ice bath, 300 ml of water are added to the yellow filtrate and the whole is stirred for 1 hour at from 0° to 5°, the amorphous crude product being precipitated. After filtration, the filtration residue is washed with 400 ml of water and dried in vacuo. For the purpose of further purification, the crude product is dissolved in 40 ml of ethyl acetate and stirred for 1 hour at from 0° to 5°. The N,N'-dicyclohexylurea that has crystallised out is then removed by filtration and the filtrate is concentrated by evaporation under reduced pressure, 1,4-dihydro-2,6-dimethyl-4-(3-nitrophenyl)-pyridine-3,5-dicarboxylic acid 3-(1-benzotriazolyl)-ester-5-methyl ester being obtained in quantitative yield in the form of a highly viscous foam: 250 MHz FT-$^1$H-NMR (CDCl$_3$): 2.46 (2s, 6H, dihydropyridyl-CH$_3$); 3.70 (s, 3H, —COOCH$_3$); 5.44 (s, 1H, 4-dihydropyridyl-H); 6.78 (s, 1H, N-H); 6.92, 7.39, 8.04 (3m, 4H, benzotriazolyl-H); 6.48, 7.79, 8.14, 8.24 (4m, 4H, phenyl-H).

EXAMPLE 2

A mixture of 12.5 g of (S)-N-acetoacetyl-α-aminoisovaleric acid ethyl ester [manufactured analogously to the method described in Pharm. Acta. Helv. 38, 616 (1963)], 6.2 g of 3-aminocrotonic acid methyl ester and 8.2 g of 3-nitrobenzaldehyde in 100 ml of ethanol is stirred for 16 hours at 80° under a nitrogen atmosphere. The yellow reaction mixture is concentrated by evaporation under reduced pressure. The oily residue is dissolved in 300 ml of dichloromethane and washed twice with 100 ml of water each time. The organic phase is dried with sodium sulphate and filtered and the filtrate is concentrated by evaporation under reduced pressure. The residue is purified by chromatography over approximately 100 times the amount of silica gel (elution with a 7:3 mixture of hexane and ethyl acetate). The resulting resinous crude product is a 1:1 diastereoisomeric mixture of (4R)- and (4S)-1,4-dihydro-2,6-dimethyl-3-methoxycarbonyl-4-(3-nitrophenyl)-pyridine-5-carboxylic acid N-[(1S)-1-ethoxycarbonyl-2-methyl-1-propyl]-amide. The separation of the diastereoisomers is effected as described in Example 1.

EXAMPLE 3

A solution of 1.8 g of L-valine ethyl ester hydrochloride in 30 ml of anhydrous tetrahydrofuran is added dropwise at from 0° to 10° to a solution of 3.5 g of 1,4-dihydro-2,6-dimethyl-3-methoxycarbonyl-4-(3-nitrophenyl)-pyridine-5-carboxylic acid chloride [see Chem. Pharm. Bull. 28, 2809 (1980)] and 1.3 ml of N-ethylmorpholine in 30 ml of anhydrous tetrahydrofuran. When the addition is complete, the whole is allowed to warm up to room temperature. The reaction mixture is concentrated by evaporation under reduced pressure. The residue is dissolved in 100 ml of dichloromethane and washed several times with water. The organic phase is dried with sodium sulphate and filtered and the filtrate is concentrated by evaporation under reduced pressure. The residue is purified by chromatography over approximately 100 times the amount of silica gel (elution with a 3:7 mixture of ethyl acetate and hexane). The resulting crude product is a 1:1 diastereoisomeric mixture of (4R)- and (4S)-1,4-dihydro-2,6-dimethyl-3-methoxycarbonyl-4-(3-nitrophenyl)-pyridine-5-carboxylic acid N-[(1S)-1-ethoxycarbonyl-2-methyl-1-propyl]-amide. The separation of the diastereoisomers is effected as described in Example 1.

EXAMPLE 4

Analogously to the process described in Example 1 there is obtained, from a mixture of 42 g of 1,4-dihydro-2,6-dimethyl-4-(3-nitrophenyl)-pyridine-3,5-dicarboxylic acid 3-(1-benzotriazolyl)-ester-5-methyl ester, 16 g of D-valine ethyl ester hydrochloride and 11 ml of N-ethylmorpholine in 350 ml of anhydrous dimethylformamide, (—)-(4R)-1,4-dihydro-2,6-dimethyl-3-methoxycarbonyl-4-(3-nitrophenyl)-pyridine-5-carboxylic acid N-[(1R)-1-ethoxycarbonyl-2-methyl-1-propyl]-amide which, after recrystallisation from a mixture of acetone and diisopropyl ether, melts at from 199° to 200°. This diastereoisomer is uniform in configuration and exhibits a specific rotation of $[\alpha]_D^{20} = -75°$ (c=0.7, ethanol).

Analogously to the process described in Example 1, (+)-(4S)-1,4-dihydro-2,6-dimethyl-3-methoxycarbonyl-4-(3-nitrophenyl)-pyridine-5-carboxylic acid N-[(1R)-1-ethoxycarbonyl-2-methyl-1-propyl]-amide is isolated from the mother liquor. As a result of trituration of the amorphous crude product with diethyl ether, this diastereoisomer crystallises in a form that is uniform in configuration; it melts at from 144° to 145° and exhibits a specific rotation of $[\alpha]_D^{20} = +30°$ (c=0.4, ethanol).

EXAMPLE 5

Analogously to the process described in Example 1 there is obtained, from a mixture of 10.2 g of 1,4-dihydro-2,6-dimethyl-4-(3-nitrophenyl)-pyridine-3,5-dicarboxylic acid 3-(1-benzotriazolyl)-5-isopropyl ester, 3.5 g of L-valine ethyl ester hydrochloride and 2.5 ml of N-ethylmorpholine in 90 ml of anhydrous dimethylformamide, (—)-(4R)-1,4-dihydro-2,6-dimethyl-3-isopropoxycarbonyl-4-(3-nitrophenyl)-pyridine-5-carboxylic acid N-[(1S)-1-ethoxycarbonyl-2-methyl-1-propyl]-amide which, after recrystallisation from ethyl acetate, melts at from 178° to 179°. The specific rotation of this diastereoisomer, which is uniform in configuration, is $[\alpha]_D^{20} = -28°$ (c=0.9, ethanol).

Analogously to the process described in Example 1, (+)-(4S)-1,4-dihydro-2,6-dimethyl-3-isopropoxycarbonyl-4-(3-nitrophenyl)-pyridine-5-carboxylic acid N-[(1S)-1-ethoxycarbonyl-2-methyl-1-propyl]-amide is isolated in amorphous form from the mother liquor. The specific rotation of this amorphous diastereoisomer is $[\alpha]_D^{20} = +46°$ (c=0.45, ethanol); according to the $^1$H-NMR spectrum it also contains approximately 20% of (—)-(4R)-1,4-dihydro-2,6-dimethyl-3-isopropoxycarbonyl-4-(3-nitrophenyl)-pyridine-5-carboxylic acid N-[(1S)-1-ethoxycarbonyl-2-methyl-1-propyl]-amide.

The starting material can be obtained as follows: Analogously to the process described in Example 1, 1,4-dihydro-2,6-dimethyl-4-(3-nitrophenyl)-pyridine-3,5-dicarboxylic acid 3-(1-benzotriazolyl)-ester-5-isopropyl ester is obtained, in the form of an amorphous product, from a mixture of 16.2 g of 1,4-dihydro-2,6-dimethyl-4-(3-nitrophenyl)-pyridine-3,5-dicarboxylic acid monoisopropyl ester [see European Patent Application No. 11.706], 7.6 g of 1-hydroxybenzotriazole and 10.2 g of N,N'-dicyclohexyl carbodiimide in 225 ml of anhydrous dimethylformamide.

250 mHz FT-$^1$H-NMR (CDCl$_3$): 1.13, 1.30 (2d, 6H, isopropyl-CH$_3$); 2.44, 2.46 (2s, 6H, dihydropyridyl-CH$_3$); 5.00 (m, 1H, —O—CH—); 5.40 (s, 1H, 4-dihydropyridyl-H); 6.28 (s, 1H, —NH—); 6.89, 7.40, 8.05 (3m, 4H, benzotriazolyl-H); 7.49, 7.79, 8.15, 8.25 (4m, 4H, phenyl-H).

EXAMPLE 6

Analogously to the process described in Example 1 there is obtained, from a mixture of 30 g of 1,4-dihydro-2,6-dimethyl-4-(3-nitrophenyl)-pyridine-3,5-dicarboxylic acid 3-(1-benzotriazolyl)-ester-5-isopropyl ester, 9.8 g of D-valine ethyl ester hydrochloride and 6.8 ml of N-ethylmorpholine in 120 ml of anhydrous dimethylformamide, (+)-(4S)-1,4-dihydro-2,6-dimethyl-3-isopropoxycarbonyl-4-(3-nitrophenyl)-pyridine-5-carboxylic acid N-[(1R)-1-ethoxycarbonyl-2-methyl-1-propyl]-amide. This diastereoisomer, which is uniform in configuration, melts at from 176° to 177° and exhibits a specific rotation of $[\alpha]_D^{20}= +24°$ (c=0.53, ethanol).

Analogously to the process described in Example 1, (−)-(4R)-1,4-dihydro-2,6-dimethyl-3-isopropoxycarbonyl-4-(3-nitrophenyl)-pyridine-5-carboxylic acid N-[(1R)-1-ethoxycarbonyl-2-methyl-1-propyl]-amide is isolated in amorphous form from the mother liquor. The specific rotation of this amorphous diastereoisomer is $[\alpha]_D^{20}= −47°$ (c=0.65, ethanol); according to the $^1$H-NMR spectrum it also contains approximately 5% of (+)-(4S)-1,4-dihydro-2,6-dimethyl-3-isopropoxycarbonyl-4-(3-nitrophenyl)-pyridine-5-carboxylic acid N-[(1R)-1-ethoxycarbonyl-2-methyl-1-propyl]-amide.

EXAMPLE 7

Analogously to the process described in Example 1 there is obtained, from a mixture of 42 g of 1,4-dihydro-2,6-dimethyl-4-(3-nitrophenyl)-pyridine-3,5-dicarboxylic acid 3-(1-benzotriazolyl)-ester-5-isopropyl ester, 14 g of L-leucine methyl ester hydrochloride and 9.6 ml of N-ethylmorpholine in 250 ml of anhydrous dimethylformamide, (+)-(4S)-1,4-dihydro-2,6-dimethyl-3-isopropoxycarbonyl-4-(3-nitrophenyl)-pyridine-5-carboxylic acid N-[(1S)-1-methoxycarbonyl-3-methyl-1-butyl]-amide which, after recrystallisation from ethyl acetate, melts at from 176° to 177°. This crystalline diastereoisomer is uniform in configuration and exhibits a specific rotation of $[\alpha]_D^{20}= +106°$, (c=0.48, ethanol).

Analogously to the process described in Example 1, (−)-(4R)-1,4-dihydro-2,6-dimethyl-3-isopropoxycarbonyl-4-(3-nitrophenyl)-pyridine-5-carboxylic acid N-[(1S)-1-methoxycarbonyl-3-methyl-1-butyl]-amide is isolated from the mother liquor. As a result of trituration of the amorphous crude product with diethyl ether, this diastereoisomer crystallises in a form that is uniform in configuration; it melts at from 154° to 155° and exhibits a specific rotation of $[\alpha]_D^{20}= −55°$, (c=0.78, ethanol).

EXAMPLE 8

Analogously to the process described in Example 1 there is obtained, from a mixture of 21 g of 1,4-dihydro-2,6-dimethyl-4-(3-nitrophenyl)-pyridine-3,5-dicarboxylic acid 3-(1-benzotriazolyl)-ester-5-isopropyl ester, 6.9 g of D-leucine methyl ester hydrochloride and 4.8 ml of N-ethylmorpholine in 120 ml of anhydrous dimethylformamide, (−)-(4R)-1,4-dihydro-2,6-dimethyl-3-isopropoxycarbonyl-4-(3-nitrophenyl)-pyridine-5-carboxylic acid N-[(1R)-1-methoxycarbonyl-3-methyl-1-butyl]-amide which, after recrystallisation from ethyl acetate, melts at from 175° to 176°. This diastereoisomer, which is uniform in configuration, exhibits a specific rotation of $[\alpha]_D^{20}= −109°$ (c=0.28, ethanol).

Analogously to the process described in Example 1, (+)-(4S)-1,4-dihydro-2,6-dimethyl-3-isopropoxycarbonyl-4-(3-nitrophenyl)-pyridine-5-carboxylic acid N-[(1R)-1-methoxycarbonyl-3-methyl-1-butyl]-amide is isolated from the mother liquor in an amorphous form that is, however, uniform in configuration. The specific rotation of this diastereoisomer is $[\alpha]_D^{20}= +48°$ (c=0.79, ethanol).

EXAMPLE 9

Analogously to the process described in Example 1 there is obtained, from a mixture of 23 g of 1,4-dihydro-2,6-dimethyl-4-(3-nitrophenyl)-pyridine-3,5 dicarboxylic acid 3-(1-benzotriazolyl)-ester-5-methyl ester, 9.3 g of D-leucine ethyl ester hydrochloride and 3.5 ml of N-ethylmorpholine in 150 ml of anhydrous dimethylformamide, (−)-(4R)-1,4-dihydro-2,6-dimethyl-3-methoxycarbonyl-4-(3nitrophenyl)-pyridine-5-carboxylic acid N-[(1R)-1-ethoxycarbonyl-3-methyl-1-butyl]amide which, after recrystallisation from a mixture of ethyl acetate and diisopropyl ether, melts at from 207° to 209°. This diastereoisomer is uniform in configuration and its specific rotation is $[\alpha]_D^{20}= −116°$ (c=0.76, ethanol).

Analogously to the process described in Example 1, (+)-(4S)-1,4-dihydro-2,6-dimethyl-3-methoxycarbonyl-4-(3-nitrophenyl)-pyridine-5-carboxylic acid N-[(1R)-1-ethoxycarbonyl-3-methyl-1-butyl]-amide is isolated from the mother liquor. After recrystallisation of the crude product from a mixture of diethyl ether and hexane, a crystalline product is obtained which melts at from 112° to 114° and the specific rotation of which is $[\alpha]_D^{20}= +21°$ (c=0.5, ethanol). On the basis of the $^1$H-NMR spectrum this crystalline form also contains from 5 to 10% of (−)-(4R)-1,4-dihydro2,6-dimethyl-3-methoxycarbonyl-4-(3-nitro-phenyl)pyridine-5-carboxylic acid N-[(1R)-1-ethoxy-carbonyl-3-methyl-1-butyl]-amide.

EXAMPLE 10

Analogously to the process described in Example 1 there is obtained, from a mixture of 19.2 g of 1,4-dihydro-2,6-dimethyl-4-(3-nitrophenyl)-pyridine-3,5-dicarboxylic acid 3-(1-benzotriazolyl)-ester-3-methyl ester, 7.8 g of L-leucine ethyl ester hydrochloride and 2.9 ml of N-ethylmorpholine in 120 ml of anhydrous dimethylformamide, (+)-(4S)-1,4-dihydro-2,6-dimethyl-3-methoxycarbonyl-4-(3-nitrophenyl)-pyridine-5-carboxylic acid N-[(1S)-1-ethoxycarbonyl-3-methyl-1-butyl]-amide which, after recrystallisation from a mixture of ethyl acetate and diisopropyl ether, melts at from 206° to 207°. This crystalline form is uniform in configuration and its specific rotation is $[\alpha]_D^{20}= +105°$ (c=0.26, ethanol).

Analogously to the process described in Example 1, (−)-(4R)-1,4-dihydro-2,6-dimethyl-3-methoxycarbonyl-4-(3-nitrophenyl)-pyridine-5-carboxylic acid N-[(1S)1-ethoxycarbonyl-3-methyl-1-butyl]-amide is isolated from the mother liquor in the form of a crude product. By means of recrystallisation from a mixture of diethyl ether and hexane, a crystalline product is obtained which melts at from 118° to 120° and the specific rotation of which is $[\alpha]_D^{20} = -23°$ (c=0.7, ethanol).

On the basis of the $^1$H-NMR spectrum this crystalline form also contains approximately 20% of (+)(4S)-1,4-dihydro-2,6-dimethyl-3-methoxycarbonyl-4-(3-nitrophenyl)-pyridine-5-carboxylic acid N-[(1S)-1-ethoxycarbonyl-3-methyl-1-butyl]-amide.

EXAMPLE 11

Analogously to the process described in Example 1 there is obtained, from a mixture of 25 g of 1,4-dihydro-2,6-dimethyl-4-(3-nitrophenyl)-pyridine-3,5-dicarboxylic acid 3-(1-benzotriazolyl)-ester-5-methyl ester, 8.6 g of L-proline methyl ester hydrochloride and 6.6 ml of N-ethylmorpholine in 120 ml of anhydrous dimethylformamide, (+)-(4S)-5-[(2S)-2-methoxycarbonylpyrrolidin-1-ylcarbonyl]-1,4-dihydro-2,6-dimethyl-3-methoxycarbonyl-4-(3-nitrophenyl)-pyridine which, after recrystallisation from a mixture of ethyl acetate and hexane, melts at from 180° to 181°. This crystalline diastereoisomer is uniform in configuration and its specific rotation is $[\alpha]_D^{20} = +104°$ (c=0.7, ethanol).

Analogously to the process described in Example 1, (−)-(4R)-5-[(2S)-2-methoxycarbonylpyrrolidin-1-ylcarbonyl]-1,4-dihydro-2,6-dimethyl-3-methoxycarbonyl-4-(3-nitrophenyl)-pyridine, which, after recrystallisation from a mixture of ethyl acetate and diisopropyl ether, melts at from 118° to 119°, is isolated from the mother liquor. This diastereoisomer, which is uniform in configuration, exhibits a specific rotation of $[\alpha]_D^{20} = -59°$ (c=0.5, ethanol).

EXAMPLE 12

Analogously to the process described in Example 1 there is obtained, from a mixture of 23 g of 1,4-dihydro-2,6-dimethyl-4-(3-nitrophenyl)-pyridine-3,5-dicarboxylic acid 3-(1-benzotriazolyl)-ester-5-methyl ester, 7.9 g of D-proline methyl ester hydrochloride and 6 ml of N-ethylmorpholine in 150 ml of anhydrous dimethylformamide, (−)-(4R)-5-[(2R)-2-methoxycarbonylpyrrolidin-1-ylcarbonyl]-1,4-dihydro-2,6-dimethyl-3-methoxycarbonyl-4-(3-nitrophenyl)-pyridine which, after recrystallisation from a mixture of acetone and diisopropyl ether, melts at from 180° to 181°. This crystalline diastereoisomer is uniform in configuration and exhibits a specific rotation of $[\alpha]_D^{20} = -97°$ (c=0.97, ethanol).

Analogously to the process described in Example 1, (+)-(4S)-5-[(2R)-2-methoxycarbonylpyrrolidin-1-ylcarbonyl]-1,4-dihydro-2,6-dimethyl-3-methoxycarbonyl-4-(3-nitrophenyl)-pyridine, which, after recrystallisation from a mixture of acetone and diethyl ether, melts at from 120° to 122°, is isolated from the mother liquor. This diastereoisomer, which is uniform in configuration, exhibits a specific rotation of $[\alpha]_D^{20} = +56°$ (c=0.55, ethanol).

EXAMPLE 13

Analogously to the process described in Example 1, racemic 1,4-dihydro-2,6-dimethyl-3-methoxycarbonyl-4-(3-nitrophenyl)-pyridine-5-carboxylic acid N-(methoxycarbonylmethyl)-amide is obtained, in amorphous form, from a mixture of 18 g of 1,4-dihydro-2,6-dimethyl-4-(3-nitrophenyl)-pyridine-3,5-dicarboxylic acid 3-(1-benzotriazolyl)-ester-5-methyl ester, 4.7 g of glycine methyl ester hydrochloride and 4.7 ml of N-ethylmorpholine in 150 ml of anhydrous dimethylformamide; 250 MHz FT-$^1$H-NMR (CDCl$_3$): 2.32, 2.35 (2s, 6H, dihydropyridyl-CH$_3$); 3.67, 3.73 (2s, 6H, —COOCH$_3$); 4.00 (d, 2H, -N-CH$_2$); 4.96 (s, 1H, 4-dihydropyridyl-H); 5.75 (s, 1H, 1-dihydropyridyl-H); 5.90 (t, 1H, —CONH); 7.4–8.18 (m, 4H, phenyl-H).

EXAMPLE 14

Analogously to the process described in Example 1 there is obtained, from a mixture of 15 g of 1,4-dihydro-2,6-dimethyl-4-(3-nitrophenyl)-pyridine-3,5-dicarboxylic acid 3-(1-benzotriazolyl)-ester-5-methyl ester, 5.2 g of α-aminoisobutyric acid ethyl ester hydrochloride and 3.6 ml of N-ethylmorpholine in 100 ml of anhydrous dimethylformamide, racemic 1,4-dihydro-2,6-dimethyl-3-methoxycarbonyl-4-(3-nitrophenyl)-pyridine-5-carboxylic acid N-(1-ethoxycarbonyl-1-methyl-1-ethyl)-amide which, after recrystallisation from a mixture of ethyl acetate and diethyl ether, melts at from 160° to 161°.

EXAMPLE 15

Analogously to the process described in Example 1 there is obtained, from a mixture of 18.5 g of 1,4-dihydro-2,6-dimethyl-4-(3-nitrophenyl)-pyridine-3,5-dicarboxylic acid 3-(1-benzotriazolyl)-ester-5-methyl ester, 6 g of L-alanine ethyl ester hydrochloride and 4.6 ml of N-ethylmorpholine in 100 ml of anhydrous dimethylformamide, a 1:1 diastereoisomeric mixture of (4R)- and (4S)-1,4-dihydro-2,6-dimethyl-3-methoxycarbonyl-4-(3-nitrophenyl)-pyridine-5-carboxylic acid N-[(1S)-1-ethoxycarbonyl-1-ethyl]-amide which, after recrystallisation from a mixture of ethyl acetate and diisopropyl ether, melts at from 134° to 135°.

EXAMPLE 16

Analogously to the process described in Example 1, a 1:1 diastereoisomeric mixture of (4R)- and (4S)-1,4-dihydro-2,6-dimethyl-3-methoxy-carbonyl-4-(3-nitrophenyl)-pyridine-5-carboxylic acid N-[(1S)-1-methoxycarbonyl-2-(4-hydroxyphenyl)-1-ethyl]-amide is obtained, in amorphous form, from a mixture of 21.7 g of 1,4-dihydro-2,6-dimethyl-4-(3-nitrophenyl)-pyridine-3,5-dicarboxylic acid 3-(1-benzotriazolyl)-ester-5-methyl ester and 8.2 g of L-tyrosinemethyl ester in 100 ml of anhydrous dimethylformamide. 250 MHz FT-$^1$H-NMR (CDCl$_3$): 2.18, 2.21, 2.30, 2.32 (4s, 6H, dihydropyridyl-CH$_3$); 2.80–3.10 (m, 2H, phenyl-CH$_2$); 3.65, 3.75 (2s, 6H, —COOCH$_3$); 4.74–4.94 (m, 1H, —CON—CH—); 4.83 (s, 1H, 4-dihydropyridyl-H), 5.5–5.8 (m, 3H, —NH and —OH); 6.52–6.78 (m, 4H, hydroxyphenyl-H); 7.30–8.06 (m, 4H, nitrophenyl-H).

EXAMPLE 17

Analogously to the process described in Example 1, a racemic 1:1 diastereoisomeric mixture of 1,4-dihydro-2,6-dimethyl-3-methoxycarbonyl-4-(3-nitrophenyl)-pyridine-5-carboxylic acid N-(1-benzyl-oxycarbonyl-1-benzyl)-amide is obtained, in amorphous form, from a mixture of 20 g of 1,4-dihydro-2,6-dimethyl-4-(3-nitrophenyl)-pyridine-3,5-dicarboxylic acid 3-(1-benzotriazolyl)-ester-5-methyl ester, 11.5 g of D,L-α-phenylglycine benzyl ester hydrochloride and 5.2 ml of N-ethylmorpholine in 90 ml of anhydrous dimethylformamide. 250 MHz FT-$^1$H-NMR (CDCl$_3$): 2.23, 2.26, 2.32, 2.33 (4s, 6H, dihydropyridyl-H); 3.63, 2.67 (2s, 3H, —COOCH$_3$); 4.96, 5.09 (2s, 2H, —COOCH$_2$); 5.15, 5.16 (2s, 1H, 4-dihydropyridyl-H); 5.55 (m, 1H, —N—

CH—); 5.6, 5.65 (2s, 1H, 1-dihydropyridyl-H); 6.32, 6.40 (2d, 1H, —CONH—); 7.04–8.12 (m, 14H, phenyl-H).

EXAMPLE 18

Analogously to the process described in Example 1 there is obtained, from a mixture of 20 g of 4-(2-difluoromethoxyphenyl)-1,4-dihydro-2,6-dimethylpyridine-3,5-dicarboxylic acid 3-(1-benzotriazolyl)-ester-5-methyl ester, 7 g of L-valine ethyl ester hydrochloride and 4.9 ml of N-ethylmorpholine in 150 ml of anhydrous dimethylformamide, a 1:1 diastereoisomeric mixture of (4R)- and (4S)-4-(2-difluoromethoxyphenyl)-1,4-dihydro-2,6-dimethyl-3-methoxycarbonylpyridine-5-carboxylic acid N-[(1S)-1-ethoxycarbonyl-2-methyl-1-propyl]-amide which, after recrystallisation from a mixture of diethyl ether and diisopropyl ether, melts at from 98° to 99°.

The starting material can be obtained as follows: Analogously to the process described in Example 1, 4-(2-difluoromethoxyphenyl)-1,4-dihydro-2,6-dimethylpyridine-3,5-dicarboxylic acid 3-(1-benzotriazolyl)-ester-5-methyl ester is obtained as a crude product, in amorphous form, from a mixture of 17 g of 4-(2-difluoromethoxyphenyl)-1,4-dihydro-2,6-dimethylpyridine-3,5-dicarboxylic acid monomethyl ester [manufactured analogously to the method described in EP 11.706; melting point 150° to 152°], 8 g of 1-hydroxybenzotriazole and 11 g of N,N'-dicyclohexyl carbodiimide in 150 ml of anhydrous dimethylformamide, and is used in the subsequent reaction without being purified further.

EXAMPLE 19

Analogously to the process described in Example 1, a 1:1 diastereoisomeric mixture of (4R)- and (4S)-1,4-dihydro-2,6-dimethyl-3-methoxy-carbonyl-4-(3-nitrophenyl)-pyridine-5-carboxylic acid N-[(1S)-1-ethoxycarbonyl-1-benzyl]-amide is obtained, in the form of a resinous crude product, from a mixture of 20 g of 1,4-dihydro-2,6-dimethyl-4-(3-nitrophenyl)-pyridine-3,5-dicarboxylic acid 3-(1-benzotriazolyl)-ester-5-methyl ester, 8.9 g of L-α-phenylglycine ethyl ester hydrochloride and 5.2 ml of N-ethylmorpholine in 150 ml of anhydrous dimethylformamide.

In order to separate the diastereoisomers, a mixture of ethyl acetate and diisopropyl ether is added to the crude product and the whole is stirred for 1 hour at from 0° to 5°; a first diastereoisomer crystallises which is uniform in configuration, melts at from 193° to 194° and exhibits a specific rotation of $[\alpha]_{436}^{20} = -66°$ (c=0.7, ethanol).

In order to isolate the second diastereoisomer, the mother liquor is concentrated by evaporation under reduced pressure and the residue is purified by chromatography over approximately 100 times the amount of silica gel (elution with a 1:1 mixture of hexane and ethyl acetate). The eluate is concentrated by evaporation under reduced pressure and the residue is recrystallised from a mixture of ethyl acetate and hexane. The resulting second diastereoisomer melts at from 139° to 140° and exhibits a specific rotation of $[\alpha]_D^{20} = -46°$ (c=0.8, ethanol); according to the ¹H-NMR spectrum this crystalline form is also contaminated with approximately 20% of the first diastereoisomer.

EXAMPLE 20

Analogously to the process described in Example 1, a 1:1 diastereoisomeric mixture of (4R)- and (4S)-1,4-dihydro-2,6-dimethyl-3-methoxy-carbonyl-4-(3-nitrophenyl)-pyridine-5-carboxylic acid N-[(1R)-1-ethoxycarbonyl-1-benzyl]-amide is obtained, in the form of a highly viscous crude product, from a mixture of 20 g of 1,4-dihydro-2,6-dimethyl-4-(3-nitrophenyl)-pyridine-3,5-dicarboxylic acid 3-(1-benzotriazolyl)-ester-5-methyl ester, 8.9 g of D-α-phenylglycine ethyl ester hydrochloride and 5.2 ml of N-ethylmorpholine in 150 ml of anhydrous dimethylformamide.

In order to separate the diastereoisomers, a mixture of ethyl acetate and diisopropyl ether is added to the crude product and the whole is left to stand at from 0° to 50° for 16 hours, in the course of which a first diastereoisomer crystallises. The crystals are filtered with suction and recrystallised from ethyl alcohol. The resulting first diastereoisomer is uniform in configuration; it melts at from 196° to 197° and exhibits a specific rotation of $[\alpha]_{436}^{20} = +61°$ (c=0.34, ethanol).

In order to isolate the second diastereoisomer, the mother liquor is concentrated by evaporation under reduced pressure and the residue is purified by chromatography over approximately 100 times the amount of silica gel (elution with a 1:1 mixture of hexane and ethyl acetate). The eluate is concentrated by evaporation under reduced pressure and the residue is recrystallised twice from a mixture of ethyl acetate and diethyl ether.

The resulting second diastereoisomer melts at from 134° to 135° and exhibits a specific rotation of $[\alpha]_D^{20} = -45°$, (c=0.7, ethanol); according to the ¹H-NMR spectrum this crystalline form is contaminated with approximately 15% of the first diastereoisomer.

EXAMPLE 21

A mixture of 5.9 g of 1,4-dihydro-2,6-dimethyl-4-(3-nitrophenyl)-pyridine-3,5-dicarboxylic acid 3-(1-benzotriazolyl)-ester-5-isopropyl ester, 5.34 g of L-phenylalanyl-L-phenylalanine-0-(2-trimethylsilylethyl)-ester hydrochloride and 1.5 ml of N-ethylmorpholine in 90 ml of anhydrous dimethylformamide is stirred for 15 hours at 80° under a nitrogen atmosphere. 200 ml of water are added to the reaction mixture while cooling with ice. The crystals are filtered off and washed with water and dried under reduced pressure. This crude product is purified by chromatography over approximately 100 times the amount of silica gel (elution with a 1:1 mixture of chloroform and methanol). The resulting amorphous product is a 1:1 diastereoisomeric mixture of N-[1,4-dihydro-2,6-dimethyl-3-isopropoxycarbonyl-4-(3-nitrophenyl)-5-pyridoyl]-L-phenylalanyl-L-phenylalanine-0-(2-trimethylsilylethyl)-ester; it exhibits a thin-layer chromatographic $R_f$ value of 0.65 in the elution system toluene/-acetone 1:1.

In order to cleave the 2-trimethylsilylethyl ester, a mixture of 3.6 g of the ester obtained above is stirred for 20 minutes at 20° in 34 ml of a 0.7M solution of tetraethylammonium fluoride in dimethyl sulphoxide. The clear reaction solution is cooled in an ice bath, and 24 ml of 1N hydrochloric acid and 150 ml of water are added. The precipitate that has formed is filtered off and the filtration residue is washed with water and dried under reduced pressure over potassium hydroxide. The crude product is taken up in ethyl acetate and filtered and the filtrate is concentrated by evaporation under reduced pressure. As a result of trituration of the viscous residue with diisopropyl ether, amorphous N-[1,4-dihydro-2,6-dimethyl-3-isopropoxycarbonyl-4-(3-nitrophenyl)-5-pyridoyl]-L-phenylalanyl-L-phenylalanine is obtained in the form of a diastereoisomeric mixture; it exhibits a thin-layer chromatographic $R_f$ value of 0.70 in the elution system acetonitrile/water 3:1.

The starting material can be obtained as follows: 3.50 ml of N-ethylmorpholine and 6.7 g of N,N-dicyclohexyl carbodiimide are added at 0° to a mixture of 8.2 g of N-benzyloxycarbonyl-L-phenylalanine and 8.3 g of L-phenylalanine-(2-trimethylsilylethyl)-ester hydrochloride in 125 ml of anhydrous dichloromethane. The whole is stirred for 1 hour at 0° and then for a further 15 hours at room temperature. The reaction mixture is filtered and the filtrate is diluted with 80 ml of dichloromethane. The dichloromethane solution is washed with 1N citric acid, 1N sodium bicarbonate and water. The organic phase is dried over sodium sulphate and filtered and the filtrate is concentrated by evaporation under reduced pressure. The residue crystallises from a mixture of ethyl acetate and petroleum ether. The resulting N-benzyloxycarbonyl-L-phenylalanyl-L-phenylalanine-0-(2-trimethylsilylethyl)-ester melts at from 89° to 90°.

1.80 g of this intermediate are subjected to hydrogenolysis in 20 ml of methanol in the presence of 180 mg of 10% palladium-on-carbon, the pH value of the reaction mixture being kept constant at 4.0 with 1N hydrochloric acid. Once the reaction is complete, the catalyst is filtered off and the filtrate is concentrated by evaporation under reduced pressure, L-phenylalanyl-L-phenylalanine-0-(2-trimethylsilylethyl)-ester hydrochloride being obtained in the form of a white foam. The product exhibits a thin-layer chromatographic $R_f$ value of 0.75 in the elution system chloroform/methanol 8:2.

EXAMPLE 22

10 g of (−)-(4R)-1,4-dihydro-2,6-dimethyl-3-methoxycarbonyl-4-(3-nitrophenyl)-pyridine-5-carboxylic acid N-[(1S)-1-ethoxycarbonyl-2-methyl-1-propyl]-amide are stirred in a mixture of 300 ml of methanol and 300 ml of 0.1N sodium hydroxide solution for 15 hours at room temperature. The clear yellow solution is then concentrated to dryness by evaporation under reduced pressure. The solid yellowish residue is stirred in 160 ml of 1N sodium hydroxide solution at room temperature, treated with active carbon and filtered, and the filtrate is acidified with 200 ml of 1N hydrochloric acid. The acid that has precipitated is filtered off, washed several times with water and dried for 12 hours at 50° C. under a high vacuum. The (−)-(4R)-1,4-dihydro-2,6-dimethyl-3-methoxycarbonyl-4-(3-nitrophenyl)-pyridine-5-carboxylic acid N-[(1S)-1-carboxy-2-methyl-1-propyl]-amide melts at from 217° to 219°; $[\alpha]_D^{20} = -8.1°$ (c=0.87, ethanol)

EXAMPLE 23

In a manner entirely analogous to that described in Example 22, but starting from (+)-(4S)-1,4-dihydro-2,6-dimethyl-3-methoxycarbonyl-4-(3-nitrophenyl)-pyridine-5-carboxylic acid N-[(1S)-1-ethoxycarbonyl-2-methyl-1-propyl]-amide, there is obtained (+)-(4S)-1,4-dihydro-2,6-dimethyl-3-methoxycarbonyl-4-(3-nitrophenyl)-pyridine-5-carboxylic acid N-[(1S)-1-carboxy-2-methyl-1-propyl]-amide, which melts, with decomposition, at from 198° to 202° and the specific rotation of which is $[\alpha]_D^{20} = +84.1°$ (c=1.0, ethanol).

EXAMPLE 24

47 g of (−)-(4R)-1,4-dihydro-2,6-dimethyl-3-methoxycarbonyl-4-(3-nitrophenyl)-pyridine-5-carboxylic acid N-[(1S)-1-carboxy-2-methyl-1-propyl]-amide are heated at 80° for 15 hours under nitrogen with 30.5 g of 0-n-butyl-N,N'-dicyclohexylisourea [manufacture according to the method described in Chem. Ber. 99, 1479, (1966)] in 400 ml of ethyl acetate. The initial suspension becomes clear and, after an hour, N,N'-dicyclohexylurea begins to be precipitated. The urea is filtered off and washed with ethyl acetate and the filtrate is concentrated by evaporation. The residue is chromatographed over a 1050 g flash column in a mixture of ethyl acetate/hexane 3:7 as eluant. The product that has been purified in this manner (51 g) is recrystallised from 60 ml of absolute ether and washed with a mixture of ether/hexane 95:5. The resulting (−)-(4R)-1,4-dihydro-2,6-dimethyl-3-methoxycarbonyl-4-(3-nitrophenyl)-pyridine-5-carboxylic acid N-[(1S)-1-(n-butoxycarbonyl)-2-methyl-1-propyl]-amide has a melting point of from 69° to 70°; $[\alpha]_D^{20} = -22°$ (c=0.6, ethanol).

EXAMPLE 25

In a manner entirely analogous to that described in Example 24, but starting from (+)-(4S)-1,4-dihydro-2,6-dimethyl-3-methoxycarbonyl-4-(3-nitrophenyl)-pyridine-5-carboxylic acid N-[(1S)-1-carboxy-2-methyl-1-propyl]-amide, there is obtained (+)-(4S)-1,4-2,6-dimethyl-3-methoxycarbonyl-4-(3-nitrophenyl)-pyridine-5-carboxylic acid N-[(1S)-1-(n-butoxycarbonyl)-2-methyl-1-propyl]-amide having a melting point of from 144° to 145°; $[\alpha]_D^{20} = +66°$ (c=1.0, ethanol).

EXAMPLE 26

In a manner entirely analogous to that described in Example 24, but starting from the corresponding O-substituted N,N'-dicyclohexylisoureas [manufactured according to the method described in Chem. Ber. 99, 1479, (1966) and Liebigs Ann. Chemie 597, 235 (1956)], the compounds listed below are obtained in a form that is uniform in configuration:

(a) (−)-(4R)-1,4-dihydro-2,6-dimethyl-3-methoxycarbony-4-(3-nitrophenyl)-pyridine-5-carboxylic acid N-[(1S)-1-(n-hexyloxycarbonyl)-2-methyl-1-propyl]-amide; $[\alpha]_D^{20} = -15.7° \pm 3.2°$ (c=0.31, ethanol).

(b) (−)-(4R)-1,4-dihydro-2,6-dimethyl-3-methoxycarbonyl-4-(3-nitrophenyl)-pyridine-5-carboxylic acid N-[(1S)-1-(benzyloxycarbonyl)-2-methyl-1-propyl]-amide; $[\alpha]_D^{20} = -15.5°$ (c=0.9, ethanol).

(c) (−)-(4R)-1,4-dihydro-2,6-dimethyl-3-methoxy-4-(3-nitrophenyl)-pyridine-5-carboxylic acid N-{(1S)-1-[3-(4-methyl-1-piperazinyl)-1-propoxy]-carbonyl-2-methyl-1-propyl}-amide; $[\alpha]_D^{20} = -10.0$ (c=0.93, ethanol).

(d) (−)-(4R)-1,4-dihydro-2,6-dimethyl-3-methoxycarbon-4-(3-nitrophenyl)-pyridine-5-carboxylic acid N-{(1S)-1-[3-(4-benzyl-1-piperazinyl)-1-propoxy]-carbonyl-2-methyl-1-propyl}-amide; $[\alpha]_D^{20} = -12.7°$ (c=0.6, ethanol).

EXAMPLE 27

In a manner entirely analogous to that described in Example 24, but starting from a 1:1 diastereoisomeric mixture of (4R)- and (4S)-1,4-dihydro-2,6-dimethyl-3-methoxycarbonyl-4-(3-nitrophenyl)-pyridine-5-carboxylic acid N-[(1S)-1-carboxy-2-methyl-1-propyl]-amide and the corresponding 0-substituted N,N'-dicyclohexylisoureas, the compounds listed below are obtained in the form of amorphous 1:1 diastereoisomeric mixtures:

(a) (4R)- and (4S)-1,4-dihydro-2,6-dimethyl-3-methoxycarbonyl-4-(3-nitrophenyl)-pyridine-5-carboxylic acid N-[(1S)-1-(2-dimethylamino-1-ethoxy)-carbonyl-2-methyl-1-propyl]-amide. 250 MHz FT-$^1$H-NMR (CDCl$_3$): 0.75 (m, 6H, —CH$_3$); 2.1 (m, 1H, —CH); 2.3 (m, 12H, dihydropyridyl —CH$_3$; —N—CH$_3$); 2.55, 4.20 (2m, 4H, —O—CH$_2$—CH$_2$—N); 3.65 (2s, 3H, COOCH$_3$); 4.55 (m, 1H, —CON—CH); 5.0 (2s, 1H, 4-dihydropyridyl-H); 5.65 (2s, 1H, 1-dihydropyridyl-H); 5.85 (2d, 1H, —CONH); 7.4–8.2 (m, 4H, phenyl-H).

(b) (4R)- and (4S)-1,4-dihydro-2,6-dimethyl-3-methoxycarbonyl-4-(3-nitrophenyl)-pyridine-5-carboxylic acid N-[(1S)-1-(3-dimethylamino-1-propoxy)-carbonyl-2-methyl-1-propyl]-amide. 250 MHz FT-$^1$H-NMR (CDCl$_3$): 0.75 (m, 6H, —CH$_3$); 1.8 (m, 2H, —CH$_2$—); 2.1 (m, 1H, —CH—); 2.2–2.4 (m, 15H, dihydropyridyl-CH$_3$; —CH$_2$—N—CH$_3$); 3.65 (2s, 6H, COOCH$_3$); 4.15 (m, 2H, COOCH$_2$); 4.5 (m, 1H, —CON—CH); 5.0 (2s, 1H, 4-dihydropyridyl-H); 5.6 (2s, 1H, 1-dihydropyridyl-H); 5.8 (2d, 1H, —CONH); 7.4–8.2 (m, 4H, phenyl-H).

(c) (4R)- and (4S)-1,4-dihydro-2,6-dimethyl-3-methoxycarbonyl-4-(3-nitrophenyl)-pyridine-5-carboxylic acid N-{(1S)-1-[2-(4-morpholino)-1-ethoxy]-carbonyl-2-methyl-1-propyl}-amide. 250 MHz FT-$^1$H-NMR (CDCl$_3$): 0.75 (m, 6H, —CH$_3$); 2.1 (m, 1H, —CH—); 2.3 (m, 6H, dihydropyridyl-CH$_3$); 2.4–2.65 (m, 6H, —N—CH$_2$); 3.7 (m, 7H, —COOCH$_3$; —O—CH$_2$—); 4.05–4.4 (m, 2H, COOCH$_2$); 4.55 (m, 1H, CON—CH—); 5.0 (2s, 1H, 4-dihydropyridyl-H), 5.62 (2s, 1H, 1-dihydropyridyl-H); 5.8 (2d, 1H, —CONH); 7.4–8.2 (m, 4H, phenyl-H).

(d) (4R)- and (4S)-1,4-dihydro-2,6-dimethyl-3-methoxycarbonyl-4-(3-nitrophenyl)-pyridine-5-carboxylic acid N-[(1S)-1-(2-methoxy-1-ethoxy)-carbonyl-2-methyl-1-propyl]-amide. 250 MHz FT-$^1$H-NMR (CDCl$_3$): 0.75 (m, 6H, —CH$_3$); 2.1 (m, 1H, —CH—); 2.2-2.36 (4s, 6H, dihydropyridyl—CH$_3$); 3.36 (2s, 3H, —OCH$_3$); 3.55 (m, 2H, —OCH$_2$—); 3.62 (2s, 3H, —COOCH$_3$); 4.25 (m, 2H, —COOCH$_2$—); 4.60 (m, 1H, —CON—CH—); 4.98 (2s, 1H, 4-dihydropyridyl-H); 5.6 (2s, 1H, 1-dihydropyridyl-H); 5.8 (2d, 1H, —CONH—); 7.4–8.2 (m, 4H, phenyl-H).

EXAMPLE 28

Analogously to the process described in Example 1, a racemic 1:1 diastereoisomeric mixture of 1,4-dihydro-2,6-dimethyl-3-methoxycarbonyl-4-(3-nitrophenyl)-pyridine-5-carboxylic acid N-[1-(carbamoylmethoxycarbonyl)-1-phenylmethyl]-amide is obtained, in the form of a resinous intermediate, from a mixture of 54.5 g of 1,4-dihydro-2,6-dimethyl-4-(3-nitrophenyl)-pyridine-3,5-dicarboxylic acid 3-(1-benzotriazolyl)-ester-5-methyl ester, 31 g of D,L-phenylglycine carbamoylmethyl ester hydrochloride [manufactured analogously to the method described in Tetrahedron Lett. 24, 5219 (1983)] and 16.2 ml of N-ethylmorpholine in 300 ml of anhydrous dimethylformamide.

16 g of the above intermediate are stirred for 2 hours at room temperature in a mixture of 67 ml of 0.5N sodium hydroxide solution and 50 ml of N,N-dimethylformamide. The dark reaction solution is then concentrated to dryness by evaporation under reduced pressure. The dark residue is dissolved in 100 ml of 0.02N sodium hydroxide solution, washed several times with ethyl acetate, treated additionally with active carbon and filtered and the filtrate is acidified with 2N hydrochloric acid. The acid that has precipitated is filtered off and the filtration residue is washed several times with water and dried for 12 hours at 50° under a high vacuum. The resulting racemic 1:1 diastereoisomeric mixture of 1,4-dihydro-2,6-dimethyl-3-methoxycarbonyl-4-(3-nitrophenyl)-pyridine-5-carboxylic acid N-(1-carboxy-1-phenylmethyl)-amide melts at from 126° to 128°.

EXAMPLE 29

(a) 4 g of 1,4-dihydro-2,6-dimethyl-3-methoxycarbonyl-4-(3-nitrophenyl)-pyridine-5-carboxylic acid N-(1-carboxy-1-phenylmethyl)-amide (racemic 1:1 diastereoisomeric mixture) are heated at 80° for 15 hours under a nitrogen atmosphere with 2.6 g of 0-(2-dimethylaminoethyl)-N,N'-dicyclohexylisourea [manufactured analogously to the method described in Liebigs Ann. Chem. 597, 235 (1956)] in 60 ml of ethyl acetate. The urea that has precipitated is filtered off and the filtrate is concentrated by evaporation under reduced pressure. The residue is purified by chromatography over approximately 100 times the amount of silica gel (elution with a 9:1 mixture of methylene chloride and methanol). One equivalent of 1.7N alcoholic hydrochloric acid is added to the resulting crude base and the solution is concentrated by evaporation under reduced pressure. The resinous residue is stirred in a mixture of 20 ml of ethyl acetate and 50 ml of diethyl ether in an ice bath, 1,4-dihydro-2,6-dimethyl-3-methoxycarbonyl-4-(3-nitrophenyl)-pyridine-5-carboxylic acid N-[1-(2-dimethylamino-1-ethoxy)-carbonyl-1-phenylmethyl]-amide hydrochloride crystallising. This 1:1 diastereoisomeric mixture melts at from 100° to 112° with decomposition.

(b) In a manner entirely analogous to that described in (a), but starting from 0-(2-morpholinoethyl)-N,N'-dicyclohexylisourea [manufactured analogously to the method described in Liebigs Ann. Chem. 597, 235 (1956)], 1,4-dihydro-2,6-dimethyl-3-methoxycarbonyl-4-(3-nitrophenyl)-pyridine-5-carboxylic acid N-{1-[2-(4-morpholino)-1-ethoxy]-carbonyl-1-phenylmethyl}-amide hydrochloride is obtained in the form of a 1:1 diastereoisomeric mixture which melts at from 127° to 129°.

EXAMPLE 30

(a) Analogously to the process described in Example 1 there is obtained, from a mixture of 50 g of 1,4-dihydro-2,6-dimethyl-4-(3-nitrophenyl)-pyridine-3,5-dicarboxylic acid 3-(1-benzotriazolyl)-ester-5-methyl ester, 20.4 g of L-isoleucine ethyl ester hydrochloride and 12.2 ml of N-ethylmorpholine in 300 ml of anhydrous dimethylformamide, (+)-(4S)-1,4-dihydro-2,6-dimethyl-3-methoxycarbonyl-4-(3-nitrophenyl)-pyridine-5-carboxylic acid N-[(1S,2S)-1-ethoxycarbonyl-2-methyl-1-butyl]-amide which, after recrystallisation from a mixture of methyl acetate and diisopropyl ether, melts at from 170° to 171°. This diastereoisomer ($\alpha$) is uniform in configuration and exhibits a specific rotation of $[\alpha]_D^{20} = +93°$ (c=0.44, ethanol).

Analogously to the process described in Example 1, (4R)-1,4-dihydro-2,6-dimethyl-3-methoxycarbonyl-4-(3-nitrophenyl)-pyridine-5-carboxylic acid N-[(1S,2S)-1-ethoxycarbonyl-2-methyl-1-butyl]-amide is isolated from the mother liquor. As a result of trituration of the amorphous crude product using diethyl ether, this diastereoisomer (δ) crystallises, and, after further recrystallisation from a mixture of ethyl acetate and n-hexane, melts at from 117° to 118°. The specific rotation is $[\alpha]_D^{20} = +5°$ (c=0.91, ethanol); according to the $^1$H-

NMR spectrum this δ-diastereoisomer also contains approximately 25% of the above α-diastereoisomer.

(b) In a manner entirely analogous to that described in (a), but starting from L-isoleucine methyl ester hydrochloride, a 1:1 diastereoisomeric mixture of (4R)- and (4S)-1,4-dihydro-2,6-dimethyl-3-methoxycarbonyl-4-(3-nitrophenyl)-pyridine-5-carboxylic acid N-[(1S,2S)-methoxycarbonyl-2-methyl-1-butyl]-amide having a melting point of from 139° to 140° is obtained

EXAMPLE 31

Analogously to the process described in Example 2 there is obtained, from a mixture of 9.4 g of N-acetoacetyl-α-aminocyclohexylcarboxylic acid ethyl ester [manufactured analogously to the method described in Pharm. Acta Helv. 38, 616 (1963)], 4.1 g of 3-aminocrotonic acid methyl ester and 5.5 g of 3-nitrobenzaldehyde in 70 ml of ethanol, amorphous 1,4-dihydro-2,6-dimethyl-3-methoxycarbonyl-4-(3-nitrophenyl)-pyridine-5-carboxylic acid N-(1-ethoxycarbonyl-1-cyclohexyl)amide which crystallises when stirred with diethyl ether, melting point 166°–168°.

EXAMPLE 32

Analogously to the process described in Example 2 there is obtained, from a mixture of 8.1 g of N-acetoacetyl-α,α-diphenylglycine ethyl ester [manufactured analogously to the method described in Pharm. Acta Helv. 38, 616 (1963)], 2.8 g of 3-aminocrotonic acid methyl ester and 3.6 g of 3-nitrobenzaldehyde in 45 ml of ethanol, amorphous 1,4-dihydro-2,6-dimethyl-3-methoxycarbonyl-4-(3-nitrophenyl)-pyridine-5-carboxylic acid N-(1-ethoxycarbonyl-1,1-diphenylmethyl)-amide. 250 MHz FT-$^1$H-NMR (CDCl$_3$): 1.15 (t, 3H, —COO—C—CH$_3$); 2.18, 2.30 (2s, 6H, dihydropyridyl-H); 3.61 (s, 3H, —COOCH$_3$); 4.19 (q, 2H, —COO—CH$_2$—); 5.05 (s, 1H, 4-dihydropyridyl-H); 5.72 (s, 1H, 1-dihydropyridyl-H); 6.96 (s, 1H, —CONH—); 7.1–8.18 (m, 14H, phenyl-H).

EXAMPLE 33

Analogously to the process described in Example 1, racemic 1,4-dihydro-2,6-dimethyl-3-methoxycarbonyl-4-(3-nitrophenyl)-pyridine-5-carboxylic-acid N-{1-[2-(N-tert.-butoxycarbonylamino)-4-thiazolyl]-1-ethoxycarbonylmethyl}-amide is obtained, in the form of a resinous intermediate, from 7.9 g of 1,4-dihydro-2,6-dimethyl-4-(3-nitrophenyl)-pyridine-3,5-dicarboxylic acid 3-(1-benzotriazolyl)-ester-5-methyl ester and 5 g of D,L-α-[2-(N-tert.-butoxycarbonylamino)-4-thiazolyl]-glycine ethyl ester in 30 ml of anhydrous dimethylformamide.

This intermediate is dissolved in 40 ml of icecold glacial acetic acid that is saturated with hydrochloric acid, and stirred at 0° for 1½ hours. The cold reaction solution is then neutralised with 2N sodium hydroxide solution and the crude product is extracted several times with ethyl acetate. The combined organic extracts are concentrated by evaporation under reduced pressure, 1,4-dihydro-2,6-dimethyl-3-methoxycarbonyl-4-(3-nitrophenyl)-pyridine-5-carboxylic acid N-[1-(2-amino-4-thiazolyl)-1-ethoxycarbonylmethyl]-amide remaining behind in the form of an amorphous 1:1 diastereoisomeric mixture. 250 MHz FT-$^1$H-NMR (CDCl$_3$): 1.2 (2t, 3H, —COO—C—CH$_3$); 2.32 (2d, 6H, dihydropyridyl-CH$_3$); 2.65 (2s, 3H, —COOCH$_3$); 4.15 (2m, 2H, —COO—CH$_2$—); 5.0 (2s, 1H, 4-dihydropyridyl-H); 5.06 (s, 1H, —NH$_2$); 5.40 (2s, 1H, —N—CH—); 5.60 (2s, 1H, 1-dihydropyridyl-H); 6.42 (2s, 1H, thiazolyl-H); 6.50, 6.65 (2d, 1H, —CONH); 7.35–8.20 (m, 4H, phenyl-H).

EXAMPLE 34

(a) A solution of 7 g of 1,4-dihydro-2,6-dimethyl-3-methylsulphonyl-4-(3-nitrophenyl)-pyridine-5-carboxylic acid [manufactured analogously to EP 11.706; melting point 228°–229°], 3.4 g of 1-hydroxybenzotriazole and 4.6 g of N,N'-dicyclohexyl carbodiimide in 100 ml of anhydrous dimethylformamide is left to stand for 16 hours at from 0° to 5° under a nitrogen atmosphere. The N,N'-dicyclohexylurea that has crystallised out is filtered off. 4 g of L-valine ethyl ester hydrochloride and 2.8 ml of N-ethylmorpholine are added to the yellow filtrate and the whole is stirred for 16 hours at 80° under a nitrogen atmosphere. While cooling with ice-water, 250 ml of ice-water are added to the yellow reaction mixture and the whole is stirred for a further 1 hour at from 0° to 5°, the crude product crystallising. After filtration, the filtration residue is washed with 1 litre of water and dried in vacuo. The resulting 1:1 diastereoisomeric mixture of (4R)- and (4S)-1,4-dihydro-2,6-dimethyl-3-methylsulphonyl-4-(3-nitrophenyl)-pyridine-5-carboxylic acid N-[(1S)-1-ethoxycarbonyl-2-methyl-1-propyl]-amide melts, after recrystallisation from ethyl acetate, at from 191° to 192°.

(b) In a manner entirely analogous to (a), but starting from D-valine ethyl ester hydrochloride, there is obtained a 1:1 diastereoisomeric mixture of (4R)- and (4S)-1,4-dihydro-2,6-dimethyl-3-methylsulphonyl-4-(3-nitrophenyl)-pyridine-5-carboxylic acid N-[(1R)-1-ethoxycarbonyl-2-methyl-1-propyl]-amide which melts at from 188° to 191°.

EXAMPLE 35

A mixture of 44.6 g of (S)-N-(3-nitrobenzylideneacetoacetyl)-α-aminoisovaleric acid ethyl ester and 14.1 g of 3-aminocrotonic acid methyl ester in 350 ml of ethanol is stirred for 16 hours at 80° under a nitrogen atmosphere. The yellow reaction mixture is concentrated by evaporation under reduced pressure and the residue is purified by chromatography over approximately 100 times the amount of silica gel (elution with a 7:3 mixture of n-hexane and ethyl acetate). The resulting resinous crude product is a 1:1 diastereoisomeric mixture of (4R)- and (4S)-1,4-dihydro-2,6-dimethyl-3-methoxycarbonyl-4-(3-nitrophenyl)-pyridine- 5-carboxylic acid N-[(1S)-1-ethoxycarbonyl-2-methyl-1-propyl]-amide.

The diastereoisomers are separated as described in Example 1.

The starting material can be manufactured as follows: HCl gas is introduced over a period of 2 hours at from 5° to 15° into a solution of 21.6 g of 3-nitrobenzaldehyde and 32.8 g of (S)-N-acetoacetyl-α-aminoisovaleric acid ethyl ester [manufactured analogously to the method described in Pharm. Acta Helv. 38, 616 (1963)] in 140 ml of anhydrous toluene. The whole is then stirred for a further 2 hours at room temperature and the reaction mixture is concentrated by evaporation under reduced pressure. The residue is stirred for 4 hours at 80° under a water-jet vacuum, hydrochloric acid being separated off. After recrystallisation from a mixture of 24 ml of tetrahydrofuran and 180 ml of diethyl ether, the resulting crude (S)-N-(3-nitrobenzylideneacetoacetyl)-α-aminoisovaleric acid ethyl ester melts at from 114° to 116°.

EXAMPLE 36

In a manner entirely analogous to that described in Example 35, but starting from 2-nitrobenzaldehyde, there is obtained initially, in the form of an intermediate, (S)-N-(2-nitrobenzylideneacetoacetyl)-α-aminoisovaleric acid ethyl ester [melting point 106°–107°] and, from this intermediate, by condensation with 3-aminocrotonic acid methyl ester, a resinous diastereoisomeric mixture of (4R)- and (4S)-1,4-dihydro-2,6-dimethyl-3-methoxycarbonyl-4-(2-nitrophenyl)-pyridine-5-carboxylic acid N-[(1S)-1-ethoxycarbonyl-2-methyl-1-propyl]-amide.

The diastereoisomers are separated as described in Example 1, there being obtained, after recrystallisation from a mixture of ethyl acetate and hexane, a diastereoisomer (α) which is uniform in configuration and the specific rotation of which is $[\alpha]_D^{20} = -363.5° \pm 6.4°$ (c=0.15, ethanol) and which melts at from 179° to 180°. The amorphous diastereoisomer (β) which, according to the $^1$H-NMR spectrum, also contains approximately 15% of the above α-diastereoisomer, is isolated from the mother liquor. 250 MHz FT-$^1$H-NMR (CDCl$_3$) spectrum of the diastereoisomer β: 0.52, 0.6 (2d, 6H, —CH$_3$); 1.3 (t, 3H, —O—CH$_2$—); 1.98 (m, 1H, —CH—); 2.28, 2.48 (2s, 6H, dihydropyridyl—CH$_3$); 3.55 (s, 3H, —COOCH$_3$); 4.12 (m, 2H, —COOCH$_2$—); 4.6 (m, 1H, —CON—CH—); 5.7, 5.83 (2s, 2H, 1- or 4-dihydropyridyl-H); 7.25–7.8 (m, 4H, phenyl-H).

EXAMPLE 37

Analogously to the process described in Example 1 there is obtained, from 18.7 g of 1,4-dihydro-2,6-dimethyl-4-(3-nitrophenyl)-pyridine-3,5-dicarboxylic acid 3-(1-benzotriazolyl)-ester-5-methyl ester and 6.7 g of L-valine amide in 100 ml of anhydrous dimethylformamide, a 1:1 diastereoisomeric mixture of (4R) and (4S)-1,4-dihydro-2,6-dimethyl-3-methoxycarbonyl-4-(3-nitrophenyl)-pyridine-5-carboxylic acid N-[(b 1S)-1-carbamoyl-2-methyl-1-propyl]-amide which, after recrystallisation from a mixture of acetone and diethyl ether, melts at from 190° to 191°.

EXAMPLE 38

(a) While cooling, 1.9 ml of chloroformic acid isobutyl ester are added dropwise in the course of 10 minutes to a mixture of 8.6 g of 1,4-dihydro-2,6-dimethyl-3-methoxycarbonyl-4-(3-nitrophenyl)-pyridine-5-carboxylic acid N-(1-carboxy-2-methyl-1-propyl)-amide (racemic 1:1 diastereoisomeric mixture) and 2.5 ml of N-ethylmorpholine in 50 ml of anhydrous tetrahydrofuran in such a manner that the temperature does not exceed −15°. The whole is then stirred for 10 minutes at from −20° to −15° and then, while cooling, 2.8 ml of 2-(2-aminoethyl)-pyridine are added dropwise in such a manner that the temperature does not exceed −10°. Once the addition is complete, the reaction mixture is allowed to warm up to room temperature and is stirred for a further 3 hours, after which it is concentrated by evaporation under reduced pressure. The resinous residue is purified by chromatography over approximately 100 times the amount of silica gel (elution with a 95:5 mixture of methylene chloride and methanol). The resulting resinous 1,4-dihydro-2,6-dimethyl-3-methoxycarbonyl-4-(3-nitrophenyl)-pyridine-5-carboxylic acid N-{1-[2-(2-pyridyl)-1-ethylamino]carbonyl-2-methyl-1-propyl}-amide crystallises from a mixture of methylene chloride and diethyl ether in the form of a 1:4 diastereoisomeric mixture having a melting point of from 158° to 160°.

(b) In a manner entirely analogous to that described in (a), but starting from N-methylbenzylamine, there is obtained a 1:4 diastereoisomeric mixture of 1,4-dihydro-2,6-dimethyl-3-methoxycarbonyl-4-(3-nitrophenyl)-pyridine-5-carboxylic acid N-[1-(N-benzylmethylamino)-carbonyl-2-methyl-1-propyl]-amide having a melting point of from 94° to 95°.

(c) In a manner entirely analogous to that described in (a), but starting from N-benzylpiperazine, there is obtained an amorphous 3:7 diastereoisomeric mixture of 1,4-dihydro-2,6-dimethyl-3-methoxycarbonyl-4-(3-nitrophenyl)-pyridine-5-carboxylic acid N-[1-(4-benzyl-1-piperazinyl)-carbonyl-2-methyl-1-propyl]-amide. 250 MHz FT-$^1$H-NMR (CDCl$_3$): 0.6–0.85 (m, 6H, —CH$_3$); 1.85 (m, 1H, —CH—), 2.2–2.35 (4s, 6H, dihydropyridyl-CH$_3$); 2.4 (m, 4H, —N—CH$_2$); 3.44–3.66 (m, 9H, N—CH$_2$, —COOCH$_3$); 4.85 (m, 1H, —CON—CH—); 5.0 (2s, 1H, 4-dihydropyridyl-H); 5.55, 5.6 (2s, 1H, 1-dihydropyridyl-H); 6.15, 6.30 (2d, 1H, -CONH); 7.25–8.18 (m, 9H, phenyl-H).

(d) In a manner entirely analogous to that described in (a), but starting from N-diphenylmethylpiperazine, there is obtained an amorphous 3:7 diastereoisomeric mixture of 1,4-dihydro-2,6-dimethyl-3-methoxycarbonyl-4-(3-nitrophenyl)-pyridine-5-carboxylic acid N-[1-(4-diphenylmethyl-1-piperazinyl)-carbonyl-2-methyl-1-propyl]-amide. 250 MHz FT-$^1$H-NMR (CDCl$_3$): 0.55–0.9 (m, 6H, —CH$_3$); 1.8 (m, 1H, —CH—); 2.15–2.45 (4s, 10H, dihydropyridyl-CH$_3$, —N—CH$_2$—); 3.4–3.6 (m, 4H, $$-\overset{\overset{\displaystyle O}{\|}}{C}-N-CH_2;$$

3.55, 3.65 (2s, 3H, —COOCH$_3$); 4.2 (2s, 1H, —CHPh$_2$); 4.8 (m, 1H, —CON—CH); 4.98 (2s, 1H, 4-dihydropyridyl-H); 5.45, 5.55 (2S, 1H, 1-dihydro-pyridyl-H); 6.1, 6.28 (2d, 1H, —CONH—); 7.15–8.15 (m, 14H, phenyl-H).

(e) In a manner entirely analogous to that described in (a), but starting from n-butylamine, there is obtained an amorphous 1:2 diastereoisomeric mixture of 1,4-dihydro-2,6-dimethyl-3-methoxycarbonyl-4-(3-nitrophenyl)-pyridine-5-carboxylic acid N-[1-(n-butylaminocarbonyl)-2-methyl-1-propyl]-amide. 250 MHz FT-$^1$H-NMR (CDCl$_3$): 0.65–0.98 (m, 9H, —CH3); 1.25–1.55 (m, 4H, —CH$_2$—CH$_2$); 1.95 (m, 1H, —CH—); 2.18–2.38 (4s, 6H, dihydropyridyl-CH$_3$); 3.22 (m, 2H, —CON—CH$_2$—); 3.65 (2s, 3H, —COOCH$_3$); 4.15 (m, 1H, —CON—CH—); 4.98 (2s, 1H, 4-dihydropyridyl-H); 5.55, 5.65 (2s, 1H, 1-dihydropyridyl-H); 5.8, 6.05 (2m, 2H, —CONH); 7.4–8.15 (m, 4H, phenyl-H).

(f) In a manner entirely analogous to that described in (a), but starting from N-n-heptylmethylamine, there is obtained an amorphous 1:1 diastereoisomeric mixture of 1,4-dihydro-2,6-dimethyl-3-methoxycarbonyl-4-(3-nitrophenyl)-pyridine-5-carboxylic acid N-[1-(N-methyl-n-heptylaminocarbonyl)-2-methyl-1-propyl]-amide. 250 MHz FT-$^1$H-NMR (CDCl$_{13}$): 0.63–0.98 (m, 9H, —CH$_3$); 1.2–1.6 (m, 10H, —CH$_2$—); 1.9 (m, 1H, —CH—); 2.15, 2.35 (2d, 6H, dihydropyridyl-CH$_3$); 2.89, 3.02 (2d, 3H, N-CH$_3$); 3.1–3.55 (m, 2H, N-CH$_2$); 3.6, 3.65 (2s, 3H, COOCH$_3$); 4.8 (m, 1H, —CON—CH—); 5.0 (2s, 1H, 4-dihydropyridyl-H); 5.52, 5.62 (2s, 1H, 1-dihydro-pyridyl-H); 6.08–6.30 (m, 1H, —CONH); 7.38–8.18 (m, 4H, phenyl-H).

EXAMPLE 39

In a manner entirely analogous to that described in Example 22, but starting from (+)-(4S)-1,4-dihydro-2,6-dimethyl-3-methoxycarbonyl-4-(3-nitrophenyl)-pyridine-5-carboxylic acid N-[(1R)-1-ethoxycarbonyl-2-methyl-1-propyl]-amide, there is obtained (+)-(4S)-1,4-dihydro-2,6-dimethyl-3-methoxycarbonyl-4-(3-nitrophenyl)-pyridine-5-carboxylic acid N-[(1R)-1-carboxy-2-methyl-1-propyl]-amide which melts at from 216° to 218° and the specific rotation of which $[\alpha]_D^{20} = +8.0°$ (c=1.0, ethanol).

EXAMPLE 40

In a manner entirely analogous to that described in Example 22, but starting from (−)-(4R)-1,4-dihydro-b 2,6-dimethyl-3-methoxycarbonyl-4-(3-nitrophenyl)-pyridine-5-carboxylic acid N-[(1R)-1-ethoxycarbonyl-2-methyl-1-propyl]-amide, there is obtained (−)-(4R)-1,4-dihydro-2,6-dimethyl-3-methoxycarbonyl-4-(3-nitrophenyl)-pyridine-5-carboxylic acid N-[(1R)-1-carboxy-2-methyl-1-propyl]-amide which melts at from 121° to 122°, with decomposition, and the specific rotation of which is $[\alpha]_D^{20} = -77.0°$ (c=1.0, ethanol).

EXAMPLE 41

In a manner entirely analogous to that described in Example 24, but starting from (+)-(4S)-1,4-dihydro-2,6-dimethyl-3-methoxycarbonyl-4-(3-nitrophenyl)-pyridine-5-carboxylic acid N-[(1R)-1-carboxy-2-methyl-1-propyl]-amide, there is obtained (+)-(4S)-1,4-dihydro-2,6-dimethyl-3-methoxycarbonyl-4-(3-nitrophenyl)-pyridine-5-carboxylic acid N-[(1R)-1-(n-butoxycarbonyl)-2-methyl-1-propyl]-amide which melts at from 67° to 68° and has a specific rotation of $[\alpha]_D^{20} = +21°$ (c=1.0, ethanol).

EXAMPLE 42

In a manner entirely analogous to that described in Example 24, but starting from (−)-(4R)-1,4-dihydro-2,6-dimethyl-3-methoxycarbonyl-4-(3-nitrophenyl)-pyridine-5-carboxylic acid N-[(1R)-1-carboxy-2-methyl-1-propyl]-amide, there is obtained (−)-(4R)-1,4-dihydro-2,6-dimethyl-3-methoxycarbonyl-4-(3-nitrophenyl)-pyridine-5-carboxylic acid N-[(1R)-1-(n-butoxycarbonyl)-2-methyl-1-propyl]-amide which melts at from 143° to 144° and the specific rotation of which is $[\alpha]_D^{20} = -65°$ (c=1.0, ethanol).

EXAMPLE 43

In a manner entirely analogous to that described in Example 35, but starting from 3-aminocrotonic acid ethyl ester, an approximately 1:1 diastereoisomeric mixture is obtained in the form of a resinous crude product. By means of crystallisation from a 2:1 mixture of ethyl acetate and diisopropyl ether, crystalline (−)-(4R-1,4-dihydro-2,6-dimethyl-3-enthoxycarbonyl-4-(3-nitrophenyl)-pyridine-5-carboxylic acid N-[(1S)-1-ethoxycarbonyl-2-methyl-1-propyl]-amide is obtained in a form that is uniform in configuration. It melts at from 169° to 170°. Its specific rotation is $[\alpha]_D^{20} = -46.6°$ (c=0.476, ethanol). From the mother liquor crystalline (+)-(4S)-1,4-dihydro-2,6-dimethyl-3-ethoxycarbonyl-4-(3-nitrophenyl)-pyridine-5-carboxylic acid N-[(1S)-1-ethoxycarbonyl-2-methyl-1-propyl]-amide is isolated; m.p. 135°–136°; $[\alpha]_D^{20} = +40.6°$ (c=0.94, ethanol).

EXAMPLE 44

In a manner entirely analogous to that described in Example 35, but starting from 3-aminocrotonic acid n-propyl ester, an approximately 1:1 diastereoisomeric mixture is obtained in the form of a resinous crude product. By means of crystallisation from a 2:1 mixture of ethyl acetate and diisopropyl ether, crystalline (−)-(4R)-1,4-dihydro-2,6-dimethyl-3-(n-propyloxycarbonyl)-4-(3-nitrophenyl)-pyridine-5-carboxylic acid N-[(1S)-1-ethoxycarbonyl-2-methyl-1-propyl]-amide is obtained in a form that is uniform in configuration. It melts at from 148° to 149°. Its specific rotation is $[\alpha]_D^{20} = -19.9°$ (c=0.55, ethanol). From the mother liquor crystalline (+)-(4S)-1,4-dihydro-2,6-dimethyl-3-(n-propyloxycarbonyl)-4-(3-nitrophenyl)-pyridine-5-carboxylic acid N-[(1S)-1-ethoxycarbonyl-2-methyl-1-propyl]-amide is isolated; m.p. 119°–121°; $[\alpha]_D^{20} = +70.9°$ (c=0.67, ethanol).

EXAMPLE 45

2.4 g of (S)-N-(3-nitrobenzylideneacetoacetyl)-α-aminoisovaleric acid butyl ester and 0.92 g of amidinoacetic acid methyl ester hydrochloride [see Ann. Chem. 1977, 1895] are dissolved in 6 ml of absolute methanol and, under reflux, a sodium methoxide solution prepared from 140 mg of sodium and 6 ml of absolute methanol is added dropwise thereto and the whole is heated at reflux for a further 1 hour. The sodium chloride that has precipitated is filtered off, the filtrate is concentrated by evaporation under reduced pressure and the residue is chromatographed over a medium-pressure column in a 1:1 mixture of hexane and ethyl acetate. The resulting amorphous 2-amino-1,4-dihydro-6-methyl-3-methoxycarbonyl-4-(3-nitrophenyl)-pyridine-5-carboxylic acid N-[(1S)-1-(n-butoxycarbonyl)-2-methyl-1-propyl]-amide is an S,4R:S,4S diastereoisomeric mixture and exhibits the following NMR data: 250 MHz FT-$^1$H-NMR (CDCl$_3$): 0.80 (2m, 6H, isopropyl-CH$_3$); 0.95 (2t, 3H, —COO—C—C—C—CH$_3$); 1.34, 1.60 (2m, 4H, —COO—C—CH$_2$—CH$_2$—C); 2.06 (m, 1H, —CHC$_2$); 2.10, 2.18 (2s, 6H, dihydropyridyl—CH$_3$); 2.62 (2s, 6H, —COOCH$_3$); 4.1 (m, 2H, —COOCH$_2$—C—); 4.46 (m, 1H,

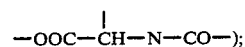

4.80, 4.86 (2s, 1H, 4-dihydropyridyl-H); 5.84, 5.98 (2d, 1H, —NH—); 6.35 (1s, 2H, —NH$_2$); 6.76, 6.90 (2d, 1H, —CO—NH—); 7.40, 7.64, 8.20, 8.14 (m, t, d, m, 4H, phenyl-H).

The starting material can be manufactured as follows:

Analogously to the process described in Example 35 there is obtained, from a mixture of 14.0 g of (S)-N-acetoacetyl-α-aminoisovaleric acid butyl ester, manufactured analogously to the method described in Pharm. Acta Helv. 38, 616 (1963), and 8.2 g of 3-nitrobenzaldehyde in 50 ml of toluene, (S)-N-(3 -nitrobenzylideneacetoacetyl)-α-aminoisovaleric acid butyl ester.

EXAMPLE 46

26.5 g of 3-ethoxycarbonyl-2-diethoxymethyl-1,4-dihydro-6-methyl-4-(3-nitrophenyl)-pyridine-5-carboxylic acid N-[(1S)-1-ethoxycarbonyl-2-methyl-1-propyl]-amide are dissolved in 160 ml of acetone, and 26.5 ml of 6N hydrochloric acid are added. The whole is stirred for one hour at room temperature, the reaction solution is concentrated by evaporation under reduced pressure and the residue is chromatographed over a flash column in an 8:2 mixture of hexane and ethyl acetate. The resulting amorphous 3-ethoxycarbonyl-1,4-dihydro-2-formyl-6-methyl-4-(3-nitrophenyl)-pyridine-5-carboxylic acid N-[(1S-α-1-ethoxycarbonyl-2-methyl-1-propyl]-amide is an S,4R:S,4S diastereoisomeric mixture and exhibits the following NMR data: 250 MHz FT-¹H-NMR (CDCl₃): 0.80 (2m, 6H, —C(CH₃)₂); 1.26 (2m, 6H, —COO—C—CH₃); 2.06 (m, 1H, —CHC₂); 2.28, 2.36 (2s, 3H, dihydropyridyl-CH₃); 4.18 (m, 4H, —COO—CH₂—C); 4.53 (m, 1H,

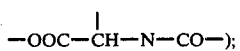

5.00, 5.16 (2s, 1H, 4-dihydropyridyl-H); 5.72, 5.88 (2d, 1H, —NH—); 6.83, 6.90 (2s, 1H, —CO—NH—); 7.47, 7.70, 8.10, 8.18 (t, m, m, m, 4H, phenyl-H).

The starting material can be synthesised as follows:

A mixture of 29.0 g of (S)-N-(3-nitrobenzylideneacetoacetyl)-α-aminoisovaleric acid ethyl ester (see Example 35), 17.4 g of 3-amino-4,4-diethoxycrotonic acid ethyl ester, 50 g of molecular sieve (Union Carbide 3A)° and 160 ml of absolute alcohol is heated under reflux for 40 hours. The molecular sieve is filtered off, the filtrate is concentrated by evaporation under reduced pressure and the residue is chromatographed over a flash column in a 1:1 mixture of hexane and ethyl acetate. The resulting 3-ethoxycarbonyl-2-diethoxymethyl-1,4-dihydro-6-methyl-4-(3-nitrophenyl)-pyridine-5-carboxylic acid N-[(1S)-1-ethoxycarbonyl-2-methyl-1-propyl]-amide is reacted further immediately.

EXAMPLE 47

6.5 g of 3-ethoxycarbonyl-1,4-dihydro-2-formyl-6-methyl-4-(3-nitrophenyl)-pyridine-5-carboxylic acid N-[(1S)-1-ethoxycarbonyl-2-methyl-1-propyl]-amide are dissolved in 100 ml of alcohol and, while stirring at 0°, 0.65 g of sodium borohydride is added in the course of 5 minutes and the whole is stirred for 30 minutes at room temperature to complete the reaction. The whole is then acidified with 2N hydrochloric acid and concentrated to dryness by evaporation under reduced pressure. The residue is partitioned between water and ethyl acetate, the organic phase is dried and concentrated by evaporation and the residue is chromatographed over a medium-pressure column in a 1:1 mixture of hexane and ethyl acetate. The resulting amorphous 3-ethoxycarbonyl-1,4-dihydro-2-hydroxymethyl-6-methyl-4-(3-nitrophenyl)-pyridine-5-carboxylic acid N-[(1S)-1-ethoxycarbonyl-2-methyl-1-propyl]-amide is an S,4R:S,4S diastereoisomeric mixture and exhibits the following NMR data: 250 MHz FT-¹H-NMR (CDCl₃): 0.74 (2m, 6H, —C(CH₃)₂); 1.28 (2m, 6H, —COO—C—CH₃); 2.06 (m, 1H, —CHC₂); 2.26, 2.32 (2s, 3H, dihydropyridyl-CH₃); 2.76, 2.96 (2m, 1H, —OH); 4.1 (m, 4H, —COO—CH₂—C—); 4.50 (m, 1H,

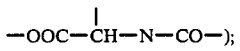

4.68, 4.84 (2m, 2H, —CH₂—O); 4.98, 5.02 (2s, 1H, 4-dihydropyridyl-H); 5.72, 5.98 (2d, 1H, —NH—); 6.96, 7.12 (2s, 1H, —CO—NH—); 7.46, 7.67, 8.05, 8.16 (t, t, m, m, 4H, phenyl-H).

EXAMPLE 48

A mixture of 12.0 g of 3-ethoxycarbonyl-1,4-dihydro-2-formyl-6-methyl-4-(3-nitrophenyl)-pyridine-5-carboxylic acid N-[(1S)-1-ethoxycarbonyl-2-methyl-1-propyl]-amide, 2.0 g of hydroxylamine hydrochloride, 1.6 g of sodium carbonate and 150 ml of absolute alcohol are stirred for 2½ hours at room temperature. The whole is then concentrated by evaporation under reduced pressure and the residue is partitioned between water and ethyl acetate. The organic phase is dried and concentrated by evaporation and the resulting oxime is reacted further immediately.

A mixture of 12.5 g of 3-ethoxycarbonyl-1,4-dihydro-2-hydroxyiminomethyl-6-methyl-4-(3-nitrophenyl)-pyridine-5-carboxylic acid N-[(1S)-1-ethoxycarbonyl-2-methyl-1-propyl]-amide, 12.9 g of N,N-dicyclohexyl carbodiimide and 50 ml of absolute pyridine are heated under reflux for 5 hours. The solution is then concentrated by evaporation under reduced pressure and the residue is partitioned between 1N hydrochloric acid and ethyl acetate, and the urea that has precipitated is filtered off. The organic phase is washed with water and brine, dried and concentrated by evaporation. The residue is chromatographed over a medium-pressure column in a mixture of hexane and ethyl acetate. The resulting amorphous 3-ethoxycarbonyl-2-cyano-1,4-dihydro-6-methyl-4-(3-nitrophenyl)-pyridine-5-carboxylic acid N-[(1S)-1-ethoxycarbonyl-2-methyl-1-propyl]-amide is an S,4R:S,4S diastereoisomeric mixture and exhibits the following NMR data: 250 MHz FT-¹H-NMR (CDCl₃): 0.74 (2m, 6H, —C(CH₃)₂); 1.26 (m, 6H, —COO—C—CH₃); 2.05 (m, 1H, —CHC₂); 2.24, 2.32 (2s, 3H, dihydropyridyl-CH₃); 4.2 (m, 4H, —COO—CH₂—C—); 4.50 (m, 1H,

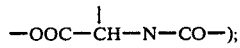

5.06, 5.10 (2s, 1H, 4-dihydropyridyl-H); 5.74, 5.86 (2d, 1H, —NH—); 6.26, 6.38 (2s, 1H, —CO—NH—); 7.50, 7.70, 8.14 (t, m, m, 4H, phenyl-H).

EXAMPLE 49

In a manner entirely analogous to that described in Example 26, the compounds listed below are obtained in a form that is uniform in configuration:

(a) (−)-(4R)-1,4-dihydro-2,6-dimethyl-3-methoxycarbonyl-4-(3-nitrophenyl)-pyridine-5-carboxylic acid N-[(1S)-1-(2-furylmethoxycarbonyl)-2-methyl-1-propyl]-amide; $[\alpha]_D^{20} = -38.4°$ (c=0.91, ethanol); m.p. 76°–78°.

(b) (−)-(4R)-1,4-dihydro-2,6-dimethyl-3-methoxycarbonyl-4-(3-nitrophenyl)-pyridine-5-carboxylic acid N-[(1S)-1-isopropyloxycarbonyl-2-methyl-1-propyl]-amide; $[\alpha]_D^{20} = -18.5°$ (c=0.56, ethanol); m.p. 166°–167°.

(c) (4R)-1,4-dihydro-2,6-dimethyl-3-methoxycarbonyl-4-(3-nitrophenyl)-pyridine-5-carboxylic acid N-[(1S)-1-(tert.-butyloxycarbonyl)-2-methyl-1-propyl]-amide; m.p. 163°–164°.

EXAMPLE 50

Analogously to the process described in Example 1 there is obtained, from a mixture of 43.3 g 1,4-dihydro- 2,6-dimethyl-4-(3-nitrophenyl)-pyridine-3,5-dicarboxylic acid 3-(1-benzotriazolyl)-ester-5-methyl ester, 19.6 g L-N-methylvaline ethyl ester hydrochloride and 12.8 ml of N-ethylmorpholine in 250 ml of anhydrous dimethylformamide, a ca. 1:1 diastereoisomeric mixture of (4R)- and (4S)-1,4-dihydro-2,6-dimethyl-3-methoxycarbonyl-4-(3-nitrophenyl)-pyridine-5-carboxylic acid N-methyl-N-[(1S)-1-ethoxycarbonyl-2-methyl-1-propyl]-amide which, after recrystallisation from diethyl ether, melts at from 158° to 159°.

EXAMPLE 51

A solution of 11.3 g of the cesium salt of (−)-(4R)-1,4-dihydro-2,6-dimethyl-3-methoxycarbonyl-4-(3-nitrophenyl)-pyridine-5-carboxylic acid N-[(1S)-1-carboxy-2-methyl-1-propyl]-amide and 1.9 ml 3-bromo-1-propanol in 60 ml dry N,N-dimethylformamide is stirred for 16 h at 50° under exclusion of moisture. The yellow reaction mixture is evaporated to dryness. The residue is purified by chromatography over a 200 g flash column in ethyl acetate as eluant. The product that has been purified in this manner is recrystallised from a mixture of ethylacetate/ether 1:10. The resulting (−)-(4R)-1,4-dihydro-2,6-dimethyl-3-methoxycarbonyl-4-(3-nitrophenyl)-pyridine-5-carboxylic acid N-≡(1S)-1-[(3-hydroxy-1-propoxy)-carbonyl]-2-methyl-1-propyl}-amide has a melting point of from 149° to 150°; $[\alpha]_D^{20} = -19.1°$ (c=0.89, ethanol).

The starting material is prepared as follows:

4.3 g of (−)-(4R)-1,4-dihydro-2,6-dimethyl-3-methoxycarbonyl-4-(3-nitrophenyl)-pyridine-5-carboxylic acid N-(1S)-1-carboxy-2-methyl-1-propyl]-amide are suspended in 20 ml of ethanol and 5 ml of water. Ca. 10.0 ml of a 20% aqueous solution of cesium carbonate are added in several portions while cooling with ice-water until a pH of 7.0 is reached. The now clear, faintly yellow solution is concentrated by evaporation under reduced pressure at a bath temperature of 40°, treated three times with 20 ml of toluene and each time evaporated to dryness to yield the cesium salt of the above mentioned acid.

We claim:
1. Compounds of the formula I

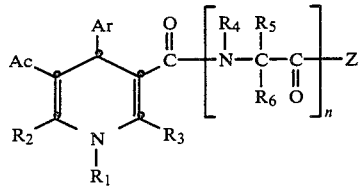

in which n represents 1, 2 or 3, Ar represents a carbocyclic or heterocyclic aryl radical, Ac represents the acyl radical of an acid, Z represents a radical —OR$_7$ or —NR$_8$R$_9$, R$_1$ represents hydrogen, unsubstituted or substituted lower alkyl, a carbocyclic or heterocyclic aryl radical or free, etherified or esterified hydroxy, R$_2$ and R$_3$, independently of one another, each represents hydrogen, unsubstituted or substituted lower alkyl, formyl or functionally modified formyl, carboxy or functionally modified carboxy, a carbocyclic or heterocyclic aryl radical or unsubstituted or mono- or di-substituted amino, R$_4$ represents hydrogen or lower alkyl, R$_5$ and R$_6$, independently of one another, each represents hydrogen, unsubstituted or substituted lower alkyl or a carbocyclic or heterocyclic aryl radical, R$_7$, R$_8$ and R$_9$, independently of one another, each represents hydrogen, unsubstituted or substituted alkyl or a carbocyclic or heterocyclic aryl radical; in which R$_1$ and R$_2$ together or R$_1$ and R$_3$ together may represent unsubstituted or substituted lower alkylene in which a carbon atom is optionally replaced by a hetero atom, in which R$_4$ and R$_5$ together, and likewise R$_5$ and R$_6$ together and/or R$_8$ and R$_9$ together, independently of one another, may represent unsubstituted or substituted lower alkylene in which a carbon atom may have been replaced by a hetero atom, optical isomers of compounds of the formula I, mixtures of these optical isomers, and salts of such compounds that have a salt-forming grouping.

2. Compounds of the formula I according to claim 1, in which n represents 1, 2 or 3, Ar represents a monocyclic or bicyclic carbocyclic aryl radical or a five or six-membered monocyclic heteroaryl radical which contains as ring members from one up to and including four ring nitrogen atoms, one ring oxygen or ring sulphur atom, or one or two ring nitrogen atoms together with one ring oxygen atom or one ring sulphur atom and which optionally contains a fused-on benzo ring, and is phenyl, naphthyl, pyrryl, pyrazolyl, imidazolyl, triazolyl, tetrazolyl, furyl, thienyl, isoxazolyl, oxazolyl, oxadiazolyl, isothiazolyl, thiazolyl, thiadiazolyl, pyridyl, pyridazinyl, pyrimidinyl, pyrazinyl, triazinyl, indolyl, isoindolyl, benzoxadiazolyl, benzothiadiazolyl, benzimidazolyl, benzofuranyl, benzothienyl, quinolinyl or isoquinolinyl, it being possible for ring carbon atoms in these radicals to be optionally substituted by lower alkyl, lower alkenyl, lower alkynyl, lower alkylene, cycloalkyl, phenyl, phenyl-lower alkyl, phenyl-lower alkoxy and/or by phenyl-lower alkylthio (it being optionally possible for lower alkyl, phenyl, phenyl-lower alkyl, phenyl-lower alkoxy and/or phenyl-lower alkylthio to contain as substituent(s) hydroxy, lower alkoxy, halo-lower alkoxy, lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkylcarbamoyl and/or cyano, and for the cyclic radicals also to contain as substituent lower alkyl which may itself be substituted as indicated) and/or by hydroxy, lower alkoxy, halo-lower alkoxy, lower alkenyloxy, lower alkynyloxy, lower alkylenedioxy, lower alkanoyloxy, halogen, nitro, amino, lower alkylamino, di-lower alkylamino, N-lower alkyl-N-phenyl-lower alkylamino, lower alkyleneamino, oxa-lower alkyleneamino, thia-lower alkyleneamino and/or aza-lower alkyleneamino, (in which the aza-nitrogen atom may be substituted by lower alkyl, phenyl or phenyl-lower alkyl, which substituents may contain hydroxy, lower alkoxy, halo-lower alkoxy, lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkylcarbamoyl and/or cyano as substituent(s)), and/or by lower alkanoylamino, azido, carboxy, lower alkoxycarbonyl, carbamoyl, N-lower alkylcarbamoyl, N,N-di-lower alkylcarbamoyl, cyano, sulpho, aminosulphonyl, lower alkylthio, lower alkylsulphinyl and/or by lower alkylsulphonyl, and/or for ring nitrogen atoms in these radicals to be optionally substituted by lower alkoxycarbonyl or by lower alkyl which may optionally contain hydroxy, lower alkoxy, halo-lower alkoxy, lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkylcarbamoyl or cyano as substituent, or by hydroxy or oxido, the radical Ac represents lower alkanoyl, benzoyl that is unsubstituted or substituted by lower alkyl, lower alkoxy, nitro and/or by halogen, lower alkylsulphonyl, phenylsulphonyl that is unsubstituted or substituted by lower alkyl, lower alkoxy, nitro and/or by halogen, lower alkoxycarbonyl, hydroxy-lower alkoxycarbonyl, lower alkoxy-lower alkoxycarbonyl, amino-lower alkoxycarbonyl, lower alkylamino-lower alkoxycarbonyl, N,N-di-lower alkylamino-lower alkoxycarbonyl, N-lower alkyl-N-phenyl-lower alkylamino-lower alkoxycarbonyl, N,N-lower alkyleneamino-lower alkoxycarbonyl, morpholino-lower alkoxycarbonyl, thiomorpholino-lower alkoxycarbonyl, piperazino-lower alkoxycarbonyl, 4-lower alkylpiperazino-lower alkoxycarbonyl, phenyl-, thienyl-, furyl-, pyrryl- or pyridyl-lower alkoxycarbonyl that is unsubstituted or substituted by lower alkyl, lower alkoxy, nitro and/or by halogen, lower alkenyloxy- or lower alkynyloxy-carbonyl, carbamoyl, N-lower alkylcarbamoyl, N,N-di-lower alkylcarbamoyl, N-hydroxycarbamoyl, N,N-lower alkylenecarbamoyl, morpholinocarbonyl, thiomorpholinocarbonyl, piperazinocarbonyl, 4-lower alkyl-piperazinocarbonyl, 5-tetrazolyl, or unsubstituted or lower alkyl- or phenyl-substituted 4,5-dihydro-2-oxazolyl or 5,6-dihydro-4H-1,3-oxazin-2-yl, Z represents a radical —OR$_7$ or —NR$_8$R$_9$, R$_1$ represents hydrogen; lower alkyl that is optionally substituted by lower alkylamino, di-lower alkylamino, lower alkyleneamino, morpholino, thiomorpholino, piperazino, which optionally contains lower alkyl or lower alkanoyl as substituent at a nitrogen atom, carboxy, functionally modified carboxy, lower alkoxy, lower alkoxy-lower alkoxy or phenyl, which itself optionally contains lower alkyl, lower alkoxy, halogen and/or nitro as substituent(s), or by N-pyrrolyl, N-imidazolyl, N-pyrazolyl, N-indolyl or by N-isoindolyl; phenyl which is optionally substituted in the same manner as a phenylower alkyl radical R$_1$; hydroxy, lower alkoxy or phenyl-lower alkoxy, R$_2$ and R$_3$, independently of one another, each represents hydrogen, lower alkyl which is optionally substituted by hydroxy, by lower alkoxy, which optionally contains amino, lower alkylamino, di-lower alkylamino or acylamino as substituent, by acyloxy or by phenyl, or each represents formyl, di-lower alkyl acetal or dithioacetal, lower alkylene acetal or dithioacetal, functionally modified carboxy; phenyl which optionally contains as substituent(s) lower alkyl, hydroxy, lower alkoxy, lower alkylenedioxy, halogen, nitro, amino, lower alkylamino, di-lower alkylamino, lower alkanoylamino, carboxy, functionally modified carboxy and/or lower alkylthio; pyrryl, furyl, thienyl or pyridyl, these radicals optionally being substituted in the same manner as a phenyl radical R$_2$ or R$_3$; amino, lower alkylamino or di-lower alkylamino, R$_4$ represents hydrogen or lower alkyl, R$_5$ represents hydrogen, lower alkyl that is unsubstituted or substituted by free or etherified hydroxy, by free or etherified mercapto, which may optionally be oxidised, by carboxy, by functionally modified carboxy, by amino which itself optionally contains lower alkyl, carboxy, functionally modified carboxy or acyl as substituent, by a monocyclic or bicyclic carbocyclic aryl radical or by a five- or six-membered heteroaryl radical according to the above definition of Ar, or represents phenyl that is unsubstituted or substituted by free or etherified hydroxy, lower alkyl, nitro, amino, lower alkylamino, di-lower alkylamino, lower alkanoylamino and/or by halogen, or a monocyclic five- or six-membered heteroaryl radical according to the above definition of Ar that is optionally substituted in the same manner, R$_6$ represents hydrogen, lower alkyl, phenyl-lower alkyl that is unsubstituted or substituted by free or etherified hydroxy, lower alkyl, nitro, amino, lower alkylamino, di-lower alkylamino, lower alkanoylamino and/or by halogen, phenyl that is unsubstituted or substituted in the same manner as a phenyl-lower alkyl radical R$_6$, or a monocyclic five- or six-membered heteroaryl radical that is optionally substituted in the same manner, and R$_7$, R$_8$ and R$_9$, independently of one another, each represents hydrogen; alkyl that is optionally substituted by amino, lower alkylamino, di-lower alkylamino, lower alkyleneamino, oxa-, thia- or aza-lower alkyleneamino in which the aza-nitrogen atom optionally carries lower alkyl or lower alkanoyl as substituent, acylamino, free or etherified hydroxy or by a carbocyclic aryl radical or heteroaryl radical as defined above for the group Ar; or each represents a carbocyclic aryl radical or heteroaryl radical as defined above for the group Ar; in which R$_1$ and R$_2$ together or R$_1$ and R$_3$ together may represent C$_3$–C$_5$–lower alkylene in which the carbon atom bonded directly to the C2- or C6-carbon atom of the 1,4-dihydropyridine ring is optionally replaced by an oxygen or sulphur atom or by a nitrogen atom that is substituted by hydrogen or lower alkyl, in which R$_4$ and R$_5$ may together represent lower alkylene or oxa-, thia- or aza-lower alkylene each of which is unsubstituted or substituted by free or etherified hydroxy, amino, lower alkylamino, di-lower alkylamino and/or by halogen, and at the aza-nitrogen atom also by lower alkyl, in which R$_5$ and R$_6$ may together represent lower alkylene or aza-, oxa or thia-lower alkylene, these radicals being optionally substituted at carbon atoms by free or etherified hydroxy, amino, lower alkylamino, di-lower alkylamino, halogen, carboxy and/or by functionally modified carboxy and at the aza-nitrogen atom optionally by lower alkyl, and in which R$_8$ and R$_9$ may together represent lower alkylene or aza-, oxa- or thia-lower alkylene, these radicals being optionally substituted at carbon atoms by free or etherified hydroxy, amino, lower alkylamino, di-lower alkylamino, halogen, carboxy, functionally modified carboxy or by a five- or six-membered monoaza-, diaza- or triaza-heteroaryl radical which is optionally completely or partially saturated and is optionally substituted at carbon atoms by oxo and optionally substituted at the aza-nitrogen atoms by lower alkyl or phenyl, which may itself contain lower alkyl, halogen, lower alkoxy and/or nitro as substituent(s); and being optionally substituted at the aza-nitrogen atom by lower alkyl which itself optionally contains a carbocyclic aryl radical or heteroaryl radical as defined above for the group Ar and/or free or etherified hydroxy, acyloxy, amino, lower alkylamino and/or di-lower alkylamino as substituent(s); by acyl or phenyl, which may itself contain lower alkyl, halogen, lower alkoxy and/or nitro as substituent(s), optical isomers of compounds of the formula I, mixtures of these optical isomers, and salts of such compounds having salt-forming groups.

3. Compounds of the formula I according to claim 1, in which n represents 1, 2 or 3, Ar represents phenyl which is optionally substituted by lower alkyl, phenyl, phenyl-lower alkyl, phenyl-lower alkoxy and/or by phenyl-lower alkylthio (it being possible for these radicals themselves to contain hydroxy, lower alkoxy, lower alkylenedioxy, halogen, carboxy, lower alkoxycarbonyl and/or cyano as substituent(s), and for the cyclic radicals also to contain lower alkyl as substituent) and/or by hydroxy, lower alkoxy, halo-lower alkoxy, lower alkylenedioxy, halogen, nitro, amino, lower alkylamino, di-lower alkylamino, lower alkanoylamino, carboxy, lower alkoxycarbonyl, carbamoyl, cyano, sulpho, aminosulphonyl, lower alkylthio, lower alkylsulphinyl and/or by lower alkylsulphonyl, or represents pyrryl, furyl, thienyl, pyridyl, benzoxadiazolyl or benzothiadiazolyl, which radicals are optionally substituted in the same manner as a phenyl radical Ar and contain as substituent(s) especially lower alkyl, lower alkoxy, halogen and/or phenyl which is optionally substituted by lower alkyl, lower alkoxy, halogen and/or by nitro, the radical Ac represents lower alkanoyl, lower alkylsulphonyl, lower alkoxycarbonyl, hydroxy-lower alkoxycarbonyl, lower alkoxy-lower alkoxycarbonyl, N,N-di-lower alkylamino-lower alkoxycarbonyl, N-lower alkyl-N-phenyl-lower alkylamino-lower alkoxycarbonyl, N,N-lower alkyleneamino-lower alkoxycarbonyl, (4-morpholino)-lower alkoxycarbonyl, lower alkenyloxy or lower alkynyloxy-carbonyl, carbamoyl, N-lower alkylcarbamoyl, N,N-di-lower alkylcarbamoyl, N,N-lower alkylenecarbamoyl, 4-morpholinocarbonyl or 4-lower alkyl-1-piperazinocarbonyl, Z represents a radical —$OR_7$ or —$NR_8R_9$, $R_1$ represents hydrogen, lower alkyl, di-lower alkylamino-lower alkyl, lower alkyleneamino-lower alkyl, (4-morpholino)-lower alkyl, carboxy-lower alkyl, lower alkoxycarbonyl-lower alkyl or lower alkoxy-lower alkoxy-lower alkyl, wherein di-lower alkylamino, lower alkyleneamino and 4-morpholino are separated from the ring nitrogen atom by at least two carbon atoms, or represents phenyl-lower alkyl, phenyl, hydroxy or lower alkoxy, $R_2$ and $R_3$, independently of one another, each represents lower alkyl which is optionally substituted by hydroxy, by lower alkoxy, which optionally contains amino, lower alkylamino or di-lower alkylamino as substituent, by lower alkanoyloxy or by phenyl, or each represents formyl, di-lower alkyl acetal or dithioacetal, lower alkylene acetal or di-thioacetal, cyano, phenyl, thienyl or amino, $R_4$ represents hydrogen or lower alkyl, $R_5$ represents hydrogen, lower alkyl that is unsubstituted or substituted by hydroxy, lower alkoxy, mercapto, lower alkylthio, carboxy, carbamoyl, amino, lower alkanoylamino, carbamoylamino, guanidino, phenyl, which may for its part be hydroxy- and/or halo-substituted, by imidazolyl or by indolyl, or represents phenyl that is unsubstituted or substituted by hydroxy, lower alkoxy, lower alkyl, nitro, amino, lower alkylamino, di-lower alkylamino and/or by halogen, or represents pyrryl, pyrazolyl, imidazolyl, triazolyl, tetrazolyl, furyl, thienyl, isoxazolyl, oxazolyl, oxadiazolyl, isothiazolyl, thiazolyl, thiadiazolyl, pyridyl, pyridazinyl, pyrimidinyl, pyrazinyl or triazinyl, each of which is unsubstituted or substituted as indicated for a phenyl radical $R_5$, $R_6$ represents hydrogen, lower alkyl, phenyl-lower alkyl, phenyl-lower alkyl that is unsubstituted or substituted by hydroxy, lower alkoxy, lower alkyl, nitro, amino, lower alkylamino, di-lower alkylamino and/or by halogen, or phenyl, pyrryl, pyrazolyl, imidazolyl, triazolyl, tetrazolyl, furyl, thienyl, isoxazolyl, oxazolyl, oxadiazolyl, isothiazolyl, thiazolyl, thiadiazolyl, pyridyl, pyridazinyl, pyrimidinyl, pyrazinyl or triazinyl, each of which is unsubstituted or substituted as indicated for a phenyl-lower alkyl radical $R_6$, and $R_7$, $R_8$ and $R_9$, independently of one another, each represents hydrogen, lower alkyl, or lower alkyl that is substituted by amino, lower alkylamino, di-lower alkylamino, lower alkyleneamino, oxathia- or aza-lower alkyleneamino, in which the aza-nitrogen atom is optionally lower alkyl-substituted, lower alkanoylamino, hydroxy, lower alkoxy or by phenyl, which may be unsubstituted or may itself be substituted by amino, lower alkylamino, di-lower alkylamino, lower alkyleneamino, hydroxy, lower alkoxy, halogen and/or by nitro, or lower alkyl that is substituted by pyrryl, furyl, thienyl or by pyridyl, it being possible for these groups to be substituted in the same manner as phenyl, or each represents phenyl, pyrryl, furyl, thienyl or pyridyl, which groups may be substituted in the same manner as a phenyl-lower alkyl radical $R_7$, $R_8$ or $R_9$; in which $R_1$ and $R_2$ together or $R_1$ and $R_3$ together may represent $C_3$–$C_5$-lower alkylene in which the carbon atom bonded directly to the C2 - or C6-carbon atom of the 1,4-dihydropyridine ring is optionally replaced by an oxygen or sulphur atom or by a nitrogen atom that is substituted by hydrogen or lower alkyl, in which $R_4$ and $R_5$ may together represent unsubstituted or hydroxy-substituted $C_3$–$C_5$-lower alkylene, $C_2$–$C_4$-oxa- or $C_2$–$C_4$-thia-lower alkylene, in which $R_5$ and $R_6$ may together represent lower alkylene having from 2 to 5 chain carbon atoms or aza-lower alkylene having 3 or 4 chain carbon atoms, which radicals may be unsubstituted or substituted by hydroxy, lower alkoxy, amino, lower alkylamino or by di-lower alkylamino, and in which $R_8$ and $R_9$ may together represent $C_2$–$C_7$-lower alkylene, $C_3$–$C_4$-aza-, $C_3$–$C_4$-oxa- or $C_3$–$C_4$-thia-lower alkylene, these radicals being optionally substituted at carbon atoms by hydroxy, lower alkoxy, amino, lower alkylamino, di-lower alkylamino or by five- or six-membered monoaza- or diaza-heterocyclyl which is optionally substituted at carbon atoms by oxo and optionally substituted at the aza-nitrogen atoms by lower alkyl or phenyl, which may itself contain lower alkyl, halogen, lower alkoxy and/or nitro as substituent(s); and being optionally substituted at the aza-nitrogen atom by lower alkyl (which may itself be substituted by phenyl, pyrryl, furyl, thienyl and/or by pyridyl, which radicals themselves optionally contain lower alkyl, hydroxy, lower alkoxy, halogen and/or nitro as substituent(s), and/or by hydroxy, lower alkoxy, lower alkanoyloxy, amino, lower alkylamino and/or by di-lower alkylamino) by benzoyl, lower alkanoyl, furanylcarbonyl, thienylcarbonyl, pyrrylcarbonyl, pyridinylcarbonyl or by phenyl, which may itself contain lower alkyl, halogen, lower alkoxy and/or nitro as substituent(s), optical isomers of compounds of the formula I, mixtures of these optical isomers, and salts of such compounds having salt-forming groups.

4. Compounds of the formula I according to claim 1, in which n represents 1 or 2, Ar represents phenyl, thienyl, furyl or benzoxadiazolyl, which groups are optionally mono-, di- or tri-substituted by lower alkyl, lower alkoxy, halo-lower alkoxy, phenyl-lower alkoxy, phenyl-lower alkylthio, lower alkylenedioxy, halogen, trifluoromethyl, nitro, lower alkanoylamino and/or by cyano, the radical Ac represents lower alkanoyl, lower alkylsulphonyl, lower alkoxycarbonyl, 2-lower alkoxy-lower alkoxycarbonyl, N,N-di-lower alkylamino-lower alkoxycarbonyl, N-lower alkyl-N-phenyl-lower alkylamino-lower alkoxycarbonyl, carbamoyl, N-lower alkylcarbamoyl, N,N-di-lower alkylcarbamoyl, N,N-lower alkylenecarbamoyl or 4-morpholinocarbonyl, Z represents a radical —$OR_7$ or —$NR_8R_9$, $R_1$ represents hydrogen, lower alkyl, 2-(di-lower alkylamino)-lower alkyl, 2-(lower alkyleneamino)-lower alkyl, 2-4-morpholino)-lower alkyl, carboxy-lower alkyl or lower alkoxy-lower alkoxy-lower alkyl, $R_2$ and $R_3$, independently of one another, each represents lower alkyl, hydroxy-lower alkyl, cyano or amino, $R_4$ represents hydrogen or lower alkyl, $R_5$ represents hydrogen, lower alkyl that is unsubstituted or substituted by hydroxy, lower alkoxy, mercapto, lower alkylthio, carboxy, carbamoyl, amino, carbamoylamino, guanidino, phenyl, which may itself be hydroxy-substituted, or by imidazol-4-yl or indol-3-yl, or represents phenyl, thiazolyl, imidazolyl, furyl, thienyl, pyridyl or pyrimidinyl, which radicals are optionally substituted by hydroxy, lower alkoxy and/or by amino, $R_6$ represents hydrogen, lower alkyl, phenyl-lower alkyl, which is unsubstituted or substituted by hydroxy, lower alkoxy and/or by amino, or phenyl, thiazolyl, imidazolyl, furyl, thienyl, pyridyl or pyrimidinyl, which radicals are optionally substituted in the same manner as a phenyl-lower alkyl radical $R_6$, and $R_7$, $R_8$ and $R_9$, independently of one another, each represents hydrogen or lower alkyl that is unsubstituted or substituted by amino, lower alkylamino, di-lower alkylamino, lower alkyleneamino, oxa- or aza-lower alkyleneamino, in which the aza-nitrogen atom is optionally lower alkyl-substituted, hydroxy, lower alkoxy, phenyl, which may be unsubstituted or, for its part, amino-, hydroxy-, lower alkoxy- and/or halo-substituted, or by thienyl or pyridyl, which groups may be substituted in the same manner as phenyl; in which $R_4$ and $R_5$ may together represent $C_3$–$C_4$-lower alkylene, in which $R_5$ and $R_6$ may together represent $C_2$–$C_5$-lower alkylene or $C_4$-aza-lower alkylene and in which $R_8$ and $R_9$ may toggether represent $C_4$–$C_5$-lower alkylene which is optionally substituted by 2-imidazolidinon-1-yl, which may contain phenyl or lower alkyl as substituent in the 3-position, $C_4$-oxa- or $C_4$-aza-lower alkylene, in which the aza-nitrogen atom may be substituted by lower alkyl (which is itself unsubstituted or mono- or di-substituted by phenyl, which may contain lower alkyl, lower alkoxy, halogen and/or nitro as substituent(s), by thienyl and/or by pyridyl) or may be substituted by benzoyl, furanylcarbonyl, phenyl or by lower alkoxyphenyl, optical isomers of compounds of the formula I, mixtures of these optical isomers, and pharmaceutically acceptable salts of such compounds having salt-forming groups.

5. Compounds of the formula I according to claim 1, in which n represents 1 or 2, Ar represents phenyl that is unsubstituted or mono- or di-substituted by lower alkyl, lower alkoxy, halo-lower alkoxy, benzyloxy, benzylthio, halogen, trifluoromethyl, nitro and/or by cyano, or represents 2- or 3-thienyl or 2,1,3-benzoxadiazol-4-yl, the radical Ac represents lower alkylsulphonyl or lower alkoxycarbonyl, Z represents a radical $-OR_7$ or $-NR_8R_9$, $R_1$ represents hydrogen, and also 2-(4-morpholino)-ethyl, $R_2$ represents lower alkyl, hydroxymethyl, cyano or amino, $R_3$ represents lower alkyl, $R_4$ represents hydrogen or lower alkyl, $R_5$ represents hydrogen, lower alkyl that is unsubstituted or substituted by phenyl, which may itself be hydroxy-substituted, or represents phenyl or unsubstituted or amino-substituted thiazolyl, $R_6$ represents hydrogen, lower alkyl or phenyl, $R_7$ represents hydrogen, lower alkyl, or lower alkyl that is substituted by phenyl, amino, lower alkylamino, di-lower alkylamino, 4-morpholino, 1-piperazino, which may itself contain lower alkyl as substituent at the 4-nitrogen atom, or by lower alkoxy, $R_8$ and $R_9$, independently of one another, each represents hydrogen or lower alkyl that is unsubstituted or substituted by lower alkoxy, phenyl or by pyridyl; in which $R_4$ and $R_5$ may together represent 1,3-propylene, in which $R_5$ and $R_6$ may together represent 1,5-pentylene and in which $R_8$ and $R_9$ may together represent 1,5-pentylene, 3-(3-phenyl-2-imidazolidinon-1-yl)-1,5-pentylene, 3-(2-imidazolidinon-1-yl)-1,5-pentylene or 3-oxa- or 3-aza-1,5-pentylene, in which the aza-nitrogen atom is optionally substituted by lower alkyl, benzyl, diphenylmethyl, the radical benzyl or diphenylmethyl optionally containing halogen, lower alkyl and/or lower alkoxy as substituent(s), or by benzoyl, furanylcarbonyl, phenyl or by lower alkoxyphenyl, optical isomers of compounds of the formula I, mixtures of these optical isomers, and pharmaceutically acceptable salts of such compounds having salt-forming groups.

6. Compounds of the formula I according to claim 1, in which n represents 1, Ar represents 2- or 3-nitrophenyl, 2- or 3-difluoromethoxyphenyl, 2- or 3-methylphenyl, 2- or 3-trifluoromethylphenyl, 2,3-dimethylphenyl, 2,3-dichlorophenyl, 2- or 3-benzyloxyphenyl or 2- or 3-benzylthiophenyl, Ac represents lower alkoxy-carbonyl, Z represents a radical $-OR_7$ or $-NR_8R_9$, $R_1$ represents hydrogen, $R_2$ and $R_3$, independently of one another, each represents lower alkyl, $R_4$ represents hydrogen, $R_5$ represents lower alkyl or phenyl, $R_6$ represents hydrogen, $R_7$ represents lower alkyl that is unsubstituted or substituted by 4-morpholino, 1-piperazino or by 4-lower alkyl-1-piperazino, $R_8$ and $R_9$, independently of one another, each represents hydrogen or lower alkyl that is unsubstituted or substituted by phenyl or pyridyl; and in which $R_8$ and $R_9$ may together represent 3-aza-1,5-pentylene in which the aza-nitrogen atom is optionally substituted by benzyl or diphenylmethyl, optical isomers of compounds of the formula I, mixtures of these optical isomers, and pharmaceutically acceptable salts of such compounds having salt-forming groups.

7. Compounds of the formula I according to claim 1, in which the following configuration is present at the C4-carbon atom of the 1,4-dihydropyridine nucleus, in which the carbon atoms C3, C4 and C5 lie in the plane of the paper, the radical Ar lies above the plane of the paper and the hydrogen atom lies below the plane of the paper:

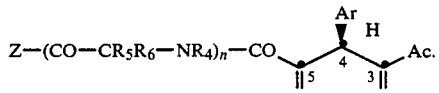

8. A compound of the formula I according to claim 1, in which n represents 1 or 2, Ar represents 2- or 3-nitrophenyl, 2- or 3-difluoromethoxyphenyl, 2- or 3-methylphenyl, 2- or 3-trifluoromethylphenyl, 2,3-dimethylphenyl, 2,3-dichlorophenyl, 2- or 3-benzyloxyphenyl, 2- or 3-benzylthiophenyl or 2,1,3-benzoxadiazol-4-yl, the radical Ac represents lower alkylsulphonyl or lower alkoxycarbonyl, Z represents a radical $-OR_7$ or $-NR_8R_9$, $R_1$ represents hydrogen, $R_2$ represents lower alkyl, hydroxymethyl, cyano or amino, $R_3$ represents lower alkyl, $R_4$ represents hydrogen, $R_5$ represents hydrogen, lower alkyl that is unsubstituted or substituted by phenyl, which may itself be hydroxy-substituted, or represents phenyl, $R_6$ represents hydrogen, lower alkyl or phenyl, $R_7$ represents hydrogen, lower alkyl, or lower alkyl that is substituted by phenyl, furyl, amino, lower alkylamino, di-lower alkylamino, 4-morpholino, 1-piperazino, which may itself contain lower alkyl or phenyl-lower alkyl as substituent at the 4-nitrogen atom, or by lower alkoxy, $R_8$ and $R_9$, independently of one another, each represents hydrogen or lower alkyl that is unsubstituted or substituted by lower alkoxy, phenyl or by pyridyl; in which $R_4$ and $R_5$ may together represent 1,3-propylene, in which $R_5$ and $R_6$ may together represent 1,5-pentylene and in which $R_8$ and $R_9$ may together represent 1,5-pentylene, 3-oxa- or 3-aza-1,5-pentylene, in which the aza-nitrogen atom is optionally substituted by lower alkyl, benzyl, diphenylmethyl, the radical benzyl or diphenylmethyl optionally containing halogen, lower alkyl and/or lower alkoxy as substituent(s); in the form of an optical isomer or as a mixture of optical isomers; and pharmaceutically acceptable salts of such a compound having a salt-forming group.

9. A compound of the formula I according to claim 1, in which n represents 1, Ar represents 2- or 3-nitrophenyl, 2- or 3-difluoromethoxyphenyl, 2- or 3-methylphenyl, 2- or 3-trifluoromethylphenyl, 2,3-dimethylphenyl, 2,3-dichlorophenyl, 2- or 3-benzyloxyphenyl, 2- or 3-benzylthiophenyl or 2,1,3-benzoxadiazol-4-yl, Ac represents lower alkoxycarbonyl, Z represents a radical —$OR_7$ or —$NR_8R_9$, $R_1$ represents hydrogen, $R_2$ represents lower alkyl, hydroxylower alkyl, cyano or amino, $R_3$ represents lower alkyl, $R_4$ represents hydrogen, $R_5$ represents lower alkyl or phenyl, $R_6$ represents hydrogen, $R_7$ represents lower alkyl, benzyl or furylmethyl and $R_8$ and $R_9$ together represent 3-aza-1,5-pentylene in which the aza-nitrogen is substituted by benzyl or diphenylmethyl; in the form of an optical isomer or as a mixture of optical isomers; and pharmaceutically acceptable salts of such a compound having a salt-forming group.

10. A compound of the formula I according to claim 1, in which n represents 1, Ar represents 3-nitrophenyl, Ac represents ($C_1$-$C_4$-alkoxy)carbonyl, Z represents a radical —$OR_7$, $R_1$ represents hydrogen, $R_2$ represents methyl, hydroxymethyl, cyano or amino, $R_3$ represents methyl, $R_4$ represents hydrogen, $R_5$ represents isopropyl, sec.-butyl or phenyl, $R_6$ represents hydrogen and $R_7$ represents $C_1$-$C_7$-alkyl; in the form of an optical isomer or as a mixture of optical isomers; and pharmaceutically acceptable salts of such a compound having a salt-forming group.

11. (−)-(4R)-1,4-dihydro-2,6-dimethyl-3-methoxycarbonyl-4-(3-nitrophenyl)-pyridine-5-carboxylic acid N-[(1S)-1-ethoxycarbonyl-2-methyl-1-propyl]-amide and pharmaceutically acceptable salts thereof according to claim 1.

12. (−)-(4R)-1,4-dihydro-2,6-dimethyl-3-isopropoxycarbonyl-4-(3-nitrophenyl)-pyridine-5-carboxylic acid N-[(1S)-1-ethoxycarbonyl-2-methyl-1-propyl]-amide and pharmaceutically acceptable salts thereof according to claim 1.

13. (−)-(4R)-1,4-dihydro-2,6-dimethyl-3-methoxycarbonyl-4-(3-nitrophenyl)-pyridine-5-carboxylic acid N-[(1S)-1-(n-butoxycarbonyl)-2-methyl-1-propyl]-amide and pharmaceutically acceptable salts thereof according to claim 1.

14. (4R,4S)-1,4-dihydro-2,6-dimethyl-3-methoxycarbonyl-4-(3-nitrophenyl)-pyridine-5-carboxylic acid N-[(1S,2S)-1-methoxycarbonyl-2-methyl-1-butyl]-amide, pharmaceutically acceptable salts and the optical isomers thereof according to claim 1.

15. (4R)-1,4-dihydro-2,6-dimethyl-3-methoxycarbonyl-4-(3-nitrophenyl)-pyridine-5-carboxylic acid N-[(1S,2S)-1-ethoxycarbonyl-2-methyl-1-butyl]-amide and pharmaceutically acceptable salts thereof according to claim 1.

16. (4S,4R)-1,4-dihydro-2,6-dimethyl-3-methoxycarbonyl-4-(3-nitrophenyl)-pyridine-5-carboxylic acid N-{(1S)-1-[2-(4-morpholino)-1ethoxy]-carbonyl-2methyl-1-propyl}-amide, pharmaceutically acceptable salts and the optical isomers thereof according to claim 1.

17. 1,4-Dihydro-2,6-dimethyl-3-methoxycarbonyl-4-(3-nitrophenyl)-pyridine-5-carboxylic acid N-[1-(4-benzyl-1-piperazinyl)-carbonyl-2-methyl-1-propyl]-amide, pharmaceutically acceptable salts and the optical isomers thereof according to claim 1.

18. (−)-(4R)-1,4-dihydro-2,6-dimethyl-3-ethoxycarbonyl-4-(3-nitrophenyl)-pyridine-5-carboxylic acid N-[(1S)-1-ethoxycarbonyl-2-methyl-1-butyl]-amide and pharmaceutically acceptable salts thereof according to claim 1.

19. (4S,4R)-1,4-dihydro-2,6-dimethyl-3-methoxycarbonyl-4-(3-nitrophenyl)-pyridine-5-carboxylic acid N-[(1S)-1-(4-diphenylmethyl-1-piperazinyl)-carbonyl-2-methyl-1-propyl]-amide, pharmaceutically acceptable salts and the optical isomers thereof according to claim 1.

20. 1,4-Dihydro-2,6-dimethyl-3-methoxycarbonyl-4-(3-nitrophenyl)-pyridine-5-carboxylic acid N-(1-ethoxycarbonyl-2-methyl-1-propyl)-amide according to claim 1.

21. 1,4-Dihydro-2,6-dimethyl-3-isopropoxycarbonyl-4-(3-nitrophenyl)-pyridine-5-carboxylic acid N-(1-ethoxycarbonyl-2-methyl-1-propyl)-amide according to claim 1.

22. 1,4-Dihydro-2,6-dimethyl-3-methoxycarbonyl-4-(3-nitrophenyl)-pyridine-5-carboxylic acid N-[1-(n-butoxycarbonyl)-2-methyl-1-propyl]-amide according to claim 1.

23. 1,4-Dihydro-2,6-dimethyl-3-methoxycarbonyl-4-(3-nitrophenyl)-pyridine-5-carboxylic acid N-(1-ethoxycarbonyl-2-methyl-1-butyl)-amide according to claim 1.

24. 1,4-Dihydro-2,6-dimethyl-3-methoxycarbonyl-4-(3-nitrophenyl)-pyridine-5-carboxylic acid N-[1-(4-benzyl-1-piperazinyl)-carbonyl-2-methyl-1-propyl]-amide according to claim 1.

25. 1,4-Dihydro-2,6-dimethyl-3-methoxycarbonyl-4-(3-nitrophenyl)-pyridine-5-carboxylic acid N-[1-(4-diphenylmethyl-1-piperazinyl)-carbonyl-2-methyl-1-propyl]-amide according to claim 1.

26. 1,4-Dihydro-2,6-dimethyl-3-methoxycarbonyl-4-(3-nitrophenyl)-pyridine-5-carboxylic acid N-[1-(n-hexyloxycarbonyl)-2-methyl-1-propyl]-amide according to claim 1.

27. 2-Amino-1,4-dihydro-6-methyl-3-methoxycarbonyl-4-(3nitrophenyl)-pyridine-5-carboxylic acid N-[1-(n-butoxycarbonyl)-2-methyl-1-propyl]-amide according to claim 1.

28. 1,4-dihydro-2,6-dimethyl-3-methoxycarbonyl-4-(3-nitrophenyl)-pyridine-5-carboxylic acid N-[1-(2-furylmethoxycarbonyl)-2-methyl-1-propyl]-amide according to claim 1.

29. 1,4-dihydro-2,6-dimethyl-3-methoxycarbonyl-4-(3-nitrophenyl)-pyridine-5-carboxylic acid N-[1-(tert.-butyloxycarbonyl)-2-methyl-1-propyl]-amide according to claim 1.

30. 1,4-dihydro-2,6-dimethyl-3-methoxycarbonyl-4-(3-nitrophenyl)-pyridine-5-carboxylic acid N- {1-[(3- hydroxy-1-propoxy)-carbonyl]-2-methyl-1-propyl }-amide according to claim 1.

31. Pharmaceutical preparations containing a compound of the formula I according to claim 1 or a pharmaceutically acceptable salt thereof in combination with a pharmaceutically acceptable carrier.

32. A method of treating cardiovascular disorders in mammals comprising the administration to a mammal in need thereof of a therapeutically effective amount of a compound of formula I according to claim 1 or of a pharmaceutically acceptable salt thereof.

* * * * *